US008394779B2

(12) United States Patent
Ingber et al.

(10) Patent No.: US 8,394,779 B2

(45) Date of Patent: Mar. 12, 2013

(54) METHODS OF MODULATING ANGIOGENESIS VIA TRPV4

(75) Inventors: Donald E. Ingber, Boston, MA (US); Charles K. Thodeti, Copley, OH (US)

(73) Assignee: Children's Medical Center Corporation, Boston, MA (US)

(*) Notice: Subject to any disclaimer, the term of this patent is extended or adjusted under 35 U.S.C. 154(b) by 0 days.

(21) Appl. No.: 12/996,069

(22) PCT Filed: Jun. 4, 2009

(86) PCT No.: PCT/US2009/046219

§ 371 (c)(1),
(2), (4) Date: Mar. 4, 2011

(87) PCT Pub. No.: WO2009/149239

PCT Pub. Date: Dec. 10, 2009

(65) Prior Publication Data

US 2011/0150894 A1 Jun. 23, 2011

Related U.S. Application Data

(60) Provisional application No. 61/058,647, filed on Jun. 4, 2008.

(51) Int. Cl.
*C12N 15/11* (2006.01)

(52) U.S. Cl. .......... 514/44 A

(58) Field of Classification Search .......... 514/44 A
See application file for complete search history.

(56) References Cited

U.S. PATENT DOCUMENTS

2005/0182011 A1 8/2005 Olson et al.

OTHER PUBLICATIONS

O'Neil et al. Pflugers Arch-Eur J Physiol (2005) 451:193-203.*

Alvarez, D. F. et al. Transient receptor potential vanilloid 4-mediated disruption of the alveolar septal barrier: a novel mechanism of acute lung injury. Circ Res 99, 988-95 (2006).

Ingber, D. Extracellular matrix and cell shape: potential control points for inhibition of angiogenesis. J. Cell Biochem 47, 236-41 (1991).

Inoue, R. et al. Transient receptor potential channels in cardiovascular function and disease. Circ. Res. 99, 119-31 (2006).

Kohler, R. et al., Evidence for a functional role of endothelial transient receptor potential V4 in shear stress-induced vasodilatation. Arterioscler Thromb Vasc. Biol. 26, 1495-502 (2006).

Wang, N., Butler, J.P. & Ingber, D. E. Mechanotransduction across the cell surface and through the cytoskeleton. Science 260, 1124-7 (1993).

Kippenberger et al., "Mechanical Stretch Stimulates Protein Kinase B/Akt." The Journal of Biological Chemistry 2005, 280(4); pp. 3060-3067.

Kwan et al., "TRP channels in endothelial function and dysfunction." Biochimica et Biophysica Acta 2007, 1772, pp. 907-914.

Vriens et al., "TRPV channels and modulation by hepatocyte growth factor/scatter factor in human hepatoblastoma (HepG2) cells." Cell Calcium 2004, 36, pp. 19-28.

* cited by examiner

*Primary Examiner* — Brian Whiteman

(74) *Attorney, Agent, or Firm* — David S. Resnick; Tari W. Mills; Nixon Peabody LLP

(57) ABSTRACT

The present invention relates to methods of inhibiting capillary endothelial (CE) cell migration, the formation of CE networks and angiogenesis, and uses thereof for the purpose of treating angiogenesis-related diseases and disorders, particularly when the diseases or disorders are directly related aberrant angiogenesis. Inhibition is achieved by inhibiting TRPV4 activity, such as the levels of TRPV4 expression, calcium influx through TRPV4, and/or the intracellular signaling from TRPV4 via β1 integrin activation.

4 Claims, 10 Drawing Sheets siRNA
Con
TRPV4
12G10
actin
Strain: 0 5 15 0 5 15 min

Control siRNA
TRPV4 siRNA
12G10 binding (fold over basal)
0 min 5 min 15 min p-AKT
AKT
p-ERK
ERK AKT phosporylation (fold over basal)
ERK1/2 phosporylation (fold over basal)

METHODS OF MODULATING ANGIOGENESIS VIA TRPV4

CROSS REFERENCE TO RELATED APPLICATION

This application is a 35 U.S.C. §371 National Phase Entry application of International Application No. PCT/US2009/046219 filed on Jun. 6, 2009, which designates the United States, and which claims benefit of priority under 35 U.S.C. §119(e) of the U.S. provisional application 61/058,647 filed Jun. 4, 2008, the contents of which are incorporated herein by reference in their entirety.

GOVERNMENT SUPPORT

This invention was made with Government support under Grant No.: CA45548 awarded by the National Institutes of Health. The Government has certain rights in the invention.

BACKGROUND OF INVENTION

Angiogenesis is the formation, development and growth of new blood vessels. The normal regulation of angiogenesis is governed by a fine balance between factors that induce the formation of blood vessels and those that halt or inhibit the process. When this balance is upset, it generally results in pathological angiogenesis. Under normal physiological conditions, angiogenesis occur in very specific, restricted situations and is highly regulated through a system of angiogenic stimulators and inhibitors. For example, angiogenesis is normally observed in wound healing, fetal and embryonal development, and formation of the corpus luteum, endometrium and placenta.

In addition, angiogenesis is regulated by external factors. Physical forces applied to extracellular matrix (ECM) can influence the direction of capillary endothelial (CE) cell migration and oriented sprouting that drive angiogenesis. For example, the initial step in neovascularization involves reorientation of a subset of CE cells that spread and migrate perpendicular to the main axis of the pre-existing vessel towards the angiogenic stimulus. The growth and development of all living tissues are influenced by physical forces, and deregulation of this form of mechanoregulation can lead to various diseases and debilitating conditions. This is particularly evident in the cardiovascular system where blood pressure, wall strain and fluid shear stress elicit biochemical signals in endothelial cells that are required for normal tissue homeostasis, and when these physical factors are altered, they produce changes in cell function and vascular wall remodeling that can contribute to life threatening diseases, such as hypertension and atherosclerosis. Mechanical forces also play an important role in the microvasculature. For example, micromechanical stresses (e.g., cyclical changes in wall strain in angiogenic atherosclerotic plaques, static stretch in healing wounds or cancer parenchyma) can be potent inducers of CE reorientation and capillary ingrowth as chemical factors. Moreover, physical forces actually dominate and govern the local capillary response (i.e., whether CE cells will grow, differentiate, die or move in a specific direction) when stimulated by saturating amounts of soluble angiogenic factors. Thus, understanding the molecular mechanism by which CE cells reorient when exposed to mechanical stress could lead to identification of novel targets for therapy in angiogenic diseases, such as cancer, arthritis and diabetic retinopathy.

SUMMARY OF THE INVENTION

The present invention relates to methods of inhibiting endothelial cell migration and angiogenesis, and uses thereof for the purpose of treating angiogenesis-related diseases and disorders, particularly when the diseases or disorders are directly related aberrant angiogenesis.

Embodiments of the present invention are based on the identification of TRPV4 as the stress-activated (SA) ion channel responsible for β1 integrin activation in response to mechanical strain application to microvascular cells. Mechanical strains imposed upon endothelial cells through their extracellular matrix adhesions via integrins influence the re-arrangement of the cells' cytoskeleton which in turn influences the migration capability of these cells that is needed for re-aligning and/or reorienting the cells with respect of the orientation of the strain experienced. The ability of endothelial cells to sense and respond to mechanical stress is necessary for the formation of new blood vessels. The inventors have identified TRPV4 as the mechanochemical 'transducer' that detects mechanical strain and transduces the strain into a chemical signal intracellularly that in turn chemically activates β1 integrin, which are transmembrane protein receptors that convey additional migratory and growth signals to the cell when they link the cytoskeleton to the extracellular matrix to which they bind. The signal transduction that leads to integrin activation and subsequent changes in CE cell behavior is by way of a rapid influx of $Ca^{2+}$ via the cell surface TRPV4 ion channel into the cell. This increase in intracellular $Ca^{2+}$ activates the $Ca^{2+}$ dependent PI3/AKT kinase pathway comprising the phosphorylation of the intracellular tail domain of the β1 integrin thereby activating the integrin, and the phosphorylation and translocation of the AKT protein. The inventors show that siRNAs of TRPV4 can reduce capillary endothelial (CE) cell migration and formation of CE vascular networks, and that TRPV4 is required for CE cell migration and angiogenesis.

Accordingly, provided herein is a method for inhibiting endothelial cell migration, the method comprising contacting an endothelial cell with a TRPV4 inhibitor.

In one embodiment, provided herein is a method for inhibiting endothelial cell migration, the method comprising contacting an endothelial cell with an siRNA directed specifically against a TRPV4 gene.

In another embodiment, provided herein is a method for inhibiting endothelial cell migration, the method comprising contacting an endothelial cell with an antibody directed specifically against a β1 integrin, wherein the integrin function is blocked by the antibody.

In one embodiment, the antibody is a monoclonal antibody derived from clone P5D2.

In one embodiment, provided herein is a method for inhibiting angiogenesis in a mammal in need thereof, the method comprising administering a therapeutically effective amount of a TRPV4 inhibitor and a pharmaceutically acceptable carrier.

In another embodiment, provided herein is a method of treating an angiogenesis-related disease in a mammal in need thereof, the method comprising administering a therapeutically effective amount of a TRPV4 inhibitor and a pharmaceutically acceptable carrier.

In some aspect, a TRPV4 inhibitor is any molecule that inhibits of the expression or ion transporting function of TRPV4, or that inhibits the consequences of an activated TRPV4, i.e. the downstream signal transduction via $Ca^{2+}$ influx and the $Ca^{2+}$ dependent PI3/AKT kinase pathway and/or the activity of the β1 integrin in a CE cell.

In one embodiment, the TRPV4 inhibitor that inhibits an expression of TRPV4 in the cell. Such an inhibitor can be an RNA interference molecule.

In one embodiment, the TRPV4 inhibitor is an siRNA or dsRNA that inhibits of expression of TRPV4. The siRNA can be designed in the form of a small hairpin RNA (shRNA) expressed from a vector. The vector carrying the shRNA can be transfected into the CE cells.

In one embodiment, the TRPV4 inhibitor inhibits an influx of calcium into the cell via the TRPV4 ion channel. Such compounds include small molecules ruthenium red and gadolinium chloride.

In one embodiment, the TRPV4 inhibitor inhibits the phosphorylation of β1 integrin in the cell.

In one embodiment, the TRPV4 inhibitor inhibits the phosphorylation of AKT in the cell.

In one embodiment, the TRPV4 inhibitor is selected from the group consisting of an antibody, an RNA interference molecule, a small molecule, a peptide and an aptamer.

In one embodiment, the endothelial cell is a mammalian endothelial cell. In another embodiment, the mammalian endothelial cell is a human endothelial cell.

In one embodiment, the angiogenesis-related disease include but are not limited to cancer, macular degeneration; diabetic retinopathy; rheumatoid arthritis; Alzheimer's disease; obesity, psoriasis, atherosclerosis, vascular malformations, angiomata, and endometriosis.

In one embodiment, the treatment of angiogenesis-related diseases related to the eyes, e.g. macular degeneration or diabetic retinopathy, comprises directly injecting an siRNA, dsRNA, or shRNA vector directed against a TRPV4 gene into the vitreous cavity of the affected eye.

In one embodiment, the treatment of angiogenesis-related diseases related to the eyes, e.g. macular degeneration or diabetic retinopathy, comprises directly injecting an antibody specifically against a β1 integrin function into the vitreous cavity of the eye, wherein the integrin function is blocked by the antibody.

In other embodiments, the treatment of angiogenesis-related diseases having localized aberrant angiogenesis, e.g. solid non-metastatic tumor, arthritis, and endometriosis, comprises directly injecting an siRNA, dsRNA, or shRNA vector directed against a TRPV4 gene to the location or tissue with aberrant angiogenesis.

In other embodiments, the treatment of angiogenesis-related diseases having localized aberrant angiogenesis, e.g. solid non-metastatic tumor, arthritis, and endometriosis, comprises directly injecting an antibody specifically against a β1 integrin function into the location or tissue with aberrant angiogenesis, wherein the integrin function is blocked by the antibody.

In one embodiment, the TRPV4 inhibitor is administered in conjunction with an anti-angiogenic therapy or anti-proliferation therapy. Such therapies include anti-VEGF therapy, chemotherapy, radiation, antibody-based therapy and immune system enhancement therapy, e.g. granulocyte stimulation factor (GSF) therapy.

In one embodiment, the mammal in need of treatment is a human.

DETAILED DESCRIPTION OF THE INVENTION

Figures 1, 2A, 2B, 2C, 2D, 2E:
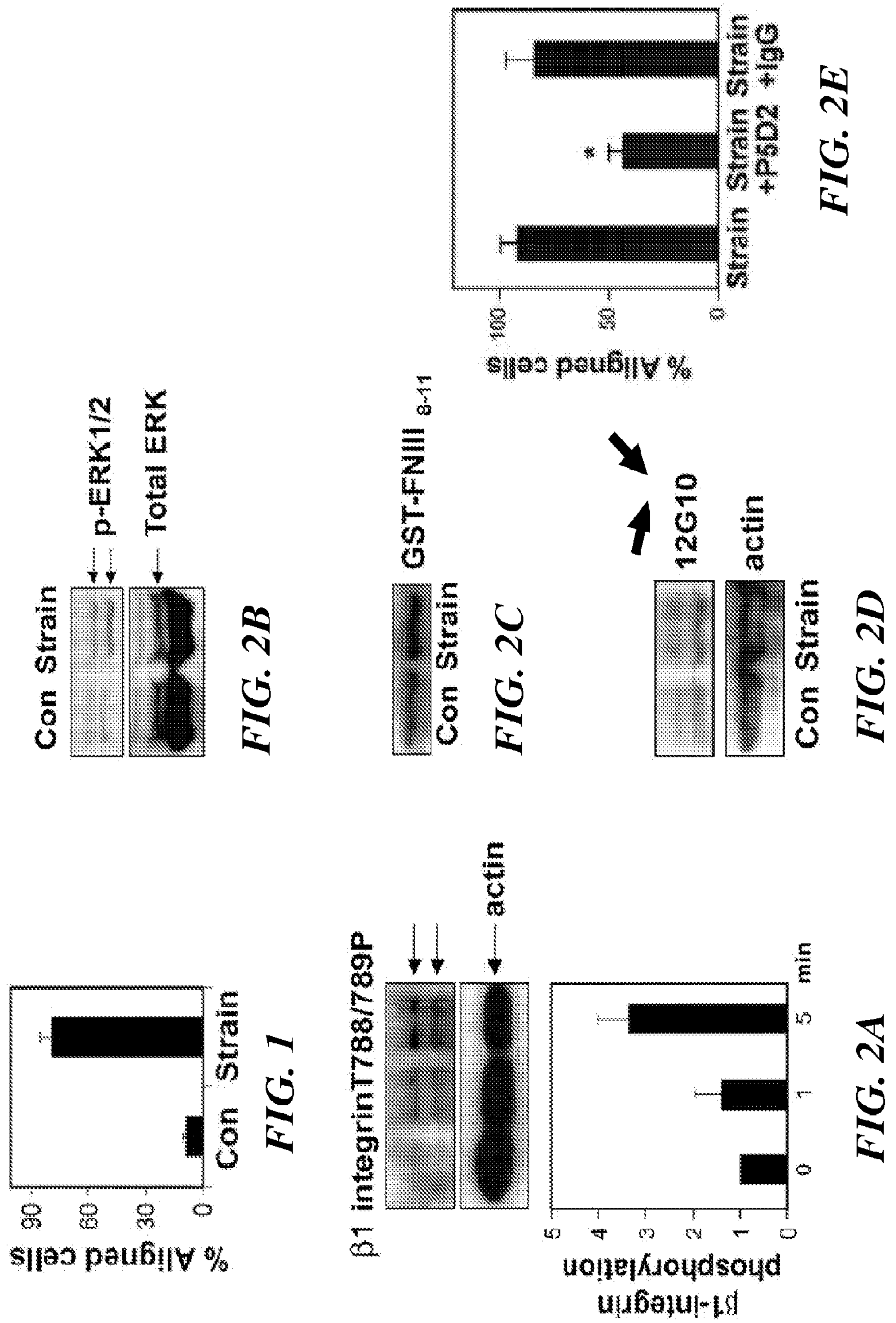
FIG. 1 shows the percentage of cells oriented 90±30° degrees (aligned) relative to the direction of applied strain in control and strain exposed cells ($p<0.0006$).
FIG. 2A shows the Western blot analysis of CE cell lysates showing time-dependent phosphorylation of β1 integrin cytoplasmic tail at threonine T788/789 in response to mechanical strain. Histogram shows the corresponding densitometric quantification of β1 integrin phosphorylation.
FIG. 2B are the Western blots showing the MAP kinase (ERK1/2) phosphorylation in CE cells in the absence and presence of mechanical strain.
FIG. 2C are the Western blots showing the binding of GST-$FNIII_{8-11}$ in CE cells in the absence and presence of mechanical strain.
FIG. 2D are Western blots showing the binding of specific antibody against activated β1 integrin, 12G10 in CE cells in the absence and presence of mechanical strain.
FIG. 2E shows the percentage of cells oriented 90±30° degrees (aligned) relative to the direction of applied cyclic strain in the absence or presence of the integrin blocking antibody P5D2 (*$p<0.001$).

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (3rd ed.), Cold Spring Harbor Laboratory Press, Cold Spring Harbor, N.Y., USA (2000); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Meolcular Biology, Vo. 203, 2003, Transgenic Mouse, editored by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention relates to methods of regulating endothelial cell migration and angiogenesis, and uses thereof for the purpose of treating angiogenesis-related diseases and disorders, particularly when the diseases or disorders is directly related aberrant angiogenesis.

Figure 3A:
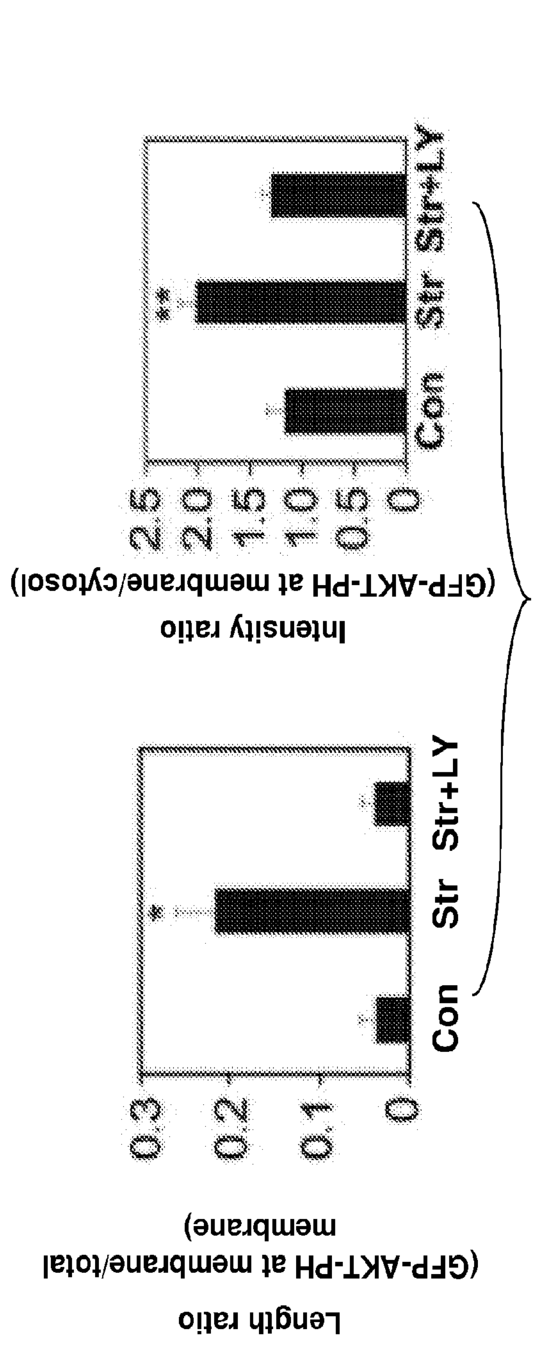
FIG. 3A shows the quantification of mechanical strain—induced GFP-AKT-PH domain translocation to the membrane in the absence or presence of the PI3K inhibitor LY294002, measured as a fraction of total cell membrane perimeter that is enhanced with GFP-AKT-PH in randomly selected cells and the ratio of GFP fluorescence intensity in the membrane vs cytosol (*$P<0.05$).
Figure 3B:
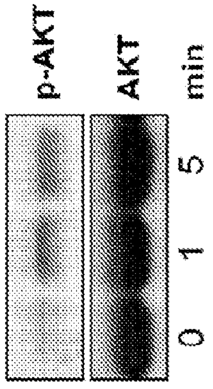
FIG. 3B shows the representative Western blots showing time-dependent phosphorylation of AKT at ser-473 in response to mechanical strain in the presence and absence of the PI3K inhibitor, LY294002.
Figure 3C:
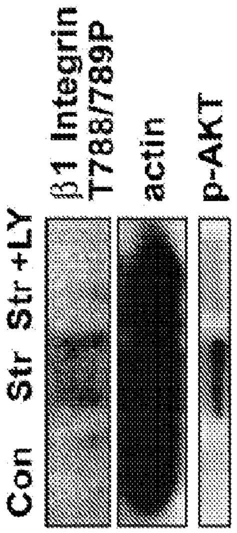
FIG. 3C shows the representative Western blots showing phosphorylation of β1 integrin cytoplasmic tail at T788/789 and AKT at ser-473 in response to mechanical strain in the presence and absence of the PI3K inhibitor, LY294002.
Figures 4A, 4B, 4C, 4D, 4E:
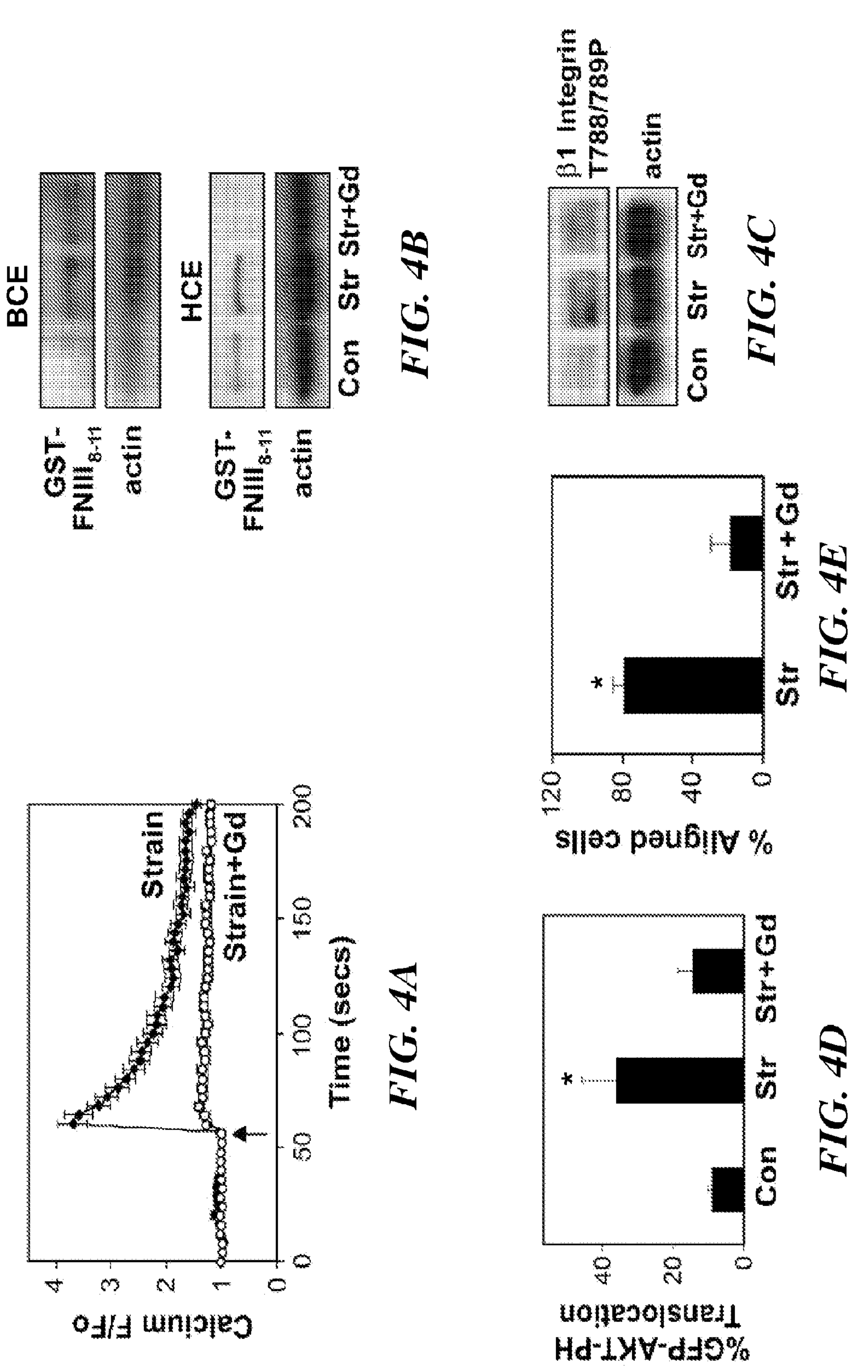
FIG. 4A shows the relative change in cytosolic calcium in Fluo-4 loaded CE cells in response to applied mechanical strain (15%, 3 sec, arrow) in the absence (●) and presence (○) of gadolinium chloride (25 μM;Gd) (F/Fo=ratio of normalized FLUO-4 fluorescence intensity relative to time 0). Stretch-activated (SA) calcium channels are upstream of mechanical strain-induced β1 integrin phosphorylation.
FIG. 4B are the representative Western blots showing mechanical strain dependent binding of GST-$FNIII_{8-11}$ fragment in bovine (BCE)and human (HCE) CE cells in the absence and presence of gadolinium.
FIG. 4C shows the representative Western blots of β1-integrin phosphorylation in bovine (BCE)and human (HCE) CE cells in the absence and presence of gadolinium.
FIG. 4D shows the percentages of CE cells displaying GFP-AKT-PH domain translocation to the plasma membrane when subjected to 0 or 15% mechanical strain in the absence and presence of gadolinium chloride (*$p<0.022$).
FIG. 4E shows the percentage of CE cells oriented 90±30° degrees (aligned) relative to the direction of applied strain in the absence and presence of gadolinium chloride (*$p<0.0002$).
Figure 5A:
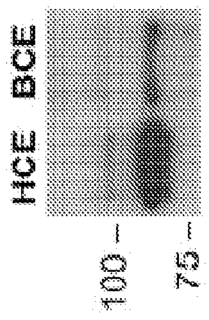
FIG. 5A shows the Western blotting analysis showing the expression of TRPV4 in human and bovine CE cells.
Figure 5B:
FIG. 5B shows the representative RT-PCR result confirming knockdown of TRPV2 and TRPV4 mRNA levels in CE cells using specific siRNAs respectively.
Figure 5C:
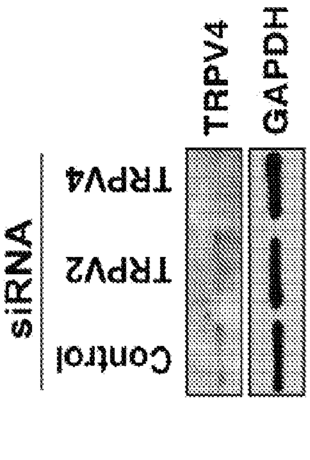
FIG. 5C shows the suppression of protein expression TRPV4 in CE cells using specific TRPV4 siRNA.
Figure 5D:
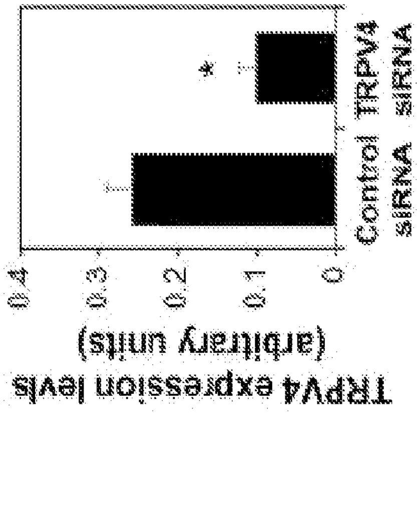
FIG. 5D show a histogram of the suppression of TRPV4 protein levels in bovine CE cells using specific TRPV4 siRNAs (*$P<0.05$).
Figure 5E:
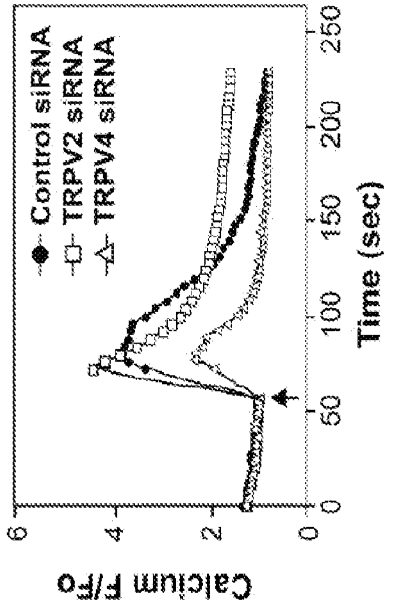
FIG. 5E shows the relative change in cytosolic calcium in response to mechanical strain (15%, 4 sec, arrow) in FLUO-4 loaded CE cells treated with indicated siRNA.
Figure 5F:
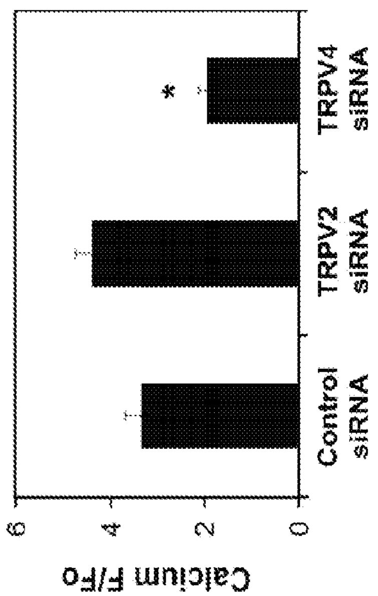
FIG. 5F shows the average relative increases in cytosolic calcium induced by mechanical strain in CE cells treated with the indicated siRNAs (*, $p<0.02$; n=3 independent experiments).

Embodiments of the present invention are based on the identification of TRPV4 as the stress-activated (SA) ion channel responsible for β1 integrin activation in response to mechanical strain application to microvascular cells. Mechanical strains imposed upon endothelial cells influence the re-arrangement of the cells' cytoskeleton which in turn influence the migration capability of these cells that is needed for re-aligning and/or reorienting the cells with respect of the orientation of the strain experienced. The ability of endothelial cells to sense and respond to mechanical stress is necessary for the formation of new blood vessels. The inventors have identified TRPV4 as the mechanochemical "transducer" that detects mechanical strain and transduces the strain into a chemical signal intracellularly through the activation of β1 integrin, a transmembrane protein receptor that links the cytoskeleton to the extracellular matrix. The signal transduction is by way of a rapid influx of $Ca^{2+}$ via the cell surface TRPV4 ion channel into the cell (FIGS. 4A, 5E and 6A). This increase in intracellular $Ca^{2+}$ activates the $Ca^{2+}$ dependent PI3/AKT kinase pathway, which leads to the phosphorylation of the intracellular tail domain of the β1 integrin, thereby activating this signaling adhesion receptor (FIGS. 2 and 3), and the phosphorylation and translocation of the AKT protein (FIGS. 3 and 4).

Figure 6A:
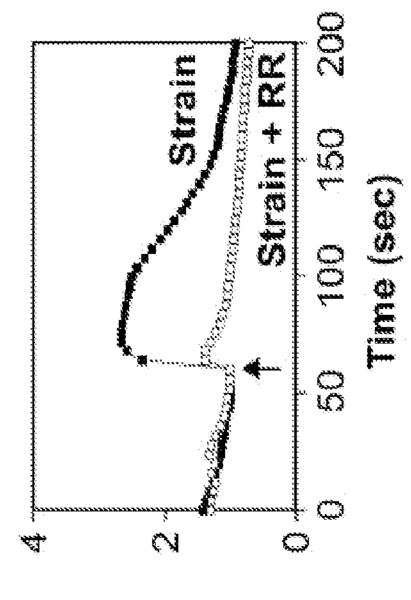
FIG. 6A shows the relative changes in cytosolic calcium in Fluo-4 loaded CE cells in response to mechanical strain (15%, 4 sec, arrow) in the absence (■) and presence (□) of the specific TRPV inhibitor ruthenium red (RR).
Figure 6B:
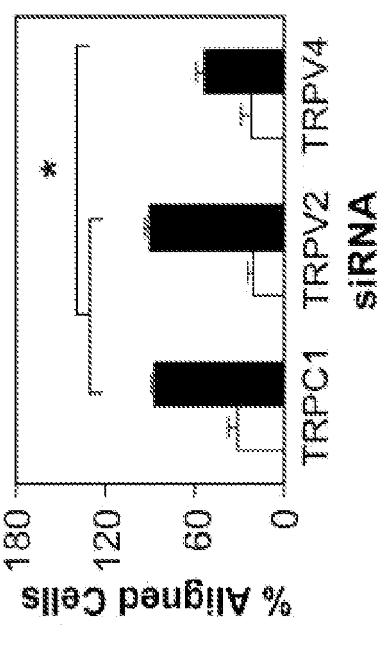
FIG. 6B shows the percentage of cells oriented 90±30° degrees (aligned) relative to the direction of applied strain in control (white bars) and strain exposed (black bars) human CE cells treated with the indicated siRNA. Note that TRPV4 siRNA treated cells failed to reorient fully compared to TRPV2 or TRPC1 treated cells (*, $p<0.0025$).
Figure 7C:
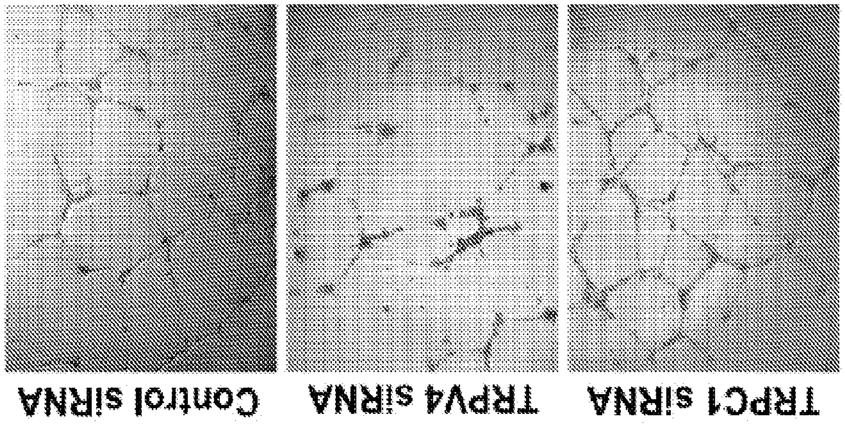
FIG. 7C shows the phase contrast photomicrographs of human CE cells treated with the indicated siRNA showing that TRPV4 siRNA completely inhibited capillary tube formation in a MATRIGEL™ angiogenesis assay at 18 hr, whereas treatment with control and TRPC1 siRNA had no effect.
Figure 7A:
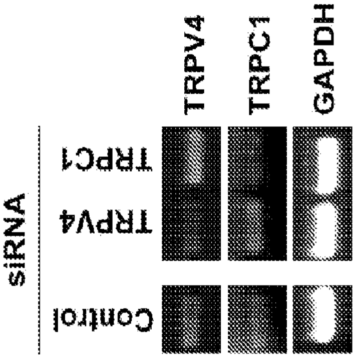
FIG. 7A shows the representative RT-PCR analysis showing the efficiency and specificity of siRNA suppression of TRPV4 and TRPC1 mRNA levels in human CE cells.
Figure 7B:
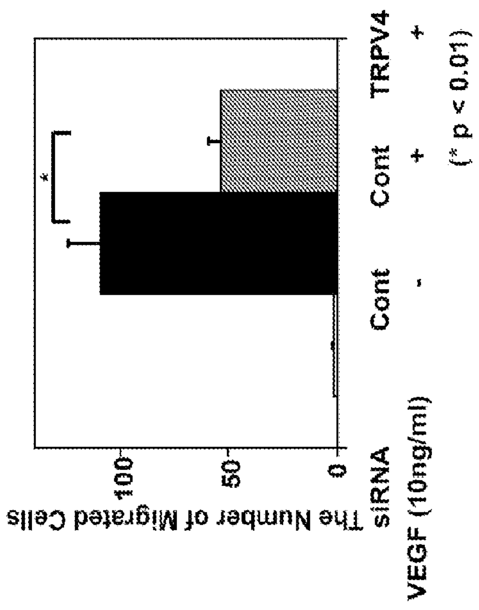
FIG. 7B shows the migration of human CE cells treated with the indicated siRNAs showing that TRPV4 siRNA significantly inhibited VEGF-induced migration of CE cells compared to control siRNA treated cells.

The inventors showed that inhibition of the TRPV4 channel using a TRPV4 inhibitor ruthenium red (FIG. 6A) or a SA ion channel inhibitor gadolinium chloride (FIG. 4A), or by inhibiting the expression of TRPV4 by a siRNA specific for TRPV4 (FIG. 5E) resulted in reduced influx of $Ca^{2+}$ into mechanically strained CE cells. There are also concomitant reduction in phosphorylation of β1 integrin (FIGS. 2A, 3C and 4C), reduction in the phosphorylation and translocation of the AKT protein (FIGS. 3 and 4D), consequential reduction in the re-alignment of CE cells (FIGS. 2E, 4E, 6B and C), and inhibition of capillary tube formation (FIG. 7B). Moreover, the inventors showed that the $Ca^{2+}$ dependent PI3/AKT kinase pathway and the activation of the β1 integrin are necessary for the cytoskeletal rearrangement and alignment of CE. Inhibition of the $Ca^{2+}$ dependent PI3/AKT kinase pathway using LY 294002 or the function-blocking anti-β1 integrin antibody (clone P5D2) (Mukhopadhyay, N. K. et al., 2004, Ann. Thorac. Surg. 78:450; Blaschke, F. et al., 2002, Biochem. Biophys. Res. Commun. 296:890) greatly reduced CE cell re-alignment when subjected to mechanical strain (FIGS. 3 and 2E). Therefore, inhibition of the expression of TRPV4 or inhibiting the consequences of an activated TRPV4, i. e. the downstream signal transduction events via blocking of the signal transducing $Ca^{2+}$ dependent PI3/AKT kinase pathways and/or blocking the activity of an activated β1 integrin, can be used to inhibit CE cell alignment, CE cell migration, inhibition of capillary tube formation and overall angiogenesis.

Accordingly, embodiments of the invention provide methods for inhibiting endothelial cell migration and angiogenesis, the method comprising contacting an endothelial cell with a TRPV4 inhibitor.

In one embodiment, provided herein is a method for inhibiting endothelial cell migration and angiogenesis, the method comprising contacting an endothelial cell with an siRNA directed specifically against a TRPV4 gene.

In another embodiment, provided herein is a method for inhibiting endothelial cell migration and angiogenesis, the method comprising contacting an endothelial cell with an antibody directed specifically against a β1 integrin, wherein the integrin function is blocked by the antibody.

As used herein, when an β1 integrin function is blocked, there is reduced or no downstream phosphorylation of various signaling pathways known to be associated with β1 integrin, e.g. the RhoA, Rac1, Ras, Raf, MEK, ERK, and JNK pathways. In one embodiment, the β1 integrin activated, meaning that the integrin is phosphorylated.

In one embodiment, the antibody is a monoclonal antibody derived from clone P5D2. P5D2 has been shown to be a function-blocking β1 integrin antibody in that it inhibits the downstream phosphorylation of various signaling pathways known to be associated with activated β1 integrin.

Embodiments of the invention also provide methods for inhibiting angiogenesis in a mammal in need thereof, the method comprising administering a therapeutically effective amount of a TRPV4 inhibitor and a pharmaceutically acceptable carrier.

Embodiments of the invention also provide methods for treating an angiogenesis-related disease in a mammal in need thereof, the method comprising administering a therapeutically effective amount of a TRPV4 inhibitor and a pharmaceutically acceptable carrier.

As used herein, inhibiting endothelial cell migration refers to the reduction in cell migration and/or capillary tube formation in the presence of a TRPV4 inhibitor. Assays for in vitro cell migration and capillary tube formation are well known to one skilled in the art, e.g. in Lingen M W, 2003, Methods Mol Med. 78:337-47 and McGonigle and Shifrin, 2008, Curr. Prot. Pharmacology, Unit 12.12, and any angiogenesis assays known in the art or described herein.

As used herein, the term "inhibiting angiogenesis" means the reduction or prevention of growth of new blood vessels. Inhibition include slowing the rate of growth. The growth rate can be reduced by about 20%, about 30%, about 40%, about 50%, about 60%, about 70%, about 80%, about 90%, about 100%, about 125%, about 150% or more compared to a control, untreated condition. Inhibition also means no further growth of new blood vessels from the time of start of treatment administration. Angiogenesis can be detected by methods known in the art and/or with any angiogenesis assays known in the art or described herein.

As used herein, the term "angiogenic disease or disorder" refers to diseases or disorders that are the direct result of aberrant blood vessel proliferation (e.g. diabetic retinopathy, vascular malformations, angiomata, and hemangiomas) or undesired or pathological blood vessel proliferation (e.g. in the case cancer and tumor growth). The term also refers to diseases or disorders whose pathological progression is dependent on a good blood supply and thus blood vessel proliferation. Examples include but are not limited to abnormal vascular proliferation, ascites formation, psoriasis, age-related macular degeneration, thyroid hyperplasia, preeclampsia, rheumatoid arthritis and osteo-arthritis, Alzheimer's disease, obesity, psoriasis, atherosclerosis, vascular malformations, angiomata, pleural effusion, atherosclerosis, endometriosis, diabetic/other retinopathies, ocular neovascularization.

As used herein, the term "a TRPV4 inhibitor" is any molecule that inhibits of expression of TRPV4, the ion transport through the TRPV4channel, or inhibits the consequences of an activated TRPV4, i.e. the downstream signal transduction via $Ca^{2+}$ influx, via the $Ca^{2+}$ dependent PI3/AKT kinase pathway and/or the activity of the β1 integrin in a CE cell. For example, a TRPV4 inhibitor can be an siRNA or dsRNA that inhibits of expression of TRPV4, a TRPV4 inhibitor, a TRPV4 antagonist, a SA ion channel inhibitor or a function-blocking anti β1 integrin antibody. Examples include but are not limited to small molecules ruthenium red gadolinium chloride and LY 294002, and the monoclonal antibody anti-β1 integrin derived from clone P5D2 as described herein.

In one embodiment, the TRPV4 inhibitor is selected from the group consisting of an antibody, an RNA interference molecule, a small molecule, a peptide and an aptamer.

As used herein, the term "peptide" refer to a polymer of up to 20 amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. "Peptide" further refer to amino acids joined to each other by peptide bonds or modified peptide bonds, i.e., peptide isosteres, and can contain modified amino acids other than the 20 gene-encoded amino acids.

As used herein, the term "aptamer" refer to relatively short RNA or DNA oligonucleotides, which binds to TRPV4 or activated β1 integrin, and preferably blocks/prevents/inhibits TRPV4 channel $Ca^{2+}$ influx or block activated β1 integrin signally events and cytoskeleton re-organization Methods of determining integrin activation are known in the art (see U.S. Patent publication No. 20080274482). "Aptamer" are isolated in vitro using, for example, the selection procedure known as SELEX (systematic evolution of ligands by exponential enrichment) (Tuerk & Gold, 1990; Ellington & Szostak, 1990, U.S. Pat. Nos. 5,475,096 and 5,270,163, which are incorporated herein by reference in their entirety). Because the selection procedure is driven by binding of ligands, aptamers bind their ligands with high affinity and fold into secondary structures which are optimized for ligand binding (Herman & Patel, 2000, incorporated herein by reference in its entirety). In this respect aptamers resemble antibodies by selectively binding corresponding ligand from complex chemical or biological mixtures. Methods to design and synthesize aptamers and aptamer binding sequences are known to those of skill in the art.

In one embodiment, the TRPV4 inhibitor inhibits an influx of calcium ions into the cell. In one embodiment, the inhibitor blocks the channel pore and prevents ion influx. In another embodiment, the inhibitor prevents the opening of channel pore. The detection, monitoring and measurement of cellular $Ca^{2+}$ influx can be performed using $Ca^{2+}$ sensitive chromophore e.g. FLUO-3, and FLUO-4 (INVITROGEN™ Inc.) as described herein. Such use of calcium indicators are well known to one skilled in the art.

In one embodiment, the TRPV4 inhibitor specifically inhibits the expression of TRPV4 in the cell. In one embodiment, the inhibitor is an RNA interference molecule specific to a TRPV4 gene such as an siRNA, shRNA, or dsRNA. The TRPV4 gene is preferably a mammalian TRPV4 gene.

As used herein, the term "gene" means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

The human TRPV4 gene is located on chromosome 12, location: 12q24.1, 108,705,277-108,755,595 reverse strand (ENSG00000111199) (Ensembl) assembled in Accession No. NC_000012.10 (SEQ. ID. No. 1; GENBANK™) Alternate gene names are OTRPC4;TRP12;VR-OAC;VRL-2; VRL2;VROAC. This gene encodes a member of the OSM9-like transient receptor potential channel (OTRPC) subfamily in the transient receptor potential (TRP) superfamily of ion channels. The encoded protein is a $Ca^{2+}$-permeable, nonselective cation channel that is thought to be involved in the regulation of systemic osmotic pressure. Two transcript variants encoding different isoforms have been found for this gene. Two transcripts of TRPV4 from this gene are NM_021625.3 (SEQ. ID. No. 2) and NM_147204.1 (SEQ. ID. No. 3) (GENBANK™)

Public access software programs and methods of predicting and selecting antisense oligonucleotides and siRNA are known in the art and are also found on the world wide web sites of GENSCRIPT™, AMBION®, DHARMACON™, OLIGOENGINE™, Wadsworth Bioinformatics Center, Whitehead Institute at the Massachusetts Institute of Technology and are also described in U.S. Pat. No. 6,060,248. After selecting the antisense oligonucleotides and siRNA sequences, these molecules can be produced biologically using an expression vector carrying the polynucleotides that encode the siRNA or antisense RNA. General molecular biological methods known in the art can be used to clone these sequences into the expression vectors. Examples of such are described herein.

In other embodiments, the siRNA TRPV4L molecules are [GCACACCGCCGUACCCUUAUU (sense) (SEQ. ID. No. 4), 5'-PUAAGGGUACGGCGGUGUGCUU (antisense) (SEQ. ID. No. 5], [GACCAAAUCUGCGCAUGAAUU (sense) (SEQ. ID. No. 6), 5'-PUUCAUGCGCAGAUUUGGUCUU (antisense) (SEQ. ID. No. 7)], [CAACCGGCCUAUCCUCUUUUU (sense) (SEQ. ID. No. 8), 5'-PAAAGAGGAUAGGCCGGUUGUU (antisense) (SEQ. ID. No. 9)], [GAACCCGUGUGCCAACAUGUU (sense) (SEQ. ID. No. 10), 5'-PCAUGUUGGCACACGGGUUCUU (antisense) (SEQ. ID. No. 11)]. These sense and anti-sense strand oligonucleotide can be chemically synthesized, annealed and formulated for use, e.g for direct intravitreal injection into an eye affected with macular degeneration or diabetic retinopathy. Alternatively, the anti-sense strand can be designed into short hairpin RNA (shRNA) for plasmid- or vector-based approaches for supplying siRNAs to cells to produce stable TRPV4 gene silencing. Examples of vectors for shRNA are #AM5779: -pSilencer™ 4.1-CMV neo; #AM5777: -pSilencer™ 4.1-CMV hygro; #AM5775: -pSilencer™ 4.1-CMV puro; #AM7209: -pSilencer™ 2.0-U6; #AM7210: -pSilencer™ 3.0-H1; #AM5768: -pSilencer™ 3.1-H1 puro; #AM5762: -pSilencer™ 2.1-U6 puro; #AM5770: -pSilencer™ 3.1-H1 neo; #AM5764: -pSilencer™ 2.1-U6 neo; #AM5766: -pSilencer™ 3.1-H1 hygro; #AM5760: -pSilencer™ 2.1-U6 hygro; #AM7207: -pSilencer™ 1.0-U6 (circular) from AMBION®.

Commercial pre-designed RNA interference molecules to TRPV4 are also available, e.g. from INVITROGEN™ Inc. (STEALTH™ Select RNAi, catalog #1299003, set of 3 Oligos; Oligo ID: HSS126973-5) and from DHARMACON™ (SMARTvector Lentiviral shRNA—Human TRPV4, catalog # SK-004195-00-10, set of 3 constructs). Human TRPV4 siRNA, shRNA and lentiviral particle gene silencers are available from Santa Cruz Biotechnology, Inc. catalog #s sc-61726, sc-61726-SH, and sc-61726-V respectively.

A reduction in the expression of TRPV4 in a cell can be determined by any methods known in the art, e.g. measurement of the messenger RNA by RT-PCR or by Western blots analysis for the protein as described herein. Commerical antibody to reactive against to TRPV4 protein are widely available, e.g. from ABCAM®, catalog #s ab39260 and ab62992.

In one embodiment, the TRPV4 inhibitor inhibits the phosphorylation of β1 integrin in the cell. A reduction in the phosphorylation of β1 integrin can be determined by any methods known in the art, e.g. by Western blots analysis for a phosphorylated epitope on β1 integrin, using an antibody specific for a phosphorylated epitope, such a, the 12G10 antibody specific for T788/789P as described herein.

In one embodiment, the TRPV4 inhibitor inhibits a phosphorylation and membrane translocation of a AKT protein in the cell. A reduction in the phosphorylation of AKT can be determined by any methods known in the art, e.g. by Western blots analysis for a phosphorylated AKT using antibody specific for a phosphorylated epitope on AKT, such as the antibody specific for Ser-473 in AKT as described herein.

For the avoidance of doubt, a reduction will be at least 5% relative to in the absence of a TRPV4 inhibitor, preferably at least 10%, 20%, 30%, 40%, 50%, 60%, 70%, 80%, 90%, or more, up to and including at least 100% or more, in the case of an increase, for example, at least 2×, 3×, 4×, 5×, . . . 10× or more). All the percentages in between 5-100% as well as fractions of integer number of folds increase are also included.

In one embodiment, the TRPV4 inhibitor comprises an antibody. In another embodiment, the TRPV4 inhibitor is an antibody.

In one embodiment, the antibody is specific for TRPV4. The binding of an anti-TRPV4 antibody or variant thereof inhibits the activation of the ion channel, for example be inhibiting channel opening or ion flux. Commercially antibodies to TRPV4 are available from MILIPORE®, INVITROGEN™, SIGMA ALDRICH® and R&D Systems to name a few. Alternatively, antibodies to TRPV4 can be made by methods well know to one skilled in the art. The antibodies to TRPV4 can be assayed for the inhibitory function by measuring the $Ca^{2+}$ influx in the presence and absence of mechanical strain as described herein, or in the presence and absence of a TRPV4 agonist, 4α-phorbol 12, 13-didecanoate.

In one embodiment, the antibody is specific for β1 integrin. In one embodiment, the TRPV4 inhibitor is a function-blocking antibody of β1 integrin, e.g. monoclonal antibody derived from clone P5D2. The binding of a function-blocking anti-β1 integrin antibody or variant thereof inhibits the downstream events of an activated β1 integrin, such as focal adhesion kinase (FAK)-mediated signaling by phosphorylation described in Nakayamada et. al. 2007 Arthritis Rheum. 56:1559-68. Other signaling pathways associated with β1 integrin activation include but are not limited to RhoA, Rac1, Ras, Raf, MEK, ERK, and JNK. Methods of assessing the activation of these pathways via integrins are well known in the art, e.g. in S Miyamoto, et. al. 1995, J. Cell Biol., 131: 791-805. Methods of assaying phosphorylation in signaling pathways are well known to one skilled in the art, e.g. Western blot analysis for phosphorylation at specific serine, threonine or tyrosine residues.

In one embodiment, provided herein is a method of inhibiting angiogenesis in a mammal in need thereof, the method comprises administering a therapeutically effective amount of an siRNA directed specifically against a TRPV4 gene and a pharmaceutically acceptable carrier.

In one embodiment, provided herein is a method of inhibiting angiogenesis in a mammal in need thereof, the method comprises administering a therapeutically effective amount of an antibody directed specifically against a β1 integrin and a pharmaceutically acceptable carrier, wherein the integrin function is blocked by the antibody.

In one embodiment, the mammal is afflicted with an angiogenesis-related disease or disorder.

In one embodiment, provided herein is a method for treatment of angiogenesis-related diseases in a mammal in need thereof, the method comprises administering a therapeutically effective amount of an siRNA directed specifically against a TRPV4 gene and a pharmaceutically acceptable carrier.

In one embodiment, provided herein is a method for treatment of angiogenesis-related diseases in a mammal in need thereof, the method comprises administering a therapeutically effective amount of an antibody directed specifically against a β1 integrin and a pharmaceutically acceptable carrier, wherein the integrin function is blocked by the antibody.

In one embodiment, the angiogenesis-related disease or disorder is selected from the group consisting of consisting of: cancer, macular degeneration; diabetic retinopathy; rheumatoid arthritis; Alzheimer's disease; obesity, psoriasis, atherosclerosis, vascular malformations, angiomata, and endometriosis.

In one embodiment, the treatment of angiogenesis-related diseases related to the eyes, e.g. macular degeneration or diabetic retinopathy, comprises directly injecting an siRNA, dsRNA, or shRNA vector directed against a TRPV4 gene into the vitreous cavity of the affected eye. In one embodiment, a mixture of several different siRNAs is injected directly into the vitreous cavity. In another embodiment, the siRNA can be combined with other anti-angiogenic therapy, such as anti-VEGF therapy, and injected directly into the vitreous cavity. In another embodiment, the siRNA can be combined with other TRPV4 inhibitors, e.g. an antibody P5D2, and injected directly into the vitreous cavity.

In some embodiments, the siRNA, dsRNA, or shRNA vector directed against TRPV4 gene is administered systemically, such as intravenously, e.g. via central venous catheter (CVC or central venous line or central venous access catheter) placed into a large vein in the neck (internal jugular vein), chest (subclavian vein) or groin (femoral vein). Methods of systemic delivery of siRNA, dsRNA, or shRNA vector are well known in the art, e.g. as described herein and in Mammoto T., et. al, 2007 (J. Biol. Chem., 282:23910-23918), Gao and Huang, 2008, (Mol. Pharmaceutics, Web publication December 30) and a review by Rossil, 2006, Gene Therapy, 13:583-584. The siRNA, dsRNA, or shRNA vector can be formulated in various ways, e.g. conjugation of a cholesterol moiety to one of the strands of the siRNA duplex for systemic delivery to the liver and jejunum (Soutschek J. et. al. 2004, Nature, 432:173-178), complexing of siRNAs to protamine fused with an antibody fragment for receptor-mediated targeting of siRNAs (Song E, et al. 2005, Nat Biotechnol., 23:

709-717) and the use of a lipid bilayer system by Morrissey et al. 2005 (Nat Biotechnol., 23: 1002-1007). The lipid bilayer system produces biopolymers that are in the 120 nanometer diameter size range, and are labeled as SNALPs, for Stable-Nucleic-Acid-Lipid-Particles. The lipid combination protects the siRNAs from serum nucleases and allows cellular endosomal uptake and subsequent cytoplasmic release of the siRNAs (see WO/2006/007712). These references are incorporated by reference in their entirety.

In other embodiment, the treatment of angiogenesis-related diseases related to the eyes, e.g. macular degeneration or diabetic retinopathy comprises directly injecting an antibody specifically against a β1 integrin function into the vitreous cavity of the eye, wherein the integrin function is blocked by the antibody. In one embodiment, the antibody in a monoclonal antibody derived from clone P5D2. In one embodiment, the antibody can be combined with other anti-angiogenic therapy, such as anti-VEGF therapy, and injected directly into the vitreous cavity. In another embodiment, the antibody can be combined with other TRPV4 inhibitors, e.g. an siRNA to TRPV4 as described herein, and injected directly into the vitreous cavity.

In some embodiments, the antibody specifically against a β1 integrin function is administered intravenously, e.g. via central venous catheter (CVC or central venous line or central venous access catheter) placed into a large vein in the neck (internal jugular vein), chest (subclavian vein) or groin (femoral vein). Systemic delivery of antibodies can be performed according to any methods known in the art, e.g. as described in Loberg et. al. 2007, Cancer Research 67:9417 and WO/2000/050008). These references are incorporated by reference in their entirety. The antibody or variants or fragments thereof can be formulated for systemic delivery such as in liposomes.

In one embodiments, the treatment of angiogenesis-related diseases having localized aberrant angiogenesis, e.g. solid non-metastatic tumor, arthritis, and endometriosis, comprises directly injecting an siRNA, dsRNA, or shRNA vector directed against a TRPV4 gene to the location or tissue with aberrant angiogenesis. In one embodiment, a mixture of several different siRNAs to TRPV4 is used, directly injected into the bodily site having localized aberrant angiogenesis. In another embodiment, the siRNA is combined with other anti-angiogenic therapy, such as anti-VEGF therapy, and injected directly into the bodily site. In another embodiment, the siRNA can be combined with other TRPV4 inhibitors, e.g. an antibody P5D2, and injected directly into the bodily site.

In other embodiments, the treatment of angiogenesis-related diseases having localized aberrant angiogenesis, e.g. solid non-metastatic tumor, arthritis, and endometriosis, comprises directly injecting an antibody specifically against a β1 integrin function into the location or tissue with aberrant angiogenesis, wherein the integrin function is blocked by the antibody. In one embodiment, the antibody in a monoclonal antibody derived from clone P5D2. In one embodiment, the antibody is combined with other anti-angiogenic therapy, such as anti-VEGF therapy, and injected directly into the bodily site having localized aberrant angiogenesis. In another embodiment, the antibody is combined with other TRPV4 inhibitors, e.g. an siRNA to TRPV4 as described herein, and injected directly into the bodily site.

In other embodiments, the treatment of angiogenesis-related diseases comprises systemic administration of an siRNA, dsRNA, shRNA vector directed against a TRPV4 gene and/or an antibody specifically against a β1 integrin function into the mammal in need thereof. Such a mammal would have been diagnosed with an angiogenesis-related disease or disorder by a skilled physician.

In one embodiment, the methods described herein can be administered in conjunction with other anti-angiogenesis factor/drugs and treatment regime for the afflicted mammals, such as chemotherapy and radiation therapy.

As used herein, the term "a therapeutically effective amount" refers an amount sufficient to achieve the intended purpose. For example, an effective amount of a TRPV4 inhibitor that inhibits angiogenesis will cause a reduction or even completely halt any new blood vessel formation. An effective amount for treating or ameliorating a disorder, disease, or medical condition is an amount sufficient to result in a reduction or complete removal of the symptoms of the disorder, disease, or medical condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

In one embodiment, the endothelial cell is a mammalian endothelial cell. In another embodiment, the endothelial cell is a human endothelial cell.

Mammals include but are not limited to human, cat, dog, horse, monkey, cow, sheep, goats and other ungulates.

In one embodiment, the mammal is a human.

Integrins as Mechanoreceptors

Cells within solid tissues sense mechanical forces caused by physical distortion of the extracellular matrix (ECM) scaffolds that hold cells together and form the physical supporting framework of living tissues. Cell surface receptors that support ECM adhesion might function as mechanoreceptors and mediate cellular mechanosensation. Integrins, which are the most ubiquitous ECM receptors, are heterodimeric transmembrane proteins consisting of α and β chains. Their extracellular domain binds to ligands present in the ECM that contain specific peptide sequences, such as the arg-gly-asp (RGD) sequence from the cell-binding region of fibronectin. Integrins undergo conformational changes in response to ligand occupancy that result in receptor 'activation' and initiation of downstream signaling responses in the absence of external mechanical loads. For example, unbound (inactive) integrins do not form focal adhesions, whereas integrin ligation as a result of cell binding to ECM proteins, synthetic RGD peptides, or activating anti-integrin antibodies induces changes in integrin conformation that activate the small GTPase Rho and promote 'focal adhesion' formation. Focal adhesions are multi-molecular protein complexes that mechanically anchor the short cytoplasmic tails of integrins to the cytoskeleton; they also serve as orienting scaffolds for various signaling transducing molecules. Because integrins form a relatively stiff connection between the ECM and the cytoskeleton, they provide a preferred path for mechanical force transfer across the cell surface. Importantly, while force application to bound (already activated) integrins alters the activity of many signaling molecules inside adherent cells, including small GTPases (e.g., Rho, Rac), protein kinases (e.g., FAK, Fyn, Src), and cAMP, application of similar forces to unligated integrins (i. e., through bound non-activating anti-β1 integrin antibodies) fails to produce focal adhesion formation or induce these signaling responses. Thus, activated integrins function to focus and concentrate mechanical stresses at focal adhesions where forces are transferred to molecular partners of integrins that elicit changes in chemical activities milliseconds to minutes after force application.

Integrins and Stress-Activated (SA) Ion Channels

One of the most ubiquitous and rapid mechanosensing mechanisms used by cells involves force-induced activation of SA ion channels on the cell surface. Some of these molecules, such as members of the Transient Receptor Potential (TRP) family of mechanically-gated ion channels can be triggered to alter calcium transport as a result of physical distortion of the lipid bilayer and resulting stress transfer to the channel. For example, the activation of calcium influx by fluid shear stress in kidney epithelial cells is mediated by interactions between two members of the TRP family of mechanoregulated ion channels, polycystin-1 and polycystin-2, that colocalize with microtubules within the primary cilium. Other types of SA channels, such as SAKcaC, also have been identified in mammalian cells that are activated within milliseconds after mechanical stress is applied to the cell's surface membrane (e.g., as analyzed in patch-clamp experiments). Therefore, mechanosignaling through SA channels is often viewed as a mechanism that is independent of integrin-based mechanosensation. However, forces that are channeled through transmembrane integrins to the cytoskeleton also can specifically activate certain SA channels. For example, many mechanosensitive ion channels lose their normal regulated activities (and become super-activated) if the lipid bilayer is separated from the underlying cortical cytoskeleton, and certain types of TRP channels, such as TRPV2 and TRPV4, may bind directly to microtubules or actin filaments through ankyrin repeats within their cytoplasmic domains. Interestingly, ankyrin domains in integrin-linked kinase (ILK) mediate its association with integrins via PINCH protein; this raises the possibility that TRP channels may associate with integrins through other cytoskeletal-associated adapter proteins present within focal adhesions. This is supported by the recent finding that enhanced osmotransduction in cultured nociceptors is mediated by TRPV4, and requires signaling through integrins and Src in dorsal root ganglia. In contrast, the finding that amphipathic molecules that intercalate in the lipid bilayer, such as chlorpromazine and trinitrophenol, alter the activity of certain SA channels intimates that they are directly activated by membrane bilayer distortion; however, these lipidmodifying molecules also can alter cytoskeletal mechanics in certain cells. Moreover, the SA channel SAKcaC contains a 59 amino acid long cytoplasmic STREX domain which when deleted attenuates amphipath-induced SA activity; thus, a submembranous adapter protein appears to mediate force transmission from membrane lipids to this channel. Importantly, integrins also have been shown to co-localize and coimmunoprecipitate with members of the ENaC channel family and polycystin-1. In the neuromuscular junction, stimulation of muscle cell contraction triggers calcium influx within 100 msec at the synapse, and this response can be prevented by adding inhibitors of integrin binding. Both a rapid millisecond calcium influx response and a slower wave of calcium influx on the order of seconds to minutes also can be produced by applying force directly to cell surface integrins, whereas application of the same force to other transmembrane receptors is less effective at eliciting this response.

Integrins are a large family of proteins with 8 known α and 18 β subunits that combine to form distinct dimeric transmembrane receptors. There has been extensive investigation into the function of the various domains of the α and β integrin chains. The extracellular domains of both subunits contribute to binding of specific adhesive ligands; however, the α and β integrin cytoplasmic tails, which are relatively short, appear to interact independently with intracellular proteins. The α subunits are poorly conserved with the exception of a small domain near the membrane, whereas the β subunits are much more homologous. Although α integrins can bind focal adhesion proteins, most known cytoskeletal interactions occur through the β integrin chains, and the majority of integrin signaling is mediated by β integrins.

Transient Receptor Potential (TRP) Channels

TRP channels comprise a large family of cation channels that provide a pathway for calcium influx into cells. Among the ~30 TRP-channel proteins identified in mammals, endothelial cells express ~20 members that are classified into six subfamilies: canonical (TRPC), vanilloid (TRPV), melastatin (TRPVM), polycystin (TRPP), mucolipin (TRPML) and TRPA. Structurally, TRP channels consist of six transmembrane (TM)-spanning helices with a pore region between TM5 and and cytoplasmic N and C termini. Both TRPC and TRPV channels contain multiple anykyrin domains at their N-terminus that are absent in TRPM channels. Most of the TRP channels contain PDZ binding motifs and recognition sites for PKC and PI3K. TRPC subfamily channels that are ubiquitously expressed in endothelial cells are responsible for store-operated or receptor-mediated calcium entry; they also have been implicated in control of endothelial barrier function and vasorelaxation. Among the vertebrate TRPV and TRPM channels, TRPV4 and TRPV2 are considered mechanosensitive, and growing evidence suggests that TRPV4 plays critical role in mechanical force-induced regulation of endothelial cell function. For example, in endothelial cells, TRPV4 acts as a calcium entry channel that is activated by increases in cell volume and temperature. TRPV4 can also be activated by ligands such as arachidonic acid and its metabolites, endocannabinoids and a synthetic phorbol ester, 4-α-phorbol 12, 13-didecanoate (PPD), and it can be suppressed by integrin and Src kinase inhibitors during osmotransduction in dorsal root ganglia. In the present invention with sensitive calcium imaging (FLUO4-based) methods, it was found that force application to integrins activates calcium influx within 5 to 50 msec in CE cells that can be inhibited by treatment with the SA channel inhibitor gadolinium chloride, or by suppressing expression of TRPV4, but not TRPV2, using siRNA. Moreover, this response requires physical distortion (strain) of integrin-cytoskeleton linkages in the cytoplasm directly beneath the site of mechanical stress application, and single chain integrin chimeras that only contain the cytoplasmic tail of integrin can support force-induced calcium influx. In addition, the inventors also showed that GFP-TRPV4 is recruited to focal adhesions that form when cells bind to magnetic microbeads coated with integrin ligands. Taken together, these data indicate that force application to transmembrane integrin receptors results in almost immediate activation of SA channels on the cell surface as a result of distortion of the supramolecular lattice that links the cytoplasmic portions of integrins to TRPV4 channels within the focal adhesion.

Generation of Recombinant TRPV4 or Activated β1 Integrin Proteins

In some embodiment, TRPV4 or function-blocking β1 integrin antibodies can be generated by any methods known in the art, for example, immunizing a mammal with TRPV4 or activated β1 integrin proteins. Large quantities of such proteins can be made using standard molecular recombinant protein expression methods. Protein coding nucleic acid sequences of TRPV4 or β1 integrin protein or fragments thereof can be amplified by polymerase chain reaction (PCR) and cloned into protein expression vectors. In humans, there are six isoform of β1 integrin mRNA (GENBANK™ Accession Nos. NM_002211.3, NM_033666.2, NM_033667.2, NM_033668.2, NM_033669.2, NM_133376.2). In humans, there are two isoform of TRPV4 mRNA (GENBANK™ Accession Nos. NM_021625 and NM_147204). The resultant expression vectors can be then be transfected into corresponding host for protein expression.

Examples of expression vectors and host cells are the pET vectors (NOVAGEN®), pGEX vectors (GE Life Sciences), and pMAL vectors (New England labs. Inc.) for protein expression in *E. coli* host cell such as BL21, BL21(DE3) and AD494(DE3)pLysS, Rosetta (DE3), and Origami(DE3) ((NOVAGEN®); the strong CMV promoter-based pcDNA3.1 (INVITROGEN™ Inc.) and pClneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (CLONTECH®), pAd/CMV/V5-DEST, pAd-DEST vector (INVITROGEN™ Inc.) for adenovirus-mediated gene transfer and expression in mammalian cells; pLNCX2, pLXSN, and pLAPSN retrovirus vectors for use with the RETRO-X™ system from Clontech for retroviral-mediated gene transfer and expression in mammalian cells; pLenti4/V5-DEST™, pLenti6/V5-DEST™, and pLenti6.2/V5-GW/lacZ (INVITROGEN™ Inc.) for lentivirus-mediated gene transfer and expression in mammalian cells; adenovirus-associated virus expression vectors such as pAAV-MCS, pAAV-IRES-hrGFP, and pAAV-RC vector (STRATAGENE®) for adeno-associated virus-mediated gene transfer and expression in mammalian cells; BACpak6 baculovirus (CLONTECH®) and pFastBac™ HT (INVITROGEN™ Inc.) for the expression in *Spodopera frugiperda* 9 (Sf9) and Sf11 insect cell lines; pMT/BiP/V5-His (INVITROGEN™ Inc.) for the expression in *Drosophila schneider* S2 cells; *Pichia* expression vectors pPICZα, pPICZ, pFLDα and pFLD (INVITROGEN™ Inc.) for expression in *Pichia pastoris* and vectors pMETα and pMET for expression in *P. methanolica*; pYES2/GS and pYD1 (INVITROGEN™ Inc.) vectors for expression in yeast *Saccharomyces cerevisiae*. Recent advances in the large scale expression heterologous proteins in *Chlamydomonas reinhardtii* are described by Griesbeck C. et. al. 2006 Mol. Biotechnol. 34:213-33 and Fuhrmann M. 2004, Methods Mol Med. 94:191-5. Foreign heterologous coding sequences are inserted into the genome of the nucleus, chloroplast and mitochodria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. Biolistic gene gun method is used to introduced the vector in the algae. Upon its entry into chloroplasts, the foreign DNA is released from the gene gun particles and integrates into the chloroplast genome through homologous recombination.

In one embodiment, the expression vector is a viral vector, such as a lentivirus, adenovirus, or adeno-associated virus. A simplified system for generating recombinant adenoviruses is presented by He T C. et. al. Proc. Natl. Acad. Sci. USA, 95:2509-2514, 1998. The gene of interest is first cloned into a shuttle vector, e.g. pAdTrack-CMV. The resultant plasmid is linearized by digesting with restriction endonuclease Pme I, and subsequently cotransformed into *E. coli* BJ5183 cells with an adenoviral backbone plasmid, e.g. pAdEasy-1 of STRATAGENE®'s ADEASY™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenovirus are generated within the HEK 293 cells.

In one embodiment, the preferred viral vector is a lentiviral vector and there are many examples of use of lentiviral vectors for gene therapy for inherited disorders of haematopoietic cells and various types of cancer, and these references are hereby incorpaorated by reference (Klein, C. and Baum, C. (2004), Hematol. J., 5:103-111; Zufferey, R et. al. (1997), Nat. Biotechnol., 15:871-875; Morizono, K. et. al. (2005), Nat. Med., 11:346-352; Di Domenico, C. et. al. (2005). Hum. Gene Ther., 16:81-90). The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with VIRAPOWER™ Lentiviral Expression systems from INVITROGEN™ Inc.

In one embodiment, the expression viral vector can be a recombinant adeno-associated virus (rAAV) vector. Using rAAV vectors, genes can be delivered into a wide range of host cells including many different human and non-human cell lines or tissues. Because AAV is non-pathogenic and does not illicit an immune response, a multitude of pre-clinical studies have reported excellent safety profiles. rAAVs are capable of transducing a broad range of cell types and transduction is not dependent on active host cell division. High titers, >$10^8$ viral particle/ml, are easily obtained in the supernatant and $10^{11}$-$10^{12}$ viral particle/ml with further concentration. The transgene is integrated into the host genome so expression is long term and stable.

The use of alternative AAV serotypes other than AAV-2 (Davidson et al (2000), PNAS 97(7)3428-32; Passini et al (2003), J. Virol 77(12):7034-40) has demonstrated different cell tropisms and increased transduction capabilities. With respect to brain cancers, the development of novel injection techniques into the brain, specifically convection enhanced delivery (CED; Bobo et al (1994), PNAS 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying the chimeric DNA coding sequence, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12;71-6; Summerford, C. and R. Samulski, 1998, J. Virol. 72:1438-45; Summerford, C. and R. Samulski, 1999, Nat. Med. 5: 587-88). AAV2/1 and AAV2/5 vectors are currently purified by three sequential CsCl gradients.

Generating TRPV4 and Function-Blocking Anti-β1 Integrin Antibodies

As used herein, the term "antibody" refers to immunoglobulin molecules and immunologically active portions of immunoglobulin molecules, i.e., molecules that contain an antigen binding site that immunospecifically binds an antigen. The terms also refers to antibodies comprised of two immunoglobulin heavy chains and two immunoglobulin light chains as well as a variety of forms besides antibodies; including, for example, Fv, Fab, and $F(ab)'_2$ as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2nd ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference.).

In one embodiment, the TRPV4 or function-blocking anti-β1 integrin antibody is a polyclonal antibody. In one embodiment, theTRPV4 or function-blocking anti-β1 integrin antibody is a monoclonal antibody. In preferred embodiment, theTRPV4 or function-blocking anti-β1 integrin antibody is a humanized antibody. In preferred another embodiment theTRPV4 or function-blocking anti-β1 integrin antibody is a chimeric antibody. In yet another embodiment, the TRPV4 or function-blocking anti-β1 integrin antibodies include, but are not limited to multispecific, human, single chain antibodies, Fab fragments, $F(ab)'_2$ fragments, fragments produced by a Fab expression library, domain-deleted antibodies (including, e.g., CH2 domain-deleted antibodies), anti-idiotypic (anti-Id) antibodies (including, e.g., anti-Id antibodies to antibodies of the invention), and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Encompassed in the methods disclosed herein are TRPV4 or function-blocking anti-β1 integrin antibodies that are, but are not limited to, engineered forms of antibodies and antibody fragments such as diabodies, triabodies, tetrabodies, and higher multimers of scFvs, single-domain antibodies, as well as minibodies, such as two scFv fragments joined by two constant (C) domains. See, e.g., Hudson, P. J. and Couriau, C., Nature Med. 9: 129-134 (2003); U.S. Publication No. 20030148409; U.S. Pat. No. 5,837,242.

In one embodiment, the TRPV4 or function-blocking anti-β1 integrin antibodies can be obtained from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

In a preferred embodiment for use in humans, the TRPV4 or function-blocking anti-β1 integrin antibodies are human or humanized antigen-binding antibody fragments of the present invention and include, but are not limited to, Fab, Fab and $F(ab)'_2$, Fd, single-chain Fvs (scFv), single-domain antibodies, triabodies, tetrabodies, minibodies, domain-deleted antibodies, single-chain antibodies, disulfide-linked Fvs (sdFv) and fragments comprising either a variable light chain (VL) or variable heavy chain VH region. Antigen-binding antibody fragments, including single-chain antibodies, may comprise the variable region(s) alone or in combination with the entirety or a portion of the following: hinge region, CHI, CH2, and CH3 domains. Also included in the invention are antigen-binding fragments also comprising any combination of variable region(s) with a hinge region, CH1, CH2, and CH3 domains.

Preferred antibodies in the therapeutic methods of the invention are those containing a deletion of the CH2 domain.

As used herein, the term "humanized" immunoglobulin or "humanized" antibody refers to an immunoglobulin comprising a human framework, at least one complementarity determining regions (CDR) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. For example, a humanized immunoglobulin would not encompass a chimeric mouse variable region/human constant region antibody.

As used herein, the term "framework region" refers to those portions of antibody light and heavy chain variable regions that are relatively conserved (i.e., other than the CDRs) among different immunoglobulins in a single species, as defined by Kabat, et al., op. cit. As used herein, a "human framework region" is a framework region that is substantially identical (about 85% or more) to the framework region of a naturally occurring human antibody.

As used herein, the term "chimeric" antibody refers to an antibody whose heavy and light chains have been constructed, typically by genetic engineering, from immunoglobulin gene segments belonging to different species. For example, the variable (V) segments of the genes from a mouse monoclonal antibody may be joined to human constant (C) segments, such as gammal and/or gamma4. A typical therapeutic or diagnostic chimeric antibody is thus a hybrid protein comprising at least one V region (e.g., VH or VL) or the entire antigen-binding domain (i.e., VH and VL) from a mouse antibody and at least one C (effector) region (e.g., CH (CH1, CH2, CH3, or CH4) or CL or the entire C domain (i.e., CH and CL) from a human antibody, although other mammalian species may be used. In some embodiments, especially for use in the therapeutic methods of the TRPV4 or function-blocking anti-β1 integrin antibodies should contain no CH2 domain.

In one embodiment, a chimeric antibody may contain at least the TRPV4 or function-blocking anti-β1 integrin antigen binding Fab or $F(ab)'_2$ region while the humanized antibody can contain at least the TRPV4 or function-blocking anti-β1 integrin antigen binding Fv region fused to a human Fc region.

The terms "antigen" is well understood in the art and refer to the portion of a macromolecule which is specifically recognized by a component of the immune system, e.g., an antibody or a T-cell antigen receptor. The term antigen includes any protein determinant capable of specific binding to an immunoglobulin. Antigenic determinants usually consist of chemically active surface groupings of molecules such as amino acids or sugar side chains and usually have specific three dimensional structural characteristics, as well as specific charge characteristics.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

Recombinant expression of an antibody disclosed herein, or fragment, derivative or analog thereof, (e.g., a heavy or light chain of an antibody of the invention or a single chain antibody of the invention), including a recombinant protein derived from the antibody antigen-binding region, requires construction of an expression vector containing a polynucleotide that encodes the antibody. Once a polynucleotide encoding an antibody molecule or a heavy or light chain of an antibody or portion thereof (preferably containing the heavy or light chain variable domain) of the invention has been obtained, the vector for the production of the antibody molecule may be produced by recombinant DNA technology using techniques well known in the art. Thus, methods for preparing a protein by expressing a polynucleotide containing an antibody-encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT publication WO 86/05807; PCT publication WO 89/01036; and U.S. Pat. No. 5,122,464) and the variable domain of the antibody may be cloned into such a vector for expression of the entire heavy or light chain. Methods for generating multivalent and bispecific antibody fragments are described by Tomlinson I. and Holliger P. (2000) Methods Enzymol, 326, 461-479 and the engineering of antibody fragments and the rise of single-domain antibodies is described by Holliger P. (2005) Nat. Biotechnol. September; 23(9):1126-36, and are both hereby incorporated by reference.

Inhibition of TRPV4 Expression

In one embodiment, the expression of TRPV4 is inhibited by an RNA interference molecule.

RNA interference-inducing molecules include but are not limited to siRNA, dsRNA, stRNA, shRNA, micro RNAi (mRNAi), antisense oligonucleotides etc. and modified versions thereof, where the RNA interference molecule silences the gene expression of TRPV4. An anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like.

RNA interference (RNAi) is an evolutionally conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease can be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand can precede the nucleotide loop structure and the antisense strand can follow. These shRNAs can be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety).

The target gene or sequence of the RNA interfering agent can be a cellular gene or genomic sequence, e.g. the TRPV4 (genomic sequence ENSG00000111199 (Ensembl) assembled in GENBANK™ Accession No. NC_000012.10 (SEQ. ID. No. 1), NM_021625.3 (SEQ. ID. No. 2) and NM_147204.1 (SEQ. ID. No. 3)). An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al, Nature Biotechnology 6:635-637, 2003. In addition to expression profiling, one can also screen the potential target sequences for similar sequences in the sequence databases to identify potential sequences which can have off-target effects. For example, according to Jackson et al. (Id.) 15, or perhaps as few as 11 contiguous nucleotides of sequence identity are sufficient to direct silencing of non-targeted transcripts. Therefore, one can initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. For example, siRNA containing D-arabinofuranosyl structures in place of the naturally-occurring D-ribonucleosides found in RNA can be used in RNAi molecules according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotidesmolecules similar to the oligonucleotides containing 2'-O-methyl ribose, arabinose and particularly D-arabinose (U.S. Pat. No. 5,177,196).

The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

siRNA and miRNA molecules having various "tails" covalently attached to either their 3'- or to their 5'-ends, or to both, are also known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

siRNAs useful for the methods described herein include siRNA molecules of about 15 to about 40 or about 15 to about 28 nucleotides in length, which are homologous to the TRPV4 gene. Preferably, the TRPV4 targeting siRNA molecules have a length of about 19 to about 25 nucleotides. More preferably, the targeting siRNA molecules have a length of about 19, 20, 21, or 22 nucleotides. The targeting siRNA molecules can also comprise a 3' hydroxyl group. The targeting siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the TRPV4 targeting RNA molecule has a 3' overhang from about 0 to about 6 nucleotides (e.g., pyrimidine nucleotides, purine nucleotides) in length. In other embodiments, the 3' overhang is from about 1 to about 5 nucleotides, from about 1 to about 3 nucleotides and from about 2 to about 4 nucleotides in length. In one embodiment the targeting RNA molecule is double stranded—one strand has a 3' overhang and the other strand can be blunt-ended or have an overhang. In the embodiment in which the targeting RNA molecule is double stranded and both strands comprise an overhang, the length of the overhangs can be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

Oligonucleotide Modifications

Unmodified oligonucleotides may be less than optimal in some applications, e.g., unmodified oligonucleotides can be prone to degradation by e.g., cellular nucleases. Nucleases can hydrolyze nucleic acid phosphodiester bonds. However, chemical modifications to one or more of the subunits of oligonucleotide can confer improved properties, and, e.g., can render oligonucleotides more stable to nucleases.

Modified nucleic acids and nucleotide surrogates can include one or more of:

(i) alteration, e.g., replacement, of one or both of the non-linking phosphate oxygens and/or of one or more of the linking phosphate oxygens in the phosphodiester backbone linakge.

(ii) alteration, e.g., replacement, of a constituent of the ribose sugar, e.g., of the 2' hydroxyl on the ribose sugar;

(iii) wholesale replacement of the phosphate moiety with "dephospho" linkers;

(iv) modification or replacement of a naturally occurring base with a non-natural base;

(v) replacement or modification of the ribose-phosphate backbone;

(vi) modification of the 3' end or 5' end of the oligonucelotide, e.g., removal, modification or replacement of a terminal phosphate group or conjugation of a moiety, e.g., a fluorescently labeled moiety, to either the 3' or 5' end of oligonucleotide; and (vii) modification of the sugar (e.g., six membered rings).

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

As oligonucleotides are polymers of subunits or monomers, many of the modifications described herein can occur at a position which is repeated within an oligonucleotide, e.g., a modification of a nucleobase, a sugar, a phosphate moiety, or the non-bridging oxygen of a phosphate moiety. It is not necessary for all positions in a given oligonucleotide to be uniformly modified, and in fact more than one of the aforementioned modifications may be incorporated in a single oligonucleotide or even at a single nucleoside within an oligonucleotide.

In some cases the modification will occur at all of the subject positions in the oligonucleotide but in many, and in fact in most cases it will not. By way of example, a modification may only occur at a 3' or 5' terminal position, may only occur in the internal region, may only occur in a terminal regions, e.g. at a position on a terminal nucleotide or in the last 2, 3, 4, 5, or 10 nucleotides of an oligonucleotide. A modification may occur in a double strand region, a single strand region, or in both. A modification may occur only in the double strand region of an oligonucleotide or may only occur in a single strand region of an oligonucleotide. E.g., a phosphorothioate modification at a non-bridging oxygen position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. The 5' end or ends can be phosphorylated.

A modification described herein may be the sole modification, or the sole type of modification included on multiple nucleotides, or a modification can be combined with one or more other modifications described herein. The modifications described herein can also be combined onto an oligonucleotide, e.g. different nucleotides of an oligonucleotide have different modifications described herein.

In some embodiments it is particularly preferred, e.g., to enhance stability, to include particular nucleobases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Specific Modifications to Oligonucleotide

The Phosphate Group

The phosphate group is a negatively charged species. The charge is distributed equally over the two non-bridging oxygen atoms. However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. In certain embodiments, one of the non-bridging phosphate oxygen atoms in the phosphate backbone moiety can be replaced by any of the following: S, Se, $BR_3$ (R is hydrogen, alkyl, aryl), C (i.e. an alkyl group, an aryl group, etc . . . ), H, $NR_2$ (R is hydrogen, alkyl, aryl), or OR (R is alkyl or aryl). The phosphorous atom in an unmodified phosphate group is achiral. However, replacement of one of the non-bridging oxygens with one of the above atoms or groups of atoms renders the phosphorous atom chiral; in other words a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotides diastereomers. Thus, while not wishing to be bound by theory, modifications to both non-bridging oxygens, which eliminate the chiral center, e.g. phosphorodithioate formation, may be desirable in that they cannot produce diastereomer mixtures. Thus, the non-bridging oxygens can be independently any one of S, Se, B, C, H, N, or OR (R is alkyl or aryl).

The phosphate linker can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon is preferred. When the bridging oxygen is the 5'-oxygen of a nucleoside, replacement with nitrogen is preferred.

Replacement of the Phosphate Group

The phosphate group can be replaced by non-phosphorus containing connectors. While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Modified phosphate linkages where at least one of the oxygens linked to the phosphate has been replaced or the phosphate group has been replaced by a non-phosphorous group, are also referred to as "non-phosphodiester backbone linkage."

Replacement of Ribophosphate Backbone

Oligonucleotide-mimicking scaffolds can also be constructed wherein the phosphate linker and ribose sugar are replaced by nuclease resistant nucleoside or nucleotide surrogates. While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone. Examples include the morpholino, cyclobutyl, pyrrolidine and peptide nucleic acid (PNA) nucleoside surrogates. A preferred surrogate is a PNA surrogate.

Sugar Modifications

An oligonucleotide can include modification of all or some of the sugar groups of the nucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino,or diheteroaryl amino), —NHC(O)R (R=alkyl, cycloalkyl, aryl, aralkyl, heteroaryl or sugar), cyano; mercapto; alkyl-thio-alkyl; thioalkoxy; thioalkyl; and alkyl, cycloalkyl, aryl, alkenyl and alkynyl, which may be optionally substituted with e.g., an amino functionality.

The sugar group can also contain one or more carbons that possess the opposite stereochemical configuration than that of the corresponding carbon in ribose. Thus, an oligonucleotide can include nucleotides containing e.g., arabinose, as the sugar. The monomer can have an alpha linkage at the 1' position on the sugar, e.g., alpha-nucleosides. Oligonucleotides can also include "abasic" sugars, which lack a nucleobase at C-1'. These abasic sugars can also be further containing modifications at one or more of the constituent sugar atoms. Oligonucleotides can also contain one or more sugars that are in the L form, e.g. L-nucleosides.

Preferred substitutents are 2'-O-Me (2'-O-methyl), 2'-O-MOE (2'-O-methoxyethyl), 2'-F, 2'-O-[2-(methylamino)-2-oxoethyl] (2'-O—NMA), 2'-S-methyl, 2'-O—CH2-(4'-C) (LNA), 2'-O—CH2CH2-(4'-C) (ENA), 2'-O-aminopropyl (2'-O-AP), 2'-O-dimethylaminoethyl (2'-O-DMAOE), 2'-O-dimethylaminopropyl (2'-O-DMAP) and 2'-O-dimethylaminoethyloxyethyl (2'-O-DMAEOE).

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs).

When a linker/phosphate-functional molecular entity-linker/phosphate array is interposed between two strands of a dsRNA, this array can substitute for a hairpin RNA loop in a hairpin-type RNA agent.

Terminal modifications useful for modulating activity include modification of the 5' end with phosphate or phosphate analogs. E.g., in preferred embodiments antisense strands of dsRNAs, are 5' phosphorylated or include a phosphoryl analog at the 5' prime terminus. 5'-phosphate modifications include those which are compatible with RISC mediated gene silencing. Modifications at the 5'-terminal end can also be useful in stimulating or inhibiting the immune system of a subject. Suitable modifications include: 5'-monophosphate ((HO)2(O)P—O-5'); 5'-diphosphate ($(HO)_2(O)$P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-beta-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'-). Other embodiments include replacement of oxygen/sulfur with $BH_3$, $BH_3$— and/or Se.

Terminal modifications can also be useful for monitoring distribution, and in such cases the preferred groups to be added include fluorophores, e.g., fluorscein or an ALEXA® dye, e.g., ALEXA® 488. Terminal modifications can also be useful for enhancing uptake, useful modifications for this include cholesterol. Terminal modifications can also be useful for cross-linking an RNA agent to another moiety; modifications useful for this include mitomycin C.

Nucleobases

Adenine, guanine, cytosine and uracil are the most common bases found in RNA. These bases can be modified or replaced to provide RNA's having improved properties. For example, nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-(halo)adenine, 2-(alkyl)adenine, 2-(propyl)adenine, 2 (amino)adenine, 2-(aminoalkyll) adenine, 2 (aminopropyl)adenine, 2 (methylthio) $N^6$ (isopentenyl)adenine, 6 (alkyl)adenine, 6 (methyl)adenine, 7 (deaza) adenine, 8 (alkenyl)adenine, 8-(alkyl)adenine, 8 (alkynyl) adenine, 8 (amino)adenine, 8-(halo)adenine, 8-(hydroxyl) adenine, 8 (thioalkyl)adenine, 8-(thiol)adenine, $N^6$-(isopentyl)adenine, $N^6$ (methyl)adenine, $N^6$, $N^6$ (dimethyl) adenine, 2-(alkyl)guanine,2 (propyl)guanine, 6-(alkyl) guanine, 6 (methyl)guanine, 7 (alkyl)guanine, 7 (methyl) guanine, 7 (deaza)guanine, 8 (alkyl)guanine, 8-(alkenyl) guanine, 8 (alkynyl)guanine, 8-(amino)guanine, 8 (halo) guanine, 8-(hydroxyl)guanine, 8 (thioalkyl)guanine, 8-(thiol) guanine, N (methyl)guanine, 2-(thio)cytosine, 3 (deaza) 5 (aza)cytosine, 3-(alkyl)cytosine, 3 (methyl)cytosine, 5-(alkyl)cytosine, 5-(alkynyl)cytosine, 5 (halo)cytosine, 5 (methyl)cytosine, 5 (propynyl)cytosine, 5 (propynyl)cytosine, 5 (trifluoromethyl)cytosine, 6-(azo)cytosine, N4 (acetyl)cytosine, 3 (3 amino-3 carboxypropyl)uracil, 2-(thio) uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5 (methylaminomethyl)-2,4 (dithio)uracil, 5 (2-aminopropyl)uracil, 5-(alkyl)uracil, 5-(alkynyl)uracil, 5-(allylamino)uracil, 5 (aminoallyl)uracil, 5 (aminoalkyl)uracil, 5 (guanidiniumalkyl)uracil, 5 (1,3-diazole-1-alkyl) uracil, 5-(cyanoalkyl)uracil, 5-(dialkylaminoalkyl)uracil, 5 (dimethylaminoalkyl)uracil, 5-(halo)uracil, 5-(methoxy) uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo)uracil, dihydrouracil, N3 (methyl)uracil, 5-uracil (i.e., pseudouracil), 2 (thio)pseudouracil,4 (thio)pseudouracil,2,4-(dithio)psuedouracil,5-(alkyl)pseudouracil, 5-(methyl) pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio) pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio) pseudouracil, 1 (aminocarbonylethylenyl)-pseudouracil, 1 (aminocarbonylethylenyl)-2(thio)-pseudouracil, 1 (aminocarbonylethylenyl)-4 (thio)pseudouracil, 1 (aminocarbonylethylenyl)-2,4-(dithio)pseudouracil, 1 (aminoalkylaminocarbonylethylenyl)-pseudouracil, 1 (aminoalkylaminocarbonylethylenyl)-2(thio)-pseudouracil, 1 (aminoalkylaminocarbonylethylenyl)-4 (thio)pseudouracil, 1 (aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino)purine, 5 substituted pyrimidines, $N^2$-substituted purines, $N^6$-substituted purines, $O^6$-substituted purines, substituted 1,2,4-triazoles, or any O-alkylated or N-alkylated derivatives thereof;

Further purines and pyrimidines include those disclosed in U.S. Pat. No. 3,687,808, hereby incorporated by refernence, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Cationic Groups

Modifications to oligonucleotides can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid); or $NH(CH_2CH_2NH)_nCH_2CH_2$-AMINE (AMINE=$NH_2$; alkylamino, dialkylamino, heterocyclyl, arylamino, diaryl amino, heteroaryl amino,or diheteroaryl amino).

Placement Within an Oligonucleotide

Some modifications may preferably be included on an oligonucleotide at a particular location, e.g., at an internal position of a strand, or on the 5' or 3' end of an oligonucleotide. A preferred location of a modification on an oligonucleotide, may confer preferred properties on the agent. For example, preferred locations of particular modifications may confer optimum gene silencing properties, or increased resistance to endonuclease or exonuclease activity.

One or more nucleotides of an oligonucleotide may have a 2'-5' linkage. One or more nucleotides of an oligonucleotide may have inverted linkages, e.g. 3'-3', 5'-5', 2'-2' or 2'-3' linkages.

An oligonucleotide may comprise at least one 5'-pyrimidine-purine-3' (5'-PyPu-3') dinucleotide wherein the pyrimidine is modified with a modification chosen independently from a group consisting of 2'-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—$CH_2$-(4'-C) (LNA) and 2'-O—$CH_2CH_2$-(4'-C) (ENA).

In one embodiment, the 5'-most pyrimidines in all occurrences of sequence motif 5'-pyrimidine-purine-3' (5'-PyPu-3') dinucleotide in the oligonucleotide are modified with a modification chosen from a group consisting of 2"-O-Me (2'-O-methyl), 2'-O-MOE (2'-O-methoxyethyl), 2'-F, 2'-O-[2-(methylamino)-2-oxoethyl] (2'-O-NMA), 2'-S-methyl, 2'-O—$CH_2$-(4'-C) (LNA) and 2'-O—$CH_2CH_2$-(4'-C) (ENA).

A double-stranded oligonucleotide may include at least one 5'-uridine-adenine-3' (5'-UA-3') dinucleotide wherein the uridine is a 2'-modified nucleotide, or a 5'-uridine-guanine-3' (5'-UG-3') dinucleotide, wherein the 5'-uridine is a 2'-modified nucleotide, or a terminal 5'-cytidine-adenine-3' (5'-CA-3') dinucleotide, wherein the 5'-cytidine is a 2'-modified nucleotide, or a terminal 5'-uridine-uridine-3' (5'-UU-3') dinucleotide, wherein the 5'-uridine is a 2'-modified nucleotide, or a terminal 5'-cytidine-cytidine-3' (5'-CC-3') dinucleotide, wherein the 5'-cytidine is a 2'-modified nucleotide, or a terminal 5'-cytidine-uridine-3' (5'-CU-3') dinucleotide, wherein the 5'-cytidine is a 2'-modified nucleotide, or a terminal 5'-uridine-cytidine-3' (5'-UC-3') dinucleotide, wherein the 5'-uridine is a 2'-modified nucleotide. Double-stranded oligonucleotides including these modifications are particularly stabilized against endonuclease activity.

General References

The oligoribonucleotides and oligoribonucleosides used in accordance with this invention may be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., Hely. Chim. Acta, 1995, 78, 486-504; Beaucage, S. L. and Iyer, R. P., Tetrahedron, 1992, 48, 2223-2311 and Beaucage, S. L. and Iyer, R. P., Tetrahedron, 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. Nos. 5,256,775 or 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. J. Org. Chem. 2001, 66, 2789-2801. Preparation of sulfur bridged nucleotides is described in Sproat et al. Nucleosides Nucleotides 1988, 7,651 and Crosstick et al. Tetrahedron Lett. 1989, 30, 4693.

Sugar Group References

Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Hely. Chim. Acta 1996, 79, 1930-1938), "LNA" (Wengel, J. Acc. Chem. Res. 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. Nucleic Acids Res. 1988, 16, 4583. Carbonate replacements are described in Tittensor, J. R. J. Chem. Soc. C 1971, 1933. Carboxymethyl replacements are described in Edge, M. D. et al. J. Chem. Soc. Perkin Trans. 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. Antisense and Nucleic Acid Drug Development 12, 103-128 (2002) and references therein.

Nuclebases References

N-2 substitued purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references are disclosed in the above section on base modifications Oligonucleotide Production The oligonucleotide compounds of the invention can be prepared using solution-phase or solid-phase organic synthesis. Organic synthesis offers the advantage that the oligonucleotide strands comprising non-natural or modified nucleotides can be easily prepared. Any other means for such synthesis known in the art may additionally or alternatively be employed. It is also known to use similar techniques to prepare other oligonucleotides, such as the phosphorothioates, phosphorodithioates and alkylated derivatives. The double-stranded oligonucleotide compounds of the invention may be prepared using a two-step procedure. First, the individual strands of the double-stranded molecule are prepared separately. Then, the component strands are annealed.

Regardless of the method of synthesis, the oligonucleotide can be prepared in a solution (e.g., an aqueous and/or organic solution) that is appropriate for formulation. For example, the oligonucleotide preparation can be precipitated and redissolved in pure double-distilled water, and lyophilized. The dried oligonucleotiode can then be resuspended in a solution appropriate for the intended formulation process.

Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof;

U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-fluoro-oligonucleotides.

Angiogenic-Related Disease and Disorder

The angiogenesis-related disease or disorder can be selected, for example, from a group consisting of cancer, ascites formation, psoriasis, age-related macular degeneration, thyroid hyperplasia, preeclampsia, rheumatoid arthritis and osteoarthritis, Alzheimer's disease, obesity, psoriasis, atherosclerosis, vascular malformations, angiomata, pleural effusion, atherosclerosis, endometriosis, diabetic/other retinopathies, neovascular glaucoma, age-related macular degeneration, hemangiomas, corneal neovascularization, sickle cell anemia, sarcoidosis, syphilis, pseudoxanthoma elasticum, Paget's disease, vein occlusion, artery occlusion, carotid obstructive disease, chronic uveitis/vitritis, Mycobacteria infections, Lyme disease, systemic lupus erythematosis, retinopathy of prematurity, vascular malformations, angiomata, Eales' disease, Behcet's disease, infections causing retinitis or choroiditis, presumed ocular histoplasmosis, Best's disease, myopia, optic pits, Stargardt's disease, pars planitis, chronic retinal detachment, hyperviscosity syndromes, toxoplasmosis, histoplasmosis, trauma and post-laser complications. In one embodiment, the age-related macular degeneration is wet macular degeneration. Other eye-associated diseases that can involve inappropriate angiogenesis include, but are not limited to, diseases associated with rubeosis (neovascularization of the angle) and diseases caused by the abnormal proliferation of fibrovascular or fibrous tissue, including all forms of prolific vitreoretinopathy.

In one embodiment, the angiogenesis-related disease or disorder is cancer, where the rapidly dividing neoplastic cancer cells require an efficient blood supply to sustain the continued growth of the tumor. As used herein, "cancer" refers to any of various malignant neoplasms characterized by the proliferation of anaplastic cells that tend to invade surrounding tissue and metastasize to new body sites and also refers to the pathological condition characterized by such malignant neoplastic growths. The blood vessels provide conduits to metastasize and spread elsewhere in the body. Upon arrival at the metastatic site, the cancer cells then work on establishing a new blood supply network. Administration of a pharmaceutically effective amount of a TRPV4 inhibitor or a pharmaceutical composition comprising a TRPV4 inhibitor and a pharmaceutically acceptable carrier can inhibit angiogenesis. By inhibiting angiogenesis at the primary tumor site and secondary tumor site, embodiments of the invention serve to prevent and limit the progression of the disease.

It is emphasized that any solid tumor that requires an efficient blood supply to keep growing is a candidate target. For example, candidates for the treatment methods described herein include carcinomas and sarcomas found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include, for example, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma. Abnormal build up and growth of blood vessels in the skin or internal organs in the form of hemangiomas can also be treated according to the methods described herein.

In one embodiment, the methods described herein can be used in preventing blinding blood vessel growth associated with diabetic eye diseases, namely diabetic retinopathy. The methods described herein can antagonize the effects of VEGF, a substance naturally produced in the body that promotes blood vessel formation. Released by the retina (light-sensitive tissue in back of the eye) when normal blood vessels are damaged by tiny blood clots due to diabetes, VEGF turns on its receptor, igniting a chain reaction that culminates in new blood vessel growth. However, the backup blood vessels are faulty; they leak, bleed and encourage scar tissue that detaches the retina, resulting in severe loss of vision. Such growth is the hallmark of diabetic retinopathy, the leading cause of blindness among young people in developed countries.

In yet another embodiment, the invention can be used in the treatment of age-related macular degeneration, as it is known that VEGF also contributes to abnormal blood vessel growth from the choroid layer of the eye into the retina, similar to what occurs during the wet or neovascular form of age-related macular degeneration. Macular degeneration, often called AMD or ARMD (age-related macular degeneration), is the leading cause of vision loss and blindness in Americans aged 65 and older. New blood vessels grow (neovascularization) beneath the retina and leak blood and fluid. This leakage causes permanent damage to light-sensitive retinal cells, which die off and create blind spots in central vision or the macula. Administration of a TRPV4 inhibitor can serve to inhibit unwanted neovascularization in the choroid layer of the eye.

In one embodiment, the angiogenesis-related disease or disorder is rheumatoid arthritis. Rheumatoid arthritis (RA) is characterized by synovial tissue swelling, leukocyte ingress and angiogenesis, or new blood vessel growth. The disease is thought to occur as an immunological response to an as yet unidentified antigen. The expansion of the synovial lining of joints in rheumatoid arthritis (RA) and the subsequent invasion by the pannus of underlying cartilage and bone necessitate an increase in the vascular supply to the synovium, to cope with the increased requirement for oxygen and nutrients. Angiogenesis is now recognised as a key event in the formation and maintenance of the pannus in RA (Paleolog, E. M., 2002, Arthritis Res. 4 (Suppl 3):S81-S90). Even in early RA, some of the earliest histological observations are blood vessels. A mononuclear infiltrate characterizes the synovial tissue along with a luxuriant vasculature. Angiogenesis is integral to formation of the inflammatory pannus and without angiogenesis, leukocyte ingress could not occur (Koch, A. E., 2000, Ann. Rheum. Dis.; 59(Suppl 1):i65-i71). Disruption of the formation of new blood vessels would not only prevent delivery of nutrients to the inflammatory site, it could also reduce joint swelling due to the additional activity of VEGF, a potent pro-angiogenic factor in RA, as a vascular permeability factor. Anti-VEGF hexapeptide RRKRRR (dRK6) (SEQ. ID. NO. 12) can suppress and mitigate the arthritis severity (Seung-Ah Yoo, et. al., J Immunol. 2005, 174:5846-55). Inhibition of angiogenesis by a pharmaceutically effective amount of TRPV4 inhibitor can also suppress and mitigate the arthritis severity.

In one embodiment, the angiogenesis-related disease or disorder is Alzheimer's disease. Alzheimer's disease (AD) is the most common cause of dementia worldwide. AD is characterized by an excessive cerebral amyloid deposition leading to degeneration of neurons and eventually to dementia. The exact cause of AD is still unknown. It has been shown by epidemiological studies that long-term use of non-steroidal anti-inflammatory drugs, statins, histamine H2-receptor blockers, or calcium-channel blockers, all of which are cardiovascular drugs with anti-angiogenic effects, seem to prevent Alzheimer's disease and/or influence the outcome of AD patients. Therefore, it has been speculated that angiogenesis in the brain vasculature may play an important role in AD. In Alzheimer's disease, the brain endothelium secretes the precursor substrate for the beta-amyloid plaque and a neurotoxic peptide that selectively kills cortical neurons. Moreover amyloid deposition in the vasculature leads to endothelial cell apoptosis and endothelial cell activation which leads to neovascularization. Vessel formation could be blocked by the VEGF antagonist SU 4312 as well as by statins, indicating that anti-angiogenesis strategies based on VEGF inhibition can interfere with endothelial cell activation in AD (Schultheiss C., el. al., 2006, Angiogenesis. 9(2):59-65; Grammas P., et. al., 1999, Am. J. Path., 154(2):337-42) and can be used for preventing and/or treating AD. In the same way, the anti-angiogenic properties of a pharmaceutically effective amount of TRPV4 inhibitor can be useful preventing and/or treating AD.

In one embodiment, the pathological angiogenic disease or disorder is obesity. Adipogenesis in obesity requires close interplay between differentiating adipocytes, stromal cells, and blood vessels. There are close spatial and temporal interrelationships between blood vessel formation and adipogenesis, and the sprouting of new blood vessels from preexisting vasculature is coupled to adipocyte differentiation. Adipogenic/angiogenic cell clusters can morphologically and immunohistochemically be distinguished from crown-like structures frequently seen in the late stages of adipose tissue obesity. Administration of anti-VEGF antibodies inhibited not only angiogenesis but also the formation of adipogenic/angiogenic cell clusters, indicating that the coupling of adipogenesis and angiogenesis is essential for differentiation of adipocytes in obesity. (Satoshi Nishimura et. al., 2007, Diabetes 56:1517-1526). It has been shown that the angiogenesis inhibitor, TNP-470 was able to prevent diet-induced and genetic obesity in mice (Ebba Bråkenhielm et. al., Circulation Research, 2004; 94:1579). TNP-470 reduced vascularity in the adipose tissue, thereby inhibiting the rate of growth of the adipose tissue and obesity development.

In one embodiment, the angiogenesis-related disease or disorder is endometriosis. Excessive endometrial angiogenesis is proposed as an important mechanism in the pathogenesis of endometriosis (Healy, D L., et. al., 1998, Human Reproduction Update, 4:736-740). The endometrium of patients with endometriosis shows enhanced endothelial cell proliferation. Moreover there is an elevated expression of the cell adhesion molecule integrin vβ3 in blood vessels in the endometrium of women with endometriosis when compared with normal women. U.S. Pat. No. 6,121,230 described the use of anti-VEGF agents in the treatment of endometriosis and this Patent is incorporated hereby reference. Encompassed in the methods disclosed herein is the treatment of endometriosis with anti-angiogenic therapy. Encompassed in the methods disclosed herein is the treatment of obesity with anti-angiogenic therapy, including the use of a pharmaceutically effective amount of TRPV4 inhibitor.

Diseases associated with chronic inflammation are accompanied by angiogenesis and can be treated by the compositions and methods of the present invention. Diseases with symptoms of chronic inflammation include obesity, inflammatory bowel diseases such as Crohn's disease and ulcerative colitis, psoriasis, sarcoidosis, atherosclerosis including plaque rupture, Sjogrens disease, acne rosacea, syphilis, chemical burns, bacterial ulcers, fungal ulcers, Behcet's syndrome, Stevens-Johnson's disease, Mycobacteria infections, Herpes simplex infections, Herpes zoster infections, protozoan infections, Mooren's ulcer, leprosy, Wegener's sarcoidosis, pemphigoid, lupus, systemic lupus erythematosis, polyarteritis, lyme's disease, Bartonelosis, tuberculosis, histoplasmosis and toxoplasmosis. Angiogenesis is a key element that these chronic inflammatory diseases have in common. The chronic inflammation depends on continuous formation of capillary sprouts to maintain an influx of inflammatory cells. The influx and presence of the inflammatory cells sometimes produce granulomas to help maintain the chronic inflammatory state. Inhibition of angiogenesis by the compositions and methods of the present invention would prevent the formation of the granulomas and alleviate the disease.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus, reducing the influx of inflammatory cells and the lesion formation.

Sarcoidosis is another chronic inflammatory disease that is characterized as a multisystem granulomatous disorder. The granulomas of this disease may form anywhere in the body, and, thus, the symptoms depend on the site of the granulomas and whether the disease active. The granulomas are created by the angiogenic capillary sprouts providing a constant supply of inflammatory cells.

Anti-Angiogenic Factors/Drugs

In one embodiment, the pharmaceutically effective amount of TRPV4 inhibitor can be administer in conjunction with one or more additional anti-angiogenic factors, drugs or therapeutics. For example, other potent angiogenesis inhibitors such as angiostatin, endostatin and cleaved antithrombin III can be incorporated into the composition.

There are three main types of anti-angiogenic drugs that are currently approved by the United States Food and Drug Administration (FDA) for the treatment of cancer and tumors: (1) Drugs that stop new blood vessels from sprouting (true angiogenesis inhibitors); (2) Drugs that attack a tumor's established blood supply (vascular targeting agents); and (3) Drugs that attack both the cancer cells as well as the blood vessel cells (the double-barreled approach).

In one embodiment, the anti-angiogenic therapy includes but is not limited to the administration of monoclonal antibody therapies directed against specific pro-angiogenic growth factors and/or their receptors. Examples of these are: bevacizumab (AVASTIN®), cetuximab (ERBITUX®), panitumumab (VECTIBIX™), and trastuzumab (HERCEPTIN®).

In another embodiment, the anti-angiogenic therapies include but are not limited to administration of small molecule tyrosine kinase inhibitors (TKIs) of multiple pro-angiogenic growth factor receptors. The three TKIs that are currently approved as anti-cancer therapies are erlotinib (TARCEVA®), sorafenib (NEXAVAR®), and sunitinib (SUTENT®).

In another embodiment, the anti-angiogenic therapies include but are not limited to administration of inhibitors of mTOR (mammalian target of rapamycin) such as temsirolimus (TORICEL™), bortezomib (VELCADE®), thalidomide (THALOMID®) and Doxycyclin.

Many of the current anti-angiogenesis factors or drugs attack the VEGF pathway. Bevacizumab (AVASTIN®) was the first drug that targeted new blood vessels to be approved for use against cancer. It is a monoclonal antibody that binds to VEGF, thereby blocking VEGF from reaching the VEGF receptor (VEGFR). Other drugs, such as sunitinib (SUTENT®) and sorafenib (NEXAVAR®), are small molecules that attach to the VEGF receptor itself, preventing it from being turned on. Such drugs are collectively termed VEGF inhibitors.

As the VEGF protein interacts with the VEGFRs, inhibition of either the ligand VEGF, e.g. by reducing the amount that is available to interact with the receptor; or inhibition of the receptor's intrinsic tyrosine kinase activity, blocks the function of this pathway. This pathway controls endothelial cell growth, as well as permeability, and these functions are mediated through the VEGFRs.

"VEGF inhibitors" include any compound or agent that produces a direct or indirect effect on the signaling pathways that promote growth, proliferation and survival of a cell by inhibiting the function of the VEGF protein, including inhibiting the function of VEGF receptor proteins. These include any organic or inorganic molecule, including, but not limited to modified and unmodified nucleic acids such as antisense nucleic acids, RNAi agents such as siRNA or shRNA, peptides, peptidomimetics, receptors, ligands, and antibodies that inhibit the VEGF signaling pathway. The siRNAs are targeted at components of the VEGF pathways and can inhibit the VEGF pathway. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (AEterna Zentaris Inc; Quebec City, Calif.), ZM323881 (CALBIOCHEM® CA, USA), pegaptanib (Macugen) (Eyetech Pharmaceuticals), an anti-VEGF aptamer and combinations thereof.

VEGF inhibitors are also disclosed in U.S. Pat. Nos. 6,534,524 and 6,235,764. Additional VEGF inhibitors are described, for example, in WO 99/24440; WO 95/21613; WO 98/50356; WO 99/10349; WO 97/22596; WO 97/32856; WO 98/54093; WO 98/02438; WO 99/16755; WO 99/61422; WO 99/62890; WO 98/02437; WO 01/02369; WO 01/95353; WO 02/44158; WO 03/106462A1; U.S. Pat. Publ. No. 20060094032; U.S. Pat. Nos. 6,534,524; 5,834,504; 5,883,113; 5,886,020; 5,792,783; 6,653,308; U.S. Provisional Application No. 60/491,771; and U.S. Provisional Application No. 60/460,695. These references are incorporated herein in their entirety.

In one embodiment, the pharmaceutically effective amount of TRPV4 inhibitor can be administer in conjunction with VEGF inhibitors.

In another embodiment, other anti-angiogenic factors include but are not limited to alpha-2 antiplasmin (fragment), angiostatin (plasminogen fragment), antiangiogenic antithrombin III, cartilage-derived inhibitor (CDI), CD59 complement fragment, endostatin (collagen XVIII fragment), fibronectin fragment, gro-beta (a C-X-C chemokine), heparinases heparin hexasaccharide fragment, human chorionic gonadotropin (hCG), interferon alpha/beta/gamma, interferon inducible protein (IP-10), interleukin-12, kringle 5 (plasminogen fragment), beta-thromboglobulin, EGF (fragment), VEGF inhibitor, endostatin, fibronection (45 kD fragment), high molecular weight kininogen (domain 5), NK1, NK2, NK3 fragments of HGF, PF-4, serpin proteinase inhibitor 8, TGF-beta-1, thrombospondin-1, prosaposin, p53, angioarrestin, metalloproteinase inhibitors (TIMPs), 2-Methoxyestradiol, placental ribonuclease inhibitor, plasminogen activator inhibitor, prolactin 16 kD fragment, proliferin-related protein (PRP), retinoids, tetrahydrocortisol-S transforming growth factor-beta (TGF-b), vasculostatin, and vasostatin (calreticulin fragment), pamidronate-thalidomide, TNP470, the bisphosphonate family such as amino-bisphosphonate zoledronic acid. bombesin/gastrin-releasing peptide (GRP) antagonists such as RC-3095 and RC-3940-II (Bajol A M, et. al., British Journal of Cancer (2004) 90, 245-252), and anti-VEGF peptide RRKRRR (dRK6) (SEQ. ID. NO. 12) (Seung-Ah Yoo, J. Immuno, 2005, 174: 5846-5855).

Anti-Angiogenesis Assay Methods

The effectiveness of any given TRPV4 inhibitor as described herein can be evaluated in vitro or in vivo or both, as described, e.g., in the examples provided herein below. For the avoidance of doubt, one can also use other assays commonly accepted in the field. For example, one can use the "CAM" assay. The chick chorioallantoic membrane (CAM) assay is frequently used to evaluate the effects of angiogenesis regulating factors because it is relatively easy and provides relatively rapid results. A TRPV4 inhibitor useful in the methods described herein will decrease the number of microvessels in the modified CAM assay described by Iruela-Arispe et al., 1999, Circulation 100: 1423-1431 (incorporated herein by reference in its entirety), relative to controls with no TRPV4 inhibitor that is added (control). The method is based on the vertical growth of new capillary vessels into a collagen gel pellet placed on the CAM. In the assay as described by Iruela-Arispe et al., the collagen gel is supplemented with $VEGF_{165}$ (250 ng/gel) in the presence or absence of a TRPV4 inhibitor. The extent of the anti-angiogenic effect is measured using FITC-dextran (50 μg/mL) (SIGMA ALDRICH®) injected into the circulation of the CAM. The degree of fluorescence intensity parallels variations in capillary density; the linearity of this correlation can be observed with a range of capillaries between 5 and 540. Morphometric analyses are performed, for example, by acquisition of images with a CCD camera. Images are then analyzed by importing into an analysis package, e.g., NHImage 1.59, and measurements of fluorescence intensity are obtained as positive pixels. Each data point is compared with its own positive and negative controls present in the same CAM and interpreted as a percentage of inhibition, considering the positive control to be 100% ($VEGF_{165}$ alone) and the negative control (vehicle alone) 0%. Statistical evaluation of the data is performed to check whether groups differ significantly from random, e.g., by analysis of contingency with Yates' correction.

Additional angiogenesis assays are known in the art and can be used to evaluate a TRPV4 inhibitor for use in the methods described herein. These include, for example, the corneal micropocket assay, hamster cheek pouch assay, the MATRIGEL™ assay and modifications thereof, and co-culture assays. Donovan et al. describe a comparison of three different in vitro assays developed to evaluate angiogenesis regulators in a human background (Donovan et al., 2001, Angiogenesis 4: 113-121, incorporated herein by reference). Briefly, the assays examined include: 1) a basic MATRIGEL™ assay in which low passage human endothelial cells (Human umbilical vein endothelial cells, HUVEC) are plated in wells coated with MATRIGEL™ (Becton Dickinson, Cedex, France) with or without angiogenesis regulator(s); 2) a similar MATRIGEL™ assay using "growth factor reduced" or GFR MATRIGEL™; and 3) a co-culture assay in which primary human fibroblasts and HUVEC are co-cultured with or without additional angiogenesis regulator(s)—the fibroblasts produce extracellular matrix and other factors that support HUVEC differentiation and tubule formation. In the Donovan et al. paper the co-culture assay provided microvessel networks that most closely resembled microvessel networks in vivo. Other CE cells, such as the bovine CE cells described herein, can be used instead of HUVEC. In addition, the basic MATRIGEL™ assay and the GFR MATRIGEL™ assay can also be used by one of skill in the art to evaluate whether a given TRPV4 inhibitor is an angiogenesis inhibitor as necessary for the methods described herein. Finally, an in vitro angiogenesis assay kit is marketed by CHEMICON®. The Fibrin Gel In Vitro Angiogenesis Assay Kit is CHEMICON® Catalog No. ECM630. A TRPV4 inhibitor as described herein is considered useful in a method for the inhibition of angiogenesis and for the treatment of an angiogenesis-related disease or disorder as described herein if it reduces angiogenesis in any one of these assays by 10% or more relative to a control assay performed the absence of any TRPV4 inhibitor. A TRPV4 inhibitor as described herein preferably reduces angiogenesis in one or more of these assays by at least 10%, at least 20%, at least 30%, at least 40%, at least 50%, at least 60%, at least 70%, at least 80%, at least 90% or more, up to and including 100% inhibition.

Alternatively, angiogenesis inhibition can be measured functionally downstream, as a reduction or cessation of tumor growth or tumor size. For example, if there is zero growth of tumor mass, or at least 5% reduction in the size of the tumor mass, there is angiogenesis inhibition by the methods as described herein.

Formulation and Administration

In one embodiment, the TRPV4 inhibitor is delivered in a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration. Additional carrier agents, such as liposomes, can be added to the pharmaceutically acceptable carrier.

As used herein, the terms "administering," refers to the placement of a TRPV4 inhibitor that can inhibit angiogenesis into a subject by a method or route which results in at least partial localization of the TRPV4 at a desired site. The TRPV4 inhibitor can be administered by any appropriate route which results in an effective treatment in the subject.

As used herein, the term "comprising" or "comprises" is used in reference to methods, and respective component(s) thereof, that are essential to the invention, yet open to the inclusion of unspecified elements, whether essential or not. The use of "comprising" indicates inclusion rather than limitation.

The term "consisting of" refers to methods, and respective components thereof as described herein, which are exclusive of any element not recited in that description of the embodiment.

Therapeutic compositions contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Specifically contemplated pharmaceutical compositions are active RNAi ingredients in a preparation for delivery as described herein above, or in references cited and incorporated herein in that section. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

Routes of administration include, but are not limited to, direct injection, intradermal, intravitreal, intramuscular, intraperitoneal, intravenous, subcutaneous, intranasal, epidural, and oral routes. The agent can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The precise dose and formulation to be employed depends upon the potency of the inhibitor, and include amounts large enough to produce the desired effect, e.g., a reduction in invasion of new blood vessels in the eye or elsewhere. The dosage should not be so large as to cause unacceptable adverse side effects. Generally, the dosage will vary with the type of TRPV4 inhibitor (e.g., an antibody or fragment, small molecule, siRNA, etc.), and with the age, condition, and sex of the patient are also considered. Dosage and formulation of the TRPV4 inhibitor will also depend on the route of administration, and the seriousness of the disease or disorder, and should be decided according to the judgment of the practitioner and each patient's circumstances. Effective doses can be extrapolated from dose-response curves derived from in vitro or animal model test systems.

The dosage can be determined by one of skill in the art and can also be adjusted by the individual physician in the event of any complication. Typically, the dosage ranges from 0.001mg/kg body weight to 5 g/kg body weight. In some embodiments, the dosage range is from 0.001 mg/kg body weight to lg/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 μg/kg body weight to 30 μg/kg body weight. Alternatively, the dose range will be titrated to maintain serum levels between 5 μg/mL and 30 μg/mL.

Administration of the doses recited above can be repeated for a limited period of time. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

As exemplary, for the treatment of solid tumors that are accessible by catheters or needles, the TRPV4 inhibitor and a pharmaceutically acceptable carrier can be formulated for direct application by injection into the solid tumor and/or adjacent to the tumor site, e.g. melanoma and hemangiomas. The inhibitor can also be formulated for a transdermal delivery, e.g. a skin patch. For cancers or tumors not so easily accessible, the TRPV4 inhibitor can be administered to one of the main blood vessel that drains the cancer site, e. g. into the portal vein for liver cancer. For the treatment of macular degeneration or retinopathy, the TRPV4 inhibitor can be formulated for direct injection into the vitreous cavity of the affected eye.

In one embodiment, the TRPV4 inhibitor is an RNA interference molecule such as an siRNA. Such siRNA is delivered by delivering a vector encoding small hairpin RNA (shRNA) in a pharmaceutically acceptable carrier to the cells in an organ of an individual. The shRNA is converted by the cells after transcription into siRNA capable of targeting TRPV4. In one embodiment, the vector can be a regulatable vector, such as tetracycline inducible vector. Such vectors with inducible promoters are well known in the art and are also easily found in the commercial sector, e. g. pSingle-tTS-shRNA vector from CLONTECH®.

In one embodiment, the treatment of angiogenesis-related diseases related to the eyes, e. g. macular degeneration or diabetic retinopathy, comprises directly injecting an siRNA, dsRNA, or shRNA vector directed against a TRPV4 gene into the vitreous cavity of the affected eye.

In other embodiments, the treatment of angiogenesis-related diseases having localized aberrant angiogenesis, e. g. solid non-metastatic tumor, arthritis, and endometriosis, comprises directly injecting an siRNA, dsRNA, or shRNA vector directed against a TRPV4 gene to the location of tissue with aberrant angiogenesis.

In one embodiment, the RNA interfering molecules used in the methods described herein are taken up actively by cells in vivo following intravenous injection, e.g., hydrodynamic injection, without the use of a vector, illustrating efficient in vivo delivery of the RNA interfering molecules, e.g., the siRNAs used in the methods of the invention.

Other strategies for delivery of the RNA interfering molecules, e.g., the siRNAs or shRNAs used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

In some embodiments, the siRNA, dsRNA, or shRNA vector directed against a TRPV4 gene is administered intravenously, e. g. via central venous catheter (CVC or central venous line or central venous access catheter) placed into a large vein in the neck (internal jugular vein), chest (subclavian vein) or groin (femoral vein). Methods of systemic delivery of siRNA, dsRNA, or shRNA vector are well known in the art, e. g. as described herein and in Gao and Huang, 2008, (Mol. Pharmaceutics, Web publication December 30) and review by Rossil, 2006, Gene Therapy, 13:583-584. The siRNA, dsRNA, or shRNA vector can be formulated in various ways, e.g. conjugation of a cholesterol moiety to one of the strands of the siRNA duplex for systemic delivery to the liver and jejunum (Soutschek J. et. al. 2004, Nature, 432:173-178), complexing of siRNAs to protamine fused with an antibody fragment for receptor-mediated targeting of siRNAs (Song E, et al. 2005, Nat Biotechnol., 23: 709-717) and the use of a lipid bilayer system by Morrissey et al. 2005 (Nat Biotechnol., 23: 1002-1007). The lipid bilayer system produces biopolymers that are in the 120 nanometer diameter size range, and are labeled as SNALPs, for Stable-Nucleic-Acid-Lipid-Particles. The lipid combination protects the siRNAs from serum nucleases and allows cellular endosomal uptake and subsequent cytoplasmic release of the siRNAs (see WO/2006/007712). These references are incorporated by reference in their entirety.

In another embodiment, the treatment of angiogenesis-related diseases related to the eyes, e. g. macular degeneration or diabetic retinopathy comprises directly injecting an antibody specifically against a β1 integrin function into the vitreous cavity of the eye, wherein the integrin function is blocked by the antibody.

In other embodiments, the treatment of angiogenesis-related diseases having localized aberrant angiogenesis, e. g. solid non-metastatic tumor, arthritis, and endometriosis, comprises directly injecting an antibody specifically against a β1 integrin function into the location or tissue with aberrant angiogenesis, wherein the integrin function is blocked by the antibody.

In one embodiment, the antibody in a monoclonal antibody derived from clone P5D2.

In some embodiments, the TRPV4 inhibitor is a an antibody. a small molecule, a peptide or an aptamer. Such an inhibitor can be targeted to specific organ or tissue by means of a targeting moiety, such as e.g., an antibody or targeted liposome technology. In some embodiments, aTRPV4 inhibitor can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The conjugation of an antibody to a TRPV4 inhibitor permits the inhibitor attached to accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

For therapeutic applications, the antibodies can be administered to a mammal, preferably a human, in a pharmaceutically acceptable dosage form, including those that may be administered to a human intravenously as a bolus or by continuous infusion over a period of time, by intramuscular, subcutaneous, intra-articular, intrasynovial, intrathecal, oral, topical, or inhalation routes. The antibody is also suitably administered by intratumoral, peritumoral, intralesional, or perilesional routes, to exert local as well as systemic therapeutic effects.

In some embodiments, the antibody is administered intravenously, e. g. via central venous catheter (CVC or central venous line or central venous access catheter) placed into a large vein in the neck (internal jugular vein), chest (subclavian vein) or groin (femoral vein).

Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, and sublingual tablets. The antibody will typically be formulated in such vehicles at a concentration of about 0.1 mg/ml to 100 mg/ml.

Depending on the type and severity of the disease, about 0.015 to 15 mg/kg of antibody is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful.

The effectiveness of the antibody in treating disease can be improved by administering the antibody serially or in combination with another agent that is effective for those purposes, such as another antibody directed against a different epitope or neutralizing a different protein than the first antibody, or one or more conventional therapeutic agents such as, for example, alkylating agents, folic acid antagonists, antimetabolites of nucleic acid metabolism, antibiotics, pyrimidine analogs, 5-fluorouracil, purine nucleosides, amines, amino acids, triazol nucleosides, corticosteroids, calcium, retinoids, lipoxygenase and cyclooxygenase inhibitors, fumaric acid and its salts, analgesics, psychopharmaceuticals, local anesthetics, spasmolytics, and beta-blockers. Such other agents can be present in the composition being administered or can be administered separately. Also, the antibody is suitably administered serially or in combination with radiological treatments, whether involving irradiation or administration of radioactive substances.

Efficacy testing can be performed during the course of treatment using the methods described herein. Measurements of the degree of severity of a number of symptoms associated with a particular ailment are noted prior to the start of a treatment and then at later specific time period after the start of the treatment. For example, when treating an autoimmune disease such as rheumatoid arthritis, the severity of joint pain can be scored from a number of 1-10, with a score of 1 representing mild discomfort and a score of 10 represent constant unbearable pain with or without movement; the range of motion of an affected joint can also are be measured as a degree of angle for which that joint can move. The joint pain and range of motion are noted before and after a treatment. The severity of joint pain and range of motion after the treatment are compared to those before the treatment. A decrease in the pain score and/or an increase in the degree of angle of joint movement indicate that the treatment is effective in reducing inflammation in the affected joint, thereby decreasing pain and improving joint movement. Other methods of efficacy testing includes evaluating for visual problems, new blood vessel invasion, rate of vessel growth, angiogenesis, etc.: (1) inhibiting the disease, e.g., arresting, or slowing the pathogenic growth of new blood vessels; or (2) relieving the disease, e.g., causing regression of symptoms, reducing the number of new blood vessels in a tissue exhibiting pathology involving angiogenesis (e. g., the eye); and (3) preventing or reducing the likelihood of the development of a neovascular disease, e.g., an ocular neovascular disease).

The present invention can be defined in any of the following alphabetized paragraphs:

[A] The use of a TRPV4 inhibitor for inhibiting endothelial cell migration.

[B] The use of paragraph [A], wherein the TRPV4 inhibitor is selected from the group consisting of an antibody, an RNA interference molecule, a small molecule, a peptide and an aptamer.

[C] The use of an siRNA directed specifically against a TRPV4 gene for inhibiting endothelial cell migration.

[D] The use of an antibody directed specifically against a β1 integrin for inhibiting endothelial cell migration, wherein the integrin function is blocked by the antibody.

[E] The use of paragraph [D], wherein the antibody is a monoclonal antibody derived from clone P5D2.

[F] The use of any of paragraphs [A]-[E], wherein the endothelial cell is a mammalian endothelial cell.

[G] The use of paragraph [F], wherein the mammalian endothelial cell is a human endothelial cell.

[H] The use of a therapeutically effective amount of a TRPV4 inhibitor and a pharmaceutically acceptable carrier for inhibiting angiogenesis in a mammal in need thereof.

[I] The use of a therapeutically effective amount of a TRPV4 inhibitor and a pharmaceutically acceptable carrier for the manufacture of a medicament for inhibiting angiogenesis in a mammal in need thereof.

[J] The use of paragraph [H] or [I] wherein the TRPV4 inhibitor is selected from the group consisting of an antibody, an RNA interference molecule, a small molecule, a peptide and an aptamer.

[K] The use of an siRNA directed specifically against a TRPV4 gene for inhibiting angiogenesis in a mammal in need thereof.

[L] The use of an siRNA directed specifically against a TRPV4 gene for the manufacture of a medicament for inhibiting angiogenesis in a mammal in need thereof.

[M] The use of an antibody directed specifically against a β1 integrin for inhibiting angiogenesis in a mammal in need thereof, wherein the integrin function is blocked by the antibody.

[N] The use of an antibody directed specifically against a β1 integrin for the manufacture of a medicament for inhibiting angiogenesis in a mammal in need thereof, wherein the integrin function is blocked by the antibody.

[O] The use of paragraph [M] or [N], wherein the antibody is a monoclonal antibody derived from clone P5D2.

[P] The use of any of paragraph [K]-[O], wherein the mammal is afflicted with an angiogenesis-related disease or disorder.

[Q] The use of paragraph [P], the angiogenesis-related disease is selected from the group consisting of cancer, macular degeneration; diabetic retinopathy; rheumatoid arthritis; Alzheimer's disease; obesity, psoriasis, atherosclerosis, vascular malformations, angiomata, and endometriosis.

[R] The use of any of paragraph [K]-[Q], wherein the mammal is a human.

[S] The use of a therapeutically effective amount of a TRPV4 inhibitor and a pharmaceutically acceptable carrier for the treatment of an angiogenesis-related disease in a mammal in need thereof.

[T] The use of a therapeutically effective amount of a TRPV4 inhibitor and a pharmaceutically acceptable carrier for the manufacture of a medicament for the treatment of an angiogenesis-related disease in a mammal in need thereof.

[U] The use of paragraph [S] or [T], wherein the TRPV4 inhibitor is selected from the group consisting of an antibody, an RNA interference molecule, a small molecule, a peptide and an aptamer.

[V] The use of an siRNA directed specifically against a TRPV4 gene for the treatment of an angiogenesis-related disease in a mammal in need thereof.

[W] The use of an siRNA directed specifically against a TRPV4 gene for the manufacture of a medicament for the treatment of an angiogenesis-related disease in a mammal in need thereof.

[X] The use of an antibody directed specifically against a β1 integrin for the treatment of an angiogenesis-related disease in a mammal in need thereof, wherein the integrin function is blocked by the antibody.

[Y] The use of an antibody directed specifically against a β1 integrin for the manufacture of a medicament for the treatment of an angiogenesis-related disease in a mammal in need thereof, wherein the integrin function is blocked by the antibody.

[Z] The use of any of paragraph [S]-[Y], wherein the angiogenesis-related disease is selected from the group consisting of cancer, macular degeneration; diabetic retinopathy; rheumatoid arthritis; Alzheimer's disease; obesity, psoriasis, atherosclerosis, vascular malformations, angiomata, and endometriosis.

[AA] The use of any of paragraph [S]-[Y], wherein the mammal is a human.

[BB] The use of any of paragraph [S]-[Y], wherein an anti-angiogenic therapy is included.

[CC] The use of any of paragraph [S]-[Y], wherein chemotherapy or radiation therapy is included.

[DD] A method for inhibiting endothelial cell migration, the method comprising contacting an endothelial cell with a TRPV4 inhibitor.

[EE] The method of paragraph [DD], wherein the TRPV4 inhibitor is selected from the group consisting of an antibody, an RNA interference molecule, a small molecule, a peptide and an aptamer.

[FF] The method of paragraph [EE], wherein the TRPV4 inhibitor inhibits an influx of calcium into the cell.

[GG] The method of paragraph [EE], wherein the TRPV4 inhibitor is an RNA interference molecule that inhibits TRPV4 expression in the cell.

[HH] The method of paragraph [GG], wherein the TRPV4 inhibitor is an siRNA directed specifically against a TRPV4 gene.

[II] The method of paragraph [EE], wherein the TRPV4 inhibitor inhibits a phosphorylation of β1 integrin in the cell.

[JJ] The method of paragraph [EE], wherein the TRPV4 inhibitor inhibits a phosphorylation of AKT in the cell.

[KK] The method of paragraph [EE], wherein the TRPV4 inhibitor is an antibody directed specifically against a β1 integrin.

[LL] The method of paragraph [DD], wherein the endothelial cell is a mammalian endothelial cell.

[MM] The method of paragraph [DD], wherein the mammalian endothelial cell is a human endothelial cell.

[NN] A method for inhibiting endothelial cell migration, the method comprising contacting an endothelial cell with an siRNA directed specifically against a TRPV4 gene.

[OO] A method for inhibiting endothelial cell migration, the method comprising contacting an endothelial cell with an antibody directed specifically against a β1 integrin, wherein the integrin function is blocked by the antibody.

[PP] The method of paragraph [OO], wherein the antibody is a monoclonal antibody derived from clone P5D2.

[QQ] A method for inhibiting angiogenesis in a mammal in need thereof, the method comprising administering a therapeutically effective amount of a TRPV4 inhibitor and a pharmaceutically acceptable carrier.

[RR] A method of treating an angiogenesis-related disease in a mammal in need thereof, the method comprising administering a therapeutically effective amount of a TRPV4 inhibitor and a pharmaceutically acceptable carrier.

[SS] The method of paragraph [QQ] or [RR], wherein the TRPV4 inhibitor is selected from the group consisting of an antibody, an RNA interference molecule, a small molecule, a peptide and an aptamer.

[TT] A method for inhibiting angiogenesis in a mammal in need thereof, the method comprising administering a therapeutically effective amount of an siRNA directed specifically against a TRPV4 gene and a pharmaceutically acceptable carrier.

[UU] A method for inhibiting angiogenesis in a mammal in need thereof, the method comprising administering a therapeutically effective amount of an antibody directed specifically against a β1 integrin and a pharmaceutically acceptable carrier, wherein the integrin function is blocked by the antibody.

[VV] The method of any of paragraph [QQ], [TT] and [UU], wherein the mammal is afflicted with an angiogenesis-related disease or disorder.

[WW] A method treating an angiogenesis-related disease in a mammal in need thereof, the method comprising administering a therapeutically effective amount of an siRNA directed specifically against a TRPV4 gene and a pharmaceutically acceptable carrier.

[XX] A method of treating an angiogenesis-related disease in a mammal in need thereof, the method comprising administering a therapeutically effective amount of an antibody directed specifically against a β1 integrin and a pharmaceutically acceptable carrier, wherein the integrin function is blocked by the antibody.

[YY] The method of paragraph [UU] or [XX], wherein the antibody is a monoclonal antibody derived from clone P5D2.

[ZZ] The method of any of paragraph [RR], [VV]-[XX], wherein the angiogenesis-related disease is selected from the group consisting of cancer, macular degeneration; diabetic retinopathy; rheumatoid arthritis; Alzheimer's disease; obesity, psoriasis, atherosclerosis, vascular malformations, angiomata, and endometriosis.

[AAA] The method of any of paragraph [RR]-[XX], wherein the mammal is a human.

[BBB] The method of any of paragraph [RR]-[XX], wherein an anti-angiogenic therapy is administered in conjunction with the method.

[CCC] The method of any of paragraph [RR]-[XX], wherein a chemotherapy and/or radiation therapy is administered in conjunction with the method.

This invention is further illustrated by the following example which should not be construed as limiting. The contents of all references cited throughout this application, as well as the figures and table are incorporated herein by reference.

EXAMPLE

Materials and Methods

Cell Cultures

Bovine CE cells (passage 10 to 15) were maintained at 37° C. in 10% $CO_2$ on gelatin-coated tissue culture dishes in low glucose Dulbecco's Modified Eagle's Medium (DMEM; INVITROGEN™ Inc.) supplemented with 10% fetal calf serum (FCS) (HyClone), 10 mM HEPES (JRH-Biosciences) and L-glutamine (0.292 mg/ml), penicillin (100 U/ml), streptomycin (100 μg/ml) (GPS), as described in Matthews, et. al. (J Cell Sci., 119:508-518 (2006)). Human microvascular endothelial cells from dermis (HMVECs) (Cambrex, Walkersville, Md.) were cultured in EBM-2 (Cambrex), supplemented with 5% FBS and growth factors (bFGF, IGF, VEGF) according to the manufacturer's instructions.

Materials

Antibodies against activated β1 integrin (clone 12G10) were from ABD Serotec and those directed against T788/789 of β1 integrin cytoplasmic tail, and phosho FAK pY-397 were from Biosource™ International/MILLIPORE®. ALEXA®-conjugated phalloidin and secondary antibodies were from MOLECULAR PROBES®/INVITROGEN™ Inc. Antibodies against phospho AKT Ser-473, AKT, phospho-ERK1/2, ERK1/2 and FAK were from CELL SIGNALING TECHNOLOGY®, and those against vinculin and actin were from SIGMA ALDRICH®. Human fibronectin was obtained from BD™ Biosciences. Gadolinium Chloride, 4-α-PDD and ruthenium red were purchased from SIGMA ALDRICH®; LY294002 was from CALBIOCHEM®.

Mechanical Strain Application

CE cells cultured on fibronectin-coated 6 well UNIFLEX™ (FLEXCELL® International) plates for 24 hours were subjected to uniaxial cyclic stretch (10% elongation; 1 Hz frequency) for 1-2 h using a FLEXERCELL® TENSION PLUS™ System (FLEXCELL® International). In some experiments, CE cells were plated on fibronectin-coated 6 well BIOFLEX® (FLEXCELL® International) for lh and subjected to static stretch (15% elongation) for 1-15 min. Control cells were maintained under identical conditions in the absence of strain application. Calcium Imaging: CE cells adherent to the flexible substrates were loaded with Fluo-4/AM (1 μM) for 30 min, washed 3 times in calcium medium (136 mM NaCl, 4.7 mM KCl, 1.2 mM $MgSO_4$, 1.1 mM $CaCl_2$, 1.2 mM $KH_2PO_4$, 5 mM $NaHCO_3$, 5.5 mM glucose, and 20 mM Hepes. pH 7.4) and then exposed to mechanical strain (15% elongation) for 3-4 sec using a Stage Flexer (FLEXCELL® International) apparatus that is fixed on a Nikon upright microscope equipped with CCD camera (Spot-RT slider, Diagnostics Corp, USA). Images were acquired for every 4 seconds and analyzed using IP lab software and Microsoft Excel as described in Matthews, et. al. (2006) (J. Cell Sci., 119:508-518). Calcium imaging with TRPV channel activators was performed on cells cultured on MatTek glass bottomed dishes on LEICA® Confocal Microscope and analyzed using LEICA® software and MICROSOFT® EXCEL®. siRNA knock down of TRPV channels: smart pool siRNAs (10 nM) of TRPV2, TRPV4 (both from Dharmacon), TRPC1 (AMBION®) or control (QIAGEN®) siRNAs was transfected into CE cells using SILENTFECT™ reagent (BIORAD®) as described in Mammoto et. al. (2007) (J. Cell Sci., 120:456-467). Three days later cells were used for calcium imaging or reorientation experiments. The knock down of TRPV channel expression was assessed using RT-PCR with species-specific primers and Western blotting. The primers used for RT-PCR were: TRPV2 (human: Forward—CAAACCGATTTGACCGAGAT (SEQ. ID. NO. 13); Reverse—GTTCAGCACAGCCTTCATCA (SEQ. ID. NO. 14) and bovine: Forward—CAGCTGGGAGGAAAACTCAG (SEQ. ID. NO. 15); Reverse—GGGAGGAAGTCCTTTTCCAG (SEQ. ID. NO. 16)), TRPV4 (human: Forward—GACGGGGACCTATAGCATCA (SEQ. ID. NO. 17); Reverse—AACAGGTCCAGGAGGAAGGT (SEQ. ID. NO. 18) and bovine: Forward—GACTACCTGCGGCTGGC (SEQ. ID. NO. 19); Reverse—TTCATCCAGCCCAGGAC (SEQ. ID. NO. 20)), TRPC1 (human: Forward—CACTCGTTCATTGGCACCTGCTTT (SEQ. ID. NO. 21); Reverse—GCAGCTTCGTCAGCACAATCACA (SEQ. ID. NO. 22); bovine: Forward—CCATTCGTTCATCGGCACTTGCTT (SEQ. ID. NO. 23); Reverse—TTATGAAGCATTGCCACCAGCAGC (SEQ. ID. NO. 24)) and GAPDH (Forward—ACCACAGTCCATGCCATCAC (SEQ. ID. NO. 25); Reverse—TCCACCACCCTGTTGCTGTA (SEQ. ID. NO. 26)).

Morphological and Immuno Fluorescence Studies

Cells were transfected with GFP-AKT-PH domain (kind gift of Dr. Martin Schwartz) using EFFECTENE® (QIAGEN®, Chatsworth, Calif.). Cells adherent to flexible ECM substrates and subjected to mechanical stretch were washed in PBS, fixed in 4% paraformaldehyde for 30 min either mounted on glass slides (for visualizing GFP-AKT-PH translocation) or permeabilized with 0.25% TRITON®-X 100/PBS for 5 min for immuno staining. After blocking with DMEM containing 10% FBS, cells were incubated for 1 h with ALEXA®-phalloidin to visualize stress fibers, washed and mounted on glass slides using FLUOROMOUNT-G™ (Southern Biotech). For staining focal adhesions, cells were incubated with antibodies against vinculin for 1 h followed by rinsing and incubation with ALEXA®-conjugated secondary antibodies; activated 131 integrins were detected using 12G10 antibody. Images were acquired on a LEICA® Confocal SP2 microscope and processed using LEICA® software and Adobe Photoshop. GFP-AKT-PH domain translocation to the plasma membrane was quantified measuring either ratio of the perimeter of whole cell membrane and the membrane that contains the GFP-AKT-PH domain or the ratio of GFP fluorescence intensity of translocated GFP-AKT-PH domain and cytosol adjacent to the membrane. CE cell reorientation in response to cyclic strain was measured by quantitating the angle of orientation of cells relative to the direction of applied strain using ImageJ software and MICROSOFT® EXCEL®. Cells on substrates exposed to uniaxial cyclic strain with their longest axis oriented between 60 and 120 degrees relative to the direction of the applied strain field were considered to be aligned. Statistical differences between experimental groups were determined using the student t-test.

Biochemical Analysis

Western blotting were performed according to methods published in Mammoto et. al. (2007) (J. Cell Sci., 120:456-467). Membranes containing transferred protein were blocked in 3% BSA/TBST for 1 h and incubated overnight with primary antibodies against AKT and phospho Ser-473 AKT (1:1000), phospho-Thr 788/789 of 131 integrin cytoplasmic tail (1:1000), ERK1/2 and phospho ERK1/2 (1:1000), FAK and phospho FAK-pY397 (1:1000), actin (1:1000) and TRPV4 (1:1000) at 4° C. The membranes were subsequently washed incubated with HRP-conjugated secondary antibodies (1:5000) for 1 h and washed and incubated with SUPERSIGNAL® West Pico ECL reagent from Pierce Biotechnology Inc. (USA) and exposed to Kodak X-ray film (SIGMA ALDRICH®).

Integrin Activation Assay

β1 integrin activation was measured using a glutathione S-transferase (GST) fusion protein consisting of FN III repeat 8-11 domains or 12G10 antibodies (Orr, A. W. et. al., 2006, Mol. Biol. Cell 17:4686-4697). Briefly, cells subjected to mechanical stretch were incubated with either 5 μg/ml of GST-FN $III_{8-11}$ protein or 12G10 antibodies in PBS containing $Ca^{2+}$ and $Mg^{2+}$ for 30 min at 37° C., washed and lysed in SDS-sample buffer. The samples were separated on SDS-PAGE and the bound reagents were assessed on Western blots using anti GST-antibodies and HRP-conjugated secondary antibodies.

FACS Analysis

Activated β1 integrin expression was measured with specific antibodies (12G10) using flow cytometry (Kawaguchi et al., 2003, J. Cell Sci., 116:3893-3904). Briefly, cells were incubated with 12G10 antibody in FACS buffer (PBS containing 1% bovine serum albumin) for 20 min on ice and fixed in 4% paraformaldehyde for 15 min. After fixation, the cells were washed twice with FACS buffer and incubated with PE-conjugated secondary antibodies (Vector Laboratories, USA) for 20 min on ice. The cells were then washed twice and analyzed on GUAVA® Personal Cytometer (GUAVA® Technologies). Isotype-matched IgG and secondary antibodies alone were used as controls.

Whole-Cell Patch Clamp Experiments

One day after bovine CE cells were transfected with TRPV4-EGFP, they were plated on gelatin-coated glass coverslips and allowed to grow for ~24 h prior to recording. Cells were recorded in the whole-cell mode using borosilicate glass pipettes (1-3 MΩ) containing: (in mM) 120 $CsMeSO_3$, 10 EGTA, 2 $MgCl_2$, 10 HEPES; pH and osmolarity were adjusted with CsOH or $HMeSO_3$, as needed, to 7.2 (23° C.) and ~300 mOsm, respectively. Cells were bathed in a solution containing (in mM): 138 NaCl, 5 KCl, 1.8 $CaCl_2$, 1 $MgCl_2$, 10 HEPES; pH and osmolarity were adjusted with NaOH or HCl, as needed, to 7.4 (23° C.) and ~310 mOsm, respectively. Cells were held at −40 mV for 3-5 min to allow for intracellular dialysis. Bath superfusion was stopped prior to initiating the recording of currents resulting from the indicated voltage protocol applied every 5 s. Immediately before use, a 4-α-PDD stock solution (2 mM in EtOH, on ice) was diluted 1:50 in bath solution under vortex and 50 μl was subsequently added to a still bath (0.5 ml) by pipette (final concentrations of 4 μM 4-α-PDD and 0.2% EtOH) and mixed by 3 gentle up/down pipette strokes. Once a clearly discernable 4-α-PDD-induced current was observed (typically after a 10-30 sec delay), the bath solution was changed to a $Na^+$— and $Ca^{2+}$-free solution (in mM: 145 N-methyl-D-glucamine.Cl, 10 HEPES, adjusted to pH 7.4 and ~310 mOsm with HCl) by re-starting the superfusion. In some cases, the original bath solution was later re-introduced as a wash.

Cell Migration and In Vitro Angiogenesis Assay

Cell migration assay was performed using Transwell assay. Briefly, cells were plated on to gelatin coated (0.5%) transwell membranes (Coster) in EBM2 supplemented with 0.3% FBS and their migration in response to VEGF (10 ng/ml) was monitored. The migrated cells were stained with Giemsa solution for 16 h and ten random fields were counted. To measure in vitro angiogenesis, CE cells were plated on MATRIGEL™ (BD Biosciences) and incubated in the presence of VEGF (10 ng/ml) at 37° C. After 18 h, tube formation was assessed in ten random fields (Mamotto, 2009, Nature 457:1103-1109).

RESULTS

Capillary Cell Reorientation Induced by Cyclic Strain

To begin to analyze the molecular mechanism by which mechanical strain can influence CE cell motility and angiogenesis as observed in ECM gels and living tissues (Korff and Augustin, 1999, J. Cell Sci. 112: 3249-3258; Jounget. al., 2005, Micro vasc Res.; Matsumoto et al. 2007, Tissue Eng 13:207-217; Pietramaggiori, et al. 2007, Ann. Surg. 246:896-902), bovine CE cells were cultured on flexible fibronectin-coated substrates and subjected to 10% uniaxial cyclical strain (1 Hz) using a FLEXERCELL® TENSION PLUS™ system. Fluorescence microscopic analysis of cells labeled with ALEXA® 488-phalloidin combined with computerized morphometry revealed that stress fibers thickened in these cells, and almost 90% of them realigned perpendicular to the main axis of the applied strain within 2 hr after force application (FIG. 1). Immunofluorescence micrographs of CE cells subjected to 0 or 10% uniaxial cyclic strain and stained for vinculin and actin stress fibers showing that application of strain causes enhanced recruitment of vinculin to large focal adhesions that colocalize with the ends of reinforced stress fibers, indicating that stress fiber realignment was accompanied by redistribution and reorientation of focal adhesions containing vinculin (data not shown), focal adhesion kinase (FAK) and talin (not shown), which appeared in close association with the ends of newly aligned stress fibers (data not shown).

Strain-Induced Capillary Cell Reorientation Requires β1 Integrin Activation

Figure 9:
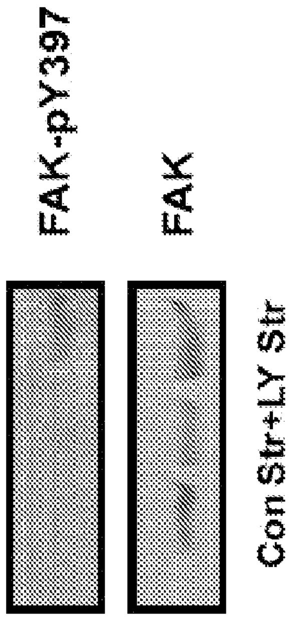
FIG. 9 shows the representative Western blot showing mechanical strain (15%, 15 min) dependent tyrosine phosphorylation of FAK (FAK-pY397 antibody) in bovine CE cells in the absence and presence of the PI3 kinase inhibitor, LY 294002 (LY, 40 μM).
Figure 8:
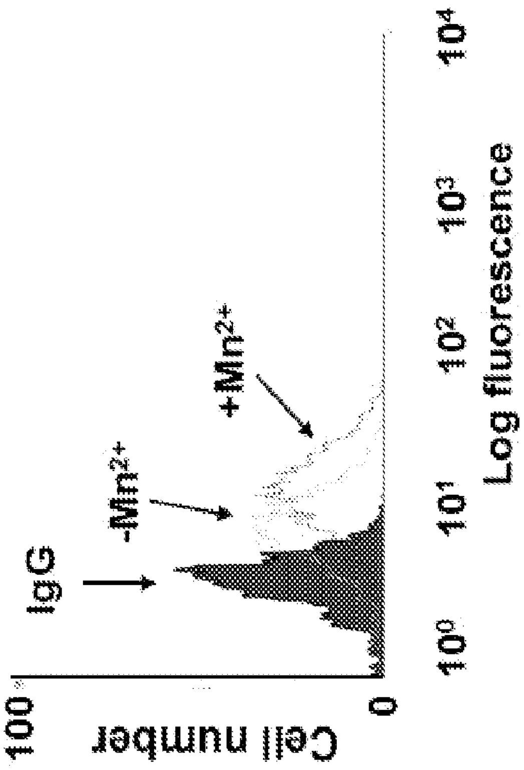
FIG. 8 shows the flow cytometric analysis of activated β1 integrin expression on bovine CE cells detected using the 12G10 antibody in the absence and presence of manganese ($Mn^{2+}$). Note that the expression of activated β1 integrin is increased following treatment with manganese. The istoype-matched control IgG is shown as a red peak.

The effects of fluid shear on large vessel endothelium (Tzima et. al. 2001, Embo J. 20:4639-4647) and mechanical strain on fibroblasts (Katsumi, A. et. al. 2005, Biol. Chem. 280:16546-1 6549) are mediated by stress-dependent activation of integrin receptors within minutes after force application. When CE cells cultured on flexible fibronectin-coated substrates were exposed to static biaxial strain (15%), β1 integrin activation increased within 1 min after strain application, as indicated by increased phosphorylation of the T788/789 site of the β1 integrin cytoplasmic tail in Western blots (FIG. 2A), which has been shown to correlate with integrin activation (Nilsson, S. et. al. 2006, Exp. Cell. Res. 312:844-853; Stawowy, P. et al., 2005, Cardiovasc. Res. 67:50-59; Wennerberg, K., 1998, J Cell Sci. 111:1117-1126). Immunofluorescence staining using 12G10 antibodies that only recognize the activated conformation of β1 integrins (Humphries, M. J. 2004 Biochem. Soc. Trans. 32:407-411; Thodeti, C. K. et al. 2003, J. Biol. Chem. 278:9576-9584) also showed increased clustering of activated integrins within large streak-like focal adhesions at the cell periphery within 15 min after force application (data not shown). The ability of the 12G10 antibody to detect activated integrins in the CE cells was confirmed using flow cytometry, which demonstrated a significantly increased 12G10 signal after globally activating integrins by treatment with manganese (FIG. 8). Mechanical strain-induced activation of integrin signaling was confirmed independently by demonstrating increased phosphorylation of MAP kinase (ERK1/2) (FIG. 2B) and FAK within 5-15 min after exposure to mechanical strain (FIG. 9). Application of uniaxial cyclic strain (10%; 1 Hz) also induced β1 integrin activation within minutes, as measured by increased T788/789 phosphorylation (FIG. 4C) and enhanced binding of both a fibronectin fragment (GST-$FNIII_{8-11}$) (FIGS. 2C and 4B) and the 12G10 antibody that only ligate the activated form of the β1 integrin receptor (FIG. 2D) (Orr, et. al. 2006, Mol. Biol. Cell. 17:4686-4697). Cyclic strain also increased β1 integrin activation in human CE cells as measured by enhanced binding of GST-$FNIII_{8-11}$ (FIG. 4B), and thus, this appears to be a generalized response in CE cells.

To explore if this mechanical strain-induced wave of β1 integrin activation is required for CE cell reorientation, cells were pre-incubated with function-blocking anti-β1 integrin (P5D2) antibody for 30 min, and then the cells were subjected to uniaxial cyclical strain (10%) for 2 hr. Treatment with this inhibitory antibody inhibited strain-induced cell realignment by almost 70% ($p<0.001$) (FIG. 2E), and it also prevented associated reorientation of stress fibers and focal adhesions (data not shown). These results indicate that application of mechanical strain to CE cells through existing integrins that are bound to substrate-immobilized ECM molecules (and hence activated) induces focal adhesion remodeling, stress fiber realignment, and cell reorientation through a mechanism that requires activation of additional integrin receptors.

PI3K is Upstream of β1 Integrin Activation in this Mechanical Signaling Cascade

PI3K has been implicated in the activation of β1 integrins by fluid shear stress in large vessel endothelium (Tzima, E. et al. 2005 Nature 437:426-431), however, it also can act downstream of integrin activation (Berrier, A. L., et. al., 2000 J. Cell Biol. 151:1549-1 560). To explore whether PI3K is involved in early mechanical signaling in microvascular endothelium, CE cells were transfected with GFP-fused to an AKT-PH domain that translocates to the plasma membrane when it binds to the PI3K product, phosphatidyl inositol-3-phosphate (Watton and Downward, 1999 Curr. Biol. 9:433-436). Bright linear AKT-PH-GFP staining was detected at the peripheral membrane within 1 min after application of mechanical strain (15%), whereas it remained diffusely distributed throughout the cytoplasm in control (unstrained) CE cells (data not shown). Quantification of AKT-PH-GFP translocation by two independent parameters (fraction of AKT-PH-GFP in total perimeter of the membrane, or GFP-fluorescence intensity ratio between membrane and cytosol) revealed a significant increase in response to mechanical strain that was inhibited by treatment with the PI3K inhibitor, LY294002 (FIG. 3A). Mechanical strain also activated PI3K as determined by enhanced phosphorylation of its downstream target AKT at Ser-473 within minutes after force application, as detected in Western blots (FIG. 3B). Moreover, strain-induced translocation of AKT-PH-GFP to the membrane and AKT phosphorylation were both abolished by inhibiting PI3K with LY294002 (FIGS. 3A and C). LY294002 treatment also prevented β1 integrin activation (FIG. 3C) and suppressed FAK activation (FIG. 9). Thus, force application through ECM-integrin adhesions activates additional cell surface β1 integrin receptors by stimulating PI3K activity.

Strain-Induced Cytoskeletal Reorientation is Mediated by Stress-Activated Ion Channels SA ion channels have been implicated in force-dependent alignment of large vessel endothelial cells (Naruse, K., et. al. 1998 Am. J. Physiol. 274:H1 532- 1538). Direct force application to cell surface β1 integrins using magnetic tweezers also results in rapid (within 2-5 sec) calcium influx in the bovine CE cells, and this response can be blocked using the general SA channel inhibitor, gadolinium chloride (Yang and Sachs, 1989 Science 243:1068-1071; Matthews, B. D., et. al., 2006, J. Cell Sci. 119:508-518). To confirm that mechanical strain also activates SA channels in these CE cells, cells adherent to flexible ECM substrates were loaded with the calcium reporter dye FLUO-4, subjected to static mechanical strain (15%) and calcium influx was measured using microfluorimetry (Matthews, B. D., et. al., 2006).

Stretching CE cells for as little as 3 sec induced rapid calcium influx, and this response could be almost completely abolished by treatment with gadolinium chloride (FIG. 4A). Pretreatment of bovine and human CE cells for 30 min with gadolinium chloride also significantly inhibited β1 integrin activation in response to mechanical strain, as measured by decreased binding of GST-$FNIII_{8-11}$ (FIG. 4B) and 12G10 antibody (not shown) that specifically bind to activated β1 integrins and reduced β1 integrin phosphorylation (FIG. 4C). In addition, gadolinium chloride inhibited PI3K activity, as measured by membrane translocation of GFP-AKT-PH (FIG. 4D). Finally, the cell and cytoskeletal reorientation that are normally induced by mechanical strain were also greatly suppressed in the presence of this SA ion channel blocker (FIG. 4E). Thus, strain-dependent activation of mechanosensitive calcium channels appears to be required for activation of both PI3K and β1 integrins, as well as subsequent cytoskeletal reorientation in CE cells.

TRPV4 Channels Mediate Cyclic Strain-Induced Capillary Cell Reorientation

Figure 10A:
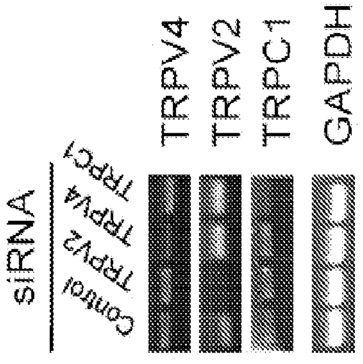
FIG. 10A showing a representative RT-PCR results confirming knockdown of TRPV4, TRPV2 and TRPC1 mRNA levels in human CE cells using specific siRNAs.
Figure 10B:
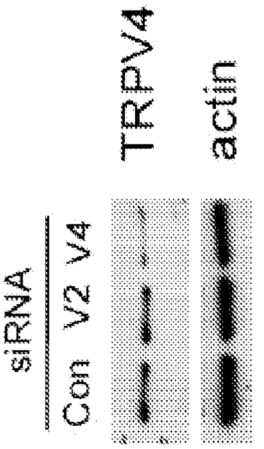
FIG. 10B showing a representative Western blotting analysis showing that the same TRPV4 siRNA produced comparable suppression of protein expression.
Figure 11A:
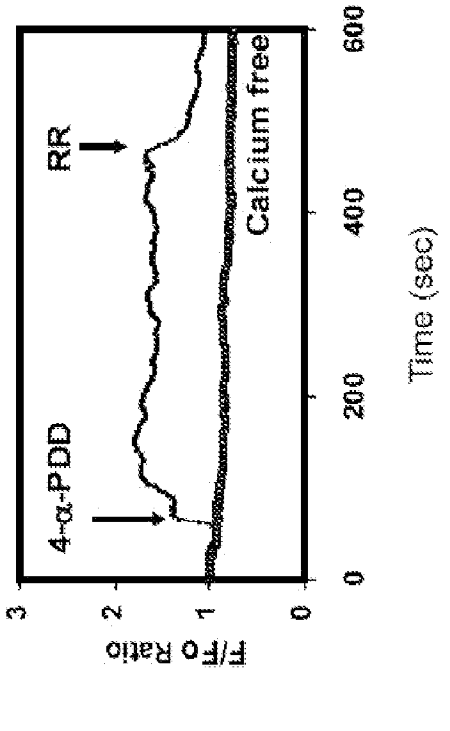
FIG. 11A shows the relative changes in cytosolic calcium measured in FLUO-4 loaded bovine CE cells in response to the specific TRPV4 activator 4-α-PDD (2 μM) or the TRPV4 blocker ruthenium red (RR, 2 μM) in the absence or presence of extracellular calcium. Arrows denote time drugs were added to cells. This indicates that TRPV4 channels are functionally expressed in CE cells.
Figure 11B:
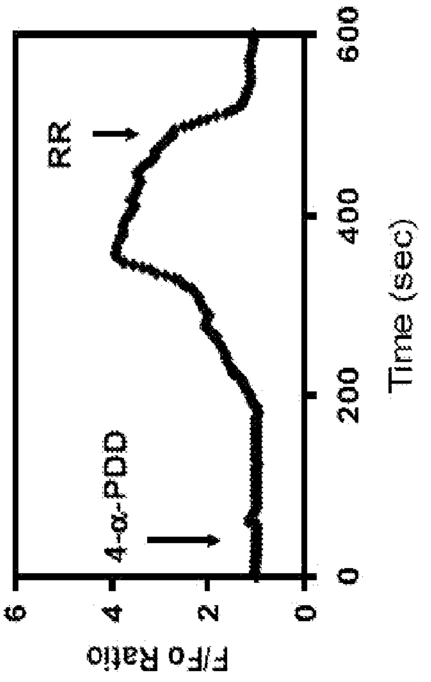
FIG. 11B shows the relative changes in cytosolic calcium measured in FLUO-4 loaded human CE cells in response to the specific TRPV4 activator 4-α-PDD (2 μM) or the TRPV4 blocker ruthenium red (RR, 2 μM) in the absence or presence of extracellular calcium. Arrows denote time drugs were added to cells. This indicates that TRPV4 channels are functionally expressed in CE cells.

The specific type of mechanosensitive ion channel that mediates the effects of mechanical stretching on CE cell orientation was identified. TRPV4 is an interesting potential candidate because it mediates cell sensitivity to osmotic stresses (Liedtke, W. 2005 J. Physiol. 567:53-58) and shear stress-induced vasodilation (Kohler, R. et al. 2006 Arterioscler. Thromb. Vasc. Biol. 26:1495-1502), and it was found that TRPV4 is activated within milliseconds after mechanical stresses are applied directly to apical cell surface β1 integrin receptors using magnetic cytometry. vasodilation. To determine whether TRPV4 is the candidate mechanosensitive channel, its expression was measured in CE cells. Western blot analysis showed a strong band around 85 kDa (and a fainter band at ~100 kDa) in both bovine and human CE cells (FIG. 5A). RT-PCR analysis also confirmed the presence of TRPV4 mRNA in both bovine and human CE cells (FIGS. 5B and 10). Moreover, a specific activator of TRPV4 channels, 4-α-PDD, induced a robust calcium signal in bovine as well as human CE cells, thus strongly indicating that both cell types express functional TRPV4 channels (FIG. 11).

Next, the TRPV4 channel activation was measured directly by whole-cell clamp using bovine CE cells transiently transfected with TRPV4-EGFP that gave robust TRPV4 currents in response to 4-α-PDD, and it was found that substitution of N-methyl-D-glucamine for cations in the bathing solution, inhibited activation of inward, but not outward, currents by 4-α-PDD in these cells (data not shown). This approach was used because TRPV4-like currents in primary endothelial cells are small, transient, and difficult to characterize, as previously described in Vriens J et. al., 2005 (Circ Res., 97:908-915) and as was observed herein as well. Thus, taken together, these findings strongly suggest that CE cells express functional TRPV4 channels, although at a low level.

To confirm that calcium influx through TRPV4 channels mediates the effects of mechanical strain on CE cell orientation, the expression of TRPV4 in bovine and human CE cells were knocked down using specific siRNA; sham siRNA and siRNA directed against the closely related channel, TRPV2, were used as controls. Sequence analysis of smart pool siRNAs confirmed that both siRNA sequences exhibit 80-100% homology with human and bovine TRPV4. RT-PCR analysis revealed that TRPV2 and TRPV4 mRNA levels were knocked down by 90% and 70%, respectively, in bovine CE cells using this approach, whereas use of a sham control siRNA had no effect (FIGS. 5B and 10). It was found that TRPV4 protein expression was also knocked down by ~60% and 80% in bovine and human CE cells, respectively (FIGS. 5C, 5D and 10).

Figures 12A, 12B, 12C, 12D:
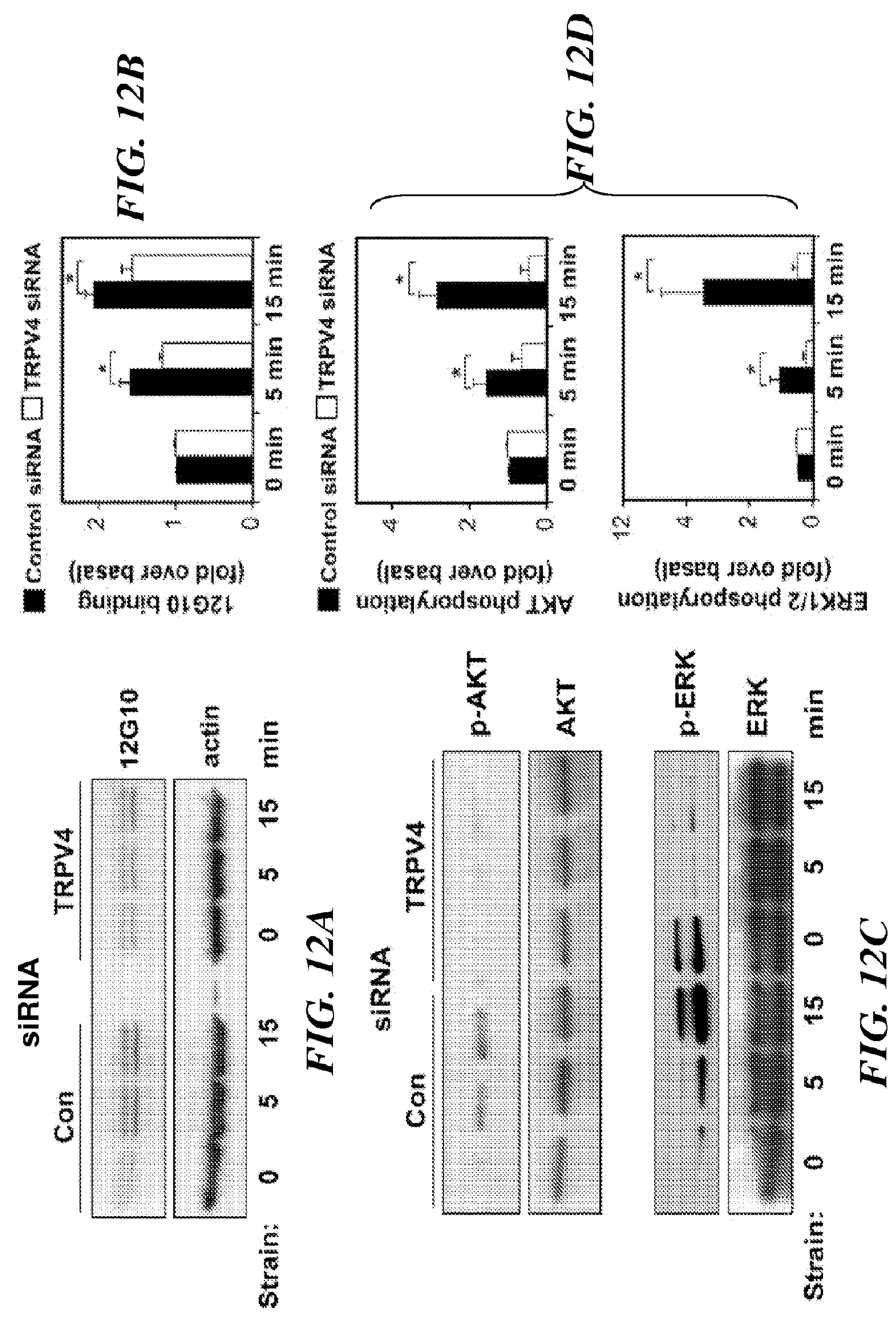
FIGS. 12A and B show the representative Western blots and histogram showing activation of β1 integrins as measured by binding to 12G10 antibody in response to cyclic strain in the control and TRPV4 siRNA—transfected CE cells at indicated times.
FIGS. 12C and D show the representative Western blots and histograms showing phosphorylation of AKT at Ser-473 and ERK1/2 in response to cyclic strain in the control and TRPV4 siRNA—transfected CE cells at indicated times. Phosphorylation/activation of signaling protein levels were measured as a percentage of total protein/actin levels and normalized to basal levels. *$P<0.05$ for comparison between control siRNA versus TRPV4 siRNA treated cells.

Importantly, microfluorimetric analysis revealed that application of mechanical strain (15%) for 4 sec induced a large wave of calcium influx in bovine CE cells transfected with control siRNAs, whereas this response was significantly inhibited ($p<0.02$) in cells treated with TRPV4 siRNA (FIG. 5E, F). In contrast, use of siRNA directed against the closely related SA channel TRPV2 had no effect (FIG. 5E, F). siRNA knock down of TRPV4 also inhibited cyclic strain-induced activation of β1 integrins, AKT, and ERK1/2, further confirming that TRPV4 activation is upstream of integrin activation (FIG. 12).

Figure 6C:
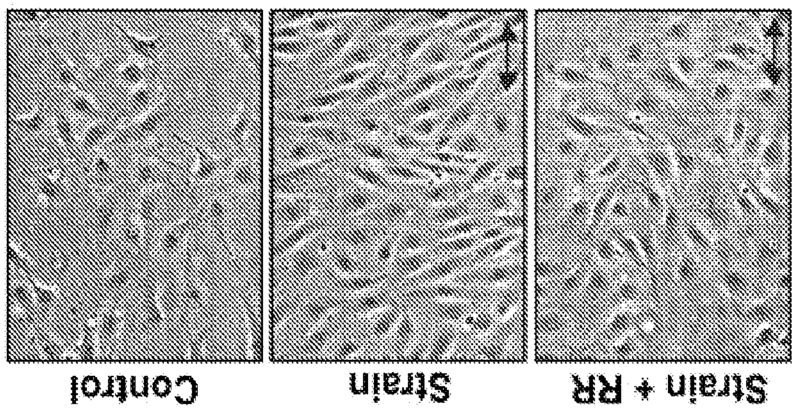
FIG. 6C shows the phase contrast photomicrographs of CE cells showing the effects of cyclic strain on cell reorientation in the absence and presence of ruthenium red. Arrow indicates the direction of applied strain. Note that ruthenium red inhibits cyclic strain-induced cell reorientation.
Figure 13:
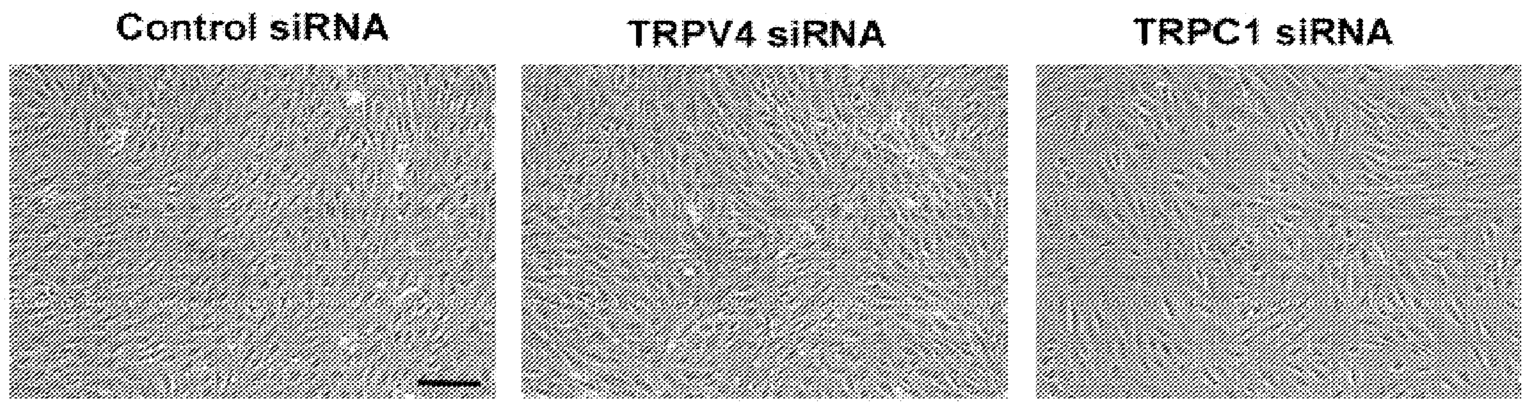
FIG. 13 shows phase contrast photomicrographs of human CE cells transfected with indicated siRNA showing that TRP siRNA treatment does not affect human CE cell morphology or viability. Scale bar: 100 μm.
Figure 14A:
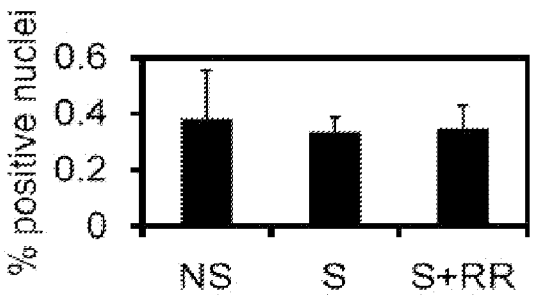
FIGS. 14A and B show quantification of cell proliferation (stained using ki 67antibody) and Western blot analysis for PARP (poly (ADP-ribose) polymerase) cleavage to assess apoptosis in CE cell, indicating that cyclic strain did not affect CE cell proliferation or apoptosis.
Figure 14B:
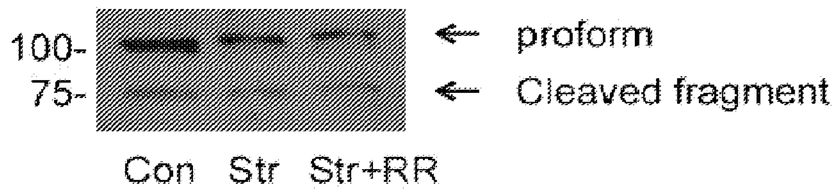

Pretreatment of CE cells with the general TRPV inhibitor, ruthenium red, or with TRPV4 siRNA also significantly suppressed calcium signaling and cell reorientation induced by application of cyclic strain in CE cells, whereas addition of siRNA against two different related SA channels, TRPV2 or TRPC1 (FIG. 10), were ineffective (FIG. 6). This inhibition was specific for reorientation as transfection of cells with TRPV4 siRNA did not alter the number of viable adherent CE cells when they were cultured on standard tissue culture substrates (FIG. 13). Moreover, it was found that application of similar cyclic strain, in the presence or absence of ruthenium red, did not effect CE cell proliferation or apoptosis, as measured by Ki 67 staining and poly(ADPribosyl) polymerase cleavage (FIG. 14). Taken together, these results indicate that TRPV4 channels are mechanosensitive calcium channels in CE cells that are activated by mechanical strain applied through the integrin-mediated cell-ECM adhesions, and that calcium influx through these channels is required for downstream signaling events that drive the cell and cytoskeletal reorientation response triggered by cell stretching.

TRPV4 Channels are Required for Sngiogenesis In Vitro

To determine if activation of TRPV4 channels by physical interactions between cells and ECM are physiologically relevant, these specific siRNAs were used to knock down the expression of TRPV4 and TRPC1 in human CE cells and tested their ability to form three-dimensional tubular capillary networks on MATRIGEL™ substrates. RT-PCR analysis confirmed that transfection of TRPV4 and TRPC1 siRNAs resulted in knock down of TRPV4 and TRPC1 mRNA levels by more than 70% and 90%, respectively (FIG. 7A), and, as described above, this resulted in suppression of TRPV4 protein levels by 90% in these human cells (FIG. 5C). TRPV4 siRNA also had no significant effect on expression of TRPC1, and vice versa (FIG. 7A). Importantly, knockdown of TRPV4 attenuated CE cell migration (FIG. 7B) and completely abolished tube formation in the MATRIGEL™ angiogenesis assay at 18 hr, whereas tubular differentiation proceeded normally when cells were transfected with sham control or TRPC1 siRNA at equal concentrations (FIG. 7C). This inhibition was specific for tube formation as transfection of cells with TRPV4 siRNA did not alter the number of viable adherent CE cells when they were cultured on standard, rigid tissue culture substrates (FIGS. 13 and 14). Thus, these findings indicate that TRPV4 channels mediate mechanical signaling through integrin-ECM adhesions in CE cells, and that this mechanotransduction response is required for angiogenesis in vitro.

The inventors have shown that application of mechanical strain to bound integrins on the CE cell surface stimulates calcium influx through mechano sensitive TRPV4 ion channels, which activates additional β1 integrins and subsequent downstream cytoskeletal reorientation responses that are required for formation of tubular capillary networks during angiogenesis.

The references cited herein and throughout the specification are incorporated herein by reference.

What is claimed is:

1. A method for inhibiting endothelial cell migration, the method comprising contacting an endothelial cell with a TRPV4 inhibitor, wherein the TRPV4 inhibitor is an RNA interference molecule that inhibits TRPV4 expression in the cell.

2. The method of claim 1, wherein the TRPV4 inhibitor is an siRNA directed specifically against a TRPV4 gene.

3. The method of claim 1, wherein the endothelial cell is a mammalian endothelial cell.

4. The method of claim 3, wherein the mammalian endothelial cell is a human endothelial cell.

* * * * *

SEQUENCE LISTING

```
<160> NUMBER OF SEQ ID NOS: 26

<210> SEQ ID NO 1
<211> LENGTH: 50319
<212> TYPE: DNA
<213> ORGANISM: Homo sapiens

<400> SEQUENCE: 1

ccggccggga ttcaggaagc gcggatctcc cggccgccgg cgcccagccg tcccggaggt      60

aagtggggcc cgggcccggg aggggcggct cagccgaggt cccctcgcgc ccctggggac     120

atctccgtgg cccgtccggc tccgggggt  cccgaggctc caaaatgcgg gccaggggcg     180

cgggagacgg aaggcaccag gttccgcagg cgccagcctc tcagctaagt gcccttgggc     240

cggacaccgg ctctttgggt ctcggtttta tcacctgtga aatgggcacc aacgtggggc     300

ctggggtagc aggtctgggg ggagggcggt tcggttccct gagaccccaa gccagggaac     360

caaaggcccg gagccttgca gcccacctta ggagacttgg aagagggatt tcgggggacc     420

taaggtttgc ccttggcccc tgagcatgtc ggagggaatt tggagtctgg agcttccaaa     480

ggcttcttct tggttactga gtcccggaga gacggctgtt tcctccaaga ggcatgaaaa     540

tctttaacct ctagttctgc cctggactct caggacgtcc cgggggcggg tggctcctgg     600
```

-continued

```
gggtgggtag cgggggtggg ggtgggggag agagagactc ccacactccc cgcttgcctg    660
gaaacaccaa ccacagatgc attcatcgag ccacccactg ctccagcctg ccccagctgt    720
tccctctgtc tgtcctctct gttttgcaga tggggaaact gaggcttagg tcggggatct    780
agacaattgg gatttaaacc cagggactat ccagccccaa agcccttccc accacaccag    840
gtggcctgtc ctggggccag ctctgcacac agggcctggt gcccccgggg tgcttgggaa    900
gtggcagggc agaggtgggc cctgtggctg ttctggctca gcttctaaaa caagagcctc    960
tgctgggggc agaggggccg tgaacccctg aaatgttagg cagataccct gtgggagctt   1020
tgttctggga tgctaagaac cgcttgagga tttaagcttt gccactttgg ctccggagca   1080
agggcagagg gtaagtcggg actccccggg ctcctgagga gggtgacgag gtgggctttt   1140
gggggaacaa gggtagaaag gtcaggcctg ggttatctgc ggggctaaga gcgggcctgt   1200
gtggggcccg gggtgtgctc tgcagtcccc tgctgtgtga ccttggcctg gtcccttagc   1260
tgtctgagcc tttgtgttct ctcctctgta atactggggt gcctgagggc aagcccccag   1320
ggctgtcgtg aggaccgatg accttccagg aacctggcac agccactgtt ggctgccatc   1380
aatgtttaac cagttgtcgt tgccccaaac attttcttaa caaagagggt gaaaaaagtc   1440
aattggccat ttccacattt ctctagttca ttctgtttga agaatgatgg gaaccagaaa   1500
gcctggacac ccaccttgat tggtgaattg cacgcggaag ggtcccagaa cacaaatggc   1560
aaatggcagt catagttcag ggcggttcac tttgtaagat caaggtgggg ctgttttgaa   1620
atggaggtaa ccagggaatg gttgcctgaa caaaaagggt gtgatgcccc caggagggat   1680
gtttcacatg agctccggtg aggatggctg ggattcccca ggtgaaaccc agataccttta   1740
tatctgggga aggggctgtg gaggttcctc ctgccttatc tggtgccaac tgggcctctg   1800
ccacttactc cctcctccag caaatgctct ctgcaagctc acctgtgcca gctctgggct   1860
gggcactgga gcagtgagat gcttccaatc ccagcttcgc tgtagcctga ggcgtgtgaa   1920
ggcaagaagg attttccctt gtggcccccc ggggaggagc tcccacacct gacttgtgag   1980
catctagcaa ggtgtgcatg gatggccgac gcttagtaaa tgtatgctgt ggaatggatg   2040
gggtcagggg agaatgccgt agggtaggag gactggccca ggaaggaccc acgagggctt   2100
ggtcaaggta gtgtttaagc cgcaccttaa agaataaatg cagaagtaga ggaaagagta   2160
ttcaggcaaa gagaatggca ctagcagaga tatgactttt acctgttacc aggtggctac   2220
acctggggtt tatagagcag agaaatagtt ctgtttgtct ggagtttgtg acgtgactgg   2280
aaagggtgag ggatcagaca ggcaggagct aaatcagacc cagaggccca gaagtcctgc   2340
ctgggagtga cacggttgtt tgtctgttct agaaaggtcc ctgtggctgc agagtgggaa   2400
agattggagg agctcagaca gagaggctgg ccccaaggct ggggaagtca tccaagctct   2460
gagtggagag cggcagctgg aaggagatgt aggagggaag gaaacacaca agactgagcc   2520
tcatgtgcct ggcacatagt aggtgctcag tcagtatcta tggcatggtt gtctgaacaa   2580
atacttttga gatggtcaaa gtcctttgag ttccttcctc tgttcctagg gggatggggt   2640
ctacatgaag tgggtgtctc tactccatgc aggcccttga ccctgctgtc tgcctcagtt   2700
tcccccattt gactttggga aagacactcc agtccgttct ccaaattata gggacccagg   2760
taacagctcc tcttgttgtc acagataggg tctggggagc caagataaca tttatttcat   2820
gccagtgggc cctctggaat gctccacatc gcccatttgg agcagaattc acctgttaaa   2880
gattaattcc gatctcttga gataagtggc tgctgttatg aactctgggt acaaggttct   2940
gtctggcttt agccaaccct gggttgcatt aacaactatt atgatggtgg caagccttta   3000
```

```
ttgagcactt actgtgtgcc aagcactgag tcaagcaccc tcagcacatt tggatacaaa   3060
actatttttg tctctatttt tcagagggca gaatgaggtc tagagggtga aatctcttgc   3120
ctgggttctc tcagctgaga aggggcagag ctgggacctg aatcccattt gtgtgattgc   3180
aaatccatcc cttcacctgt aaggtggccc gtccccattt gtctggaccc tcattggggt   3240
gcctggggtc atgggggagc tactctgcag tccagagata ggaacctgag ttggccgggt   3300
gcagtggccc acacctgtaa tcccaacact ctgggaggcc aaggcaggtg gatcggtcga   3360
gcccgtgagt ttgagaccag cctgggcaac atggtgaaac tctgtctcta gaaaaaatac   3420
aaaaattagc cgaacgtggt agcacgcacc tgtagtgcca gctacttgag aggctgaggt   3480
gggaggatcg cttaagccca ggagtgagag gttgcagtga actgcgattg tgccactgca   3540
gtccagagca agagatcctg tctcaaaaca aacaaagagc ctgaactgca gacaggcctg   3600
ggcttaaact gcatccgcat gtttaagaca ggcctgctat tccccgctgg aggagctcag   3660
ggaagccacc tggcctctct gggcttccat ttcctcctgt gtcaaaggga ctctcatccc   3720
actttgcagg gatgacccaa ggcacgtgga tggggctctg aagcacagct cttctgcctc   3780
agcccgtgtc agctcccctt gtccccaggc ccattccagg gcatgttttc ttccagctta   3840
tcccccagac atcctcagag agcccctcca tgccaggtgg gtgggtggaa ggtattgggg   3900
gcaaagctag acttgcattt gggcaaataa tgatatgttt tcagcaatga aatatttatg   3960
agcattgact gagtgccagg agctgtcaac tttttttact ttcctgattt aatgcttaaa   4020
aactagggct ggagcccagc tgcccaggtt caaatcccag cttccaataa gttccattat   4080
tcctttggcc tcagtttcct catctggaca atggggataa ggtaatgcct gccttgctgg   4140
gaggttgtgg acagtcttca gcacaacctt gagtgtttag tttaaaacca gcatctattg   4200
cctgttgttc actttttttt ttatttatta tttttagaga cagggtctca gtctgttgct   4260
caggctggaa tgcagtggtg tgatcatagc tcacagcagc ctcgaactcc tgggctcaag   4320
agatcctcct acttcagcct cccaagtagt tgggacacac ccagcttatt aaaaaaaaag   4380
gtttttttca gacaggggtc tcactatgtt gcccaggttg gtctggaatt ccagagctca   4440
agtaaccctc ctgccttggc ctcccaaagt gctcagatta caggtgtgag ggctgatgtt   4500
cattttgatg gtgtcacagc ttccccactg ccgggggtgg gcaggggcag gaatgctgag   4560
ccccatttta cagctgagga aatcgagact cagagaggaa gcaatttacc cagggatgcc   4620
cagctggctc atggcagagc tggagctgga agccagatct gagtgacact ggtgtccttg   4680
ggtccacgaa aagcccagtg gccagcttag cttcttgcgt ggaaagctac gctaggctca   4740
cccaccttgg cgtctgagcc accttagctt acctcccagc tccgccagtt gctgctctgt   4800
gacctcagaa agtggcttaa gctctctgtt cctgggcttt gctgaggtca gagctctgcc   4860
aacttgagga gggatttggg ttattctggc tgctgctctt gttctggcct gggctccttc   4920
aacctcgggt gcccttgcag cccatgagct ggcaccccag tggccggaca ggaatgagga   4980
agggacaggg cctcactttc aatgtgactc tgacttcctt cccaccccta gccccttcct   5040
gagcattggt ttccccttc tgccccgagc cctggccact gccggctgtg tgaccccaag   5100
gaggttacat cacttctctg agcatgtttc ctcatcggtg agggaggatc acacgagacc   5160
acaccaggcg cacaggaagc ccttgccggt ctccagatga ggtcagggca ttggaaaggc   5220
cacagaagga ggcgggggct caggggacag acaggcgggc cattgaccaa acgggaatat   5280
ccttctattt ctttggttag tgagtaacag cagcccctct tgtccaccca ccctgcccct   5340
tgcacaaaga gctcctcagt ctcaccaggc gcccgttttc ccctgagggt ggagtggcct   5400
```

-continued

```
gggttccacc cggttgaccg agtgggctgg ccaccttctg ggaccattcc ctgtgtgtgt   5460
gtttgtgtac gtgtgtatgt gtgtgtatat tgatgtgcgt gtgtatgtgc gtatgtgtgt   5520
ctgtgtgtgt atgtgtatgt gtgtatatgt atgtctatat gtgtatgtgt atatgtgtat   5580
atatgtgtat gtgtgtatat gtatgactat atgtttatgt gtatgtttgt gtatatatgt   5640
gtgtatgtgt gtatatgtat gtctgtgtgt atgtgtgtgc atatgtgtat gtatatacat   5700
gtgtatgtgt gtatgtgaat gtctatgtgt gcatgtgtgt atgtgtgtgt atgtttgcgt   5760
gtatatgtat gtatgtgtgt atattgtgtg tatgtatgtg tatatgtgtg taatgtgtat   5820
atgtatttgt gtgtagtgtg tgtgtgtgtg tgtgtttatg gagggtgggt tccatgggct   5880
ttgggctgag accccagcag gtgagggtgg gacagggggc atggggttga ctgacccatg   5940
ggtctggctc actcctgtcc ctgcttggca cacaggaggg gctcaggaat acctgtagat   6000
agagtgaagg gatgaatgaa ggaaggaatg agtgactgga caagccagcc aggcagggca   6060
tcagaaggaa gcacctgctc agatacaggc tctggctctg agaccaagtg tgcttgagtg   6120
agtgtcctgg tcttgttgag cctcaatttc ttcatctata aaatgggctc acgatagttg   6180
tcctcatgag aggtgttggt cttataggcc agaaaacccc acacatagca ggtgctccgt   6240
aagctgtctg ttaaaaaatg gatgggagga agctaattag ttagctgggc agaggttcgc   6300
tttggagacc tgtctgccct ggagagaatg actaagcccg tctttcactc ctttcctctg   6360
ttcattcatt cattcattca ttcatccagc aaatacatct tgagcagctg ctatgtgcca   6420
ggacctgttc caggcatctg ggcctcagca gttaccagaa gggagtccct ccgccctaga   6480
gcttttgtcc gagtgacatc attccacacg cagtgctttg aggccacttt gtgagactct   6540
gatacccaca atgacaagta atccagcagt gggaactgtg atgagctccc ttttacaggt   6600
gaggaaactg aagctcggag aggtcaagtg atccgtctgg ggccacgcag ttactaaatg   6660
gcaaagtcaa gattcagact ccaagcctgt caccactgtg ccatcttgtc ctgctgagtt   6720
ccaagggata tggcgttgag aagggggggtc ctagggagag ggcatggtag cccccaaagg   6780
gatgaatgaa ctcaaatgga tttaaaagca gatggttgga agtctagcca cattcacttc   6840
ctgtagcgtt gtggactcag ttaaatctca ttctttctga tcttcagttt gttcatctgt   6900
gaaatgataa caataacacc gacctcaaat gagagagaaa tgtgaaagtg cttagcatat   6960
gataggtatt ggataaatgt cagcccttac ctcctttccc ccgggactga ctttatacat   7020
ctgggaatgg agacaataat atttaatgtc tatagttatt atttggatta aaatagatag   7080
aaggggccag ccatggtggt tcacgcctgt aatcacaaca ctttgggagg ccaaggtgtg   7140
tggatcacgt gagcccgggc attggagact aacctgggca gtagagtgag actccatctc   7200
tacaaaaaat aaattttaaa agtaggaatg gtggtacatg cctgtggtcc cagcttctgg   7260
ggaggctgag gtgggaggat tgcttgagcc tgggaggtcg aggctgcagt gagctatgat   7320
tgtgccactg cactccagcc tgggtgacaa agccataccc tgtctcaaaa caaaaaacaa   7380
ccaaatggga ggtgctgtgt gaagtgtgcc atggagggta ggcattactg atggtacatt   7440
gcaggcatta gcctcagtca taattccaag cagttaaccc ctgaggcagc agcttactgt   7500
tggcacagac tggtgttgag gtgggctggg acagaggaag gatctcaaac tggttttctg   7560
ctgccttggg ctcccttccc cgactcctgc cccatccact cataacgggc acctgccctc   7620
ttccccctcc tctgatttgg caaactcggg acttttgctc ctagaagtgg ggtagaggaa   7680
cgtatgcatg gacgagtgtc ctgtcccttc tggtccttag tctcccagct gggaggcagc   7740
ccttgtcctg acagccttct aaaggtgaca gaagatggaa atgaggtggc gaggaaaccc   7800
```

-continued

```
tttccaaagg tgaggtctct gcagtcacga gccctggttt tggagccggg aagtctgggt   7860
tccagtgcct gcccagttct gacctccctg gacctcaatg tcatcatccc ccacctccca   7920
ctgcaaactg agggaatgtt agcaagaatg gcaaagcagc cattgaacat ccttatctgt   7980
aaaatggggg taataattgc tacgacctgg gtggggttaa gctgtatttg ctccatagtt   8040
atttggtata cagtacattc atgctttaaa ctaaaaaata agttcaagtt cattgaacac   8100
ttggtgtttg ttgggcactg cactgaaggc ttgaattatc acatttaatc ctcacaatag   8160
ctctttgggg taggagctgt tattttattt tttaatattt taaaaaataa ataaatttat   8220
ttattttttg tagagatggg atctcaccat tttgcccagg ctggtctcga actcctgggc   8280
tcaagcgatc ctcccacctt ggcctcccaa agtgttggga ttacaggtgt gagccactgc   8340
acccagcctt attttttagt ttaaagcatg aatgtgctat acaccaaata actatggagc   8400
aaatacggct taaccccacc caggtcgtag taattattac tcccatttta cagataagga   8460
aaccaaggcc cagagatgag atgtgacttg tgcaagacca tacagccagt gagtggcaga   8520
tgagatgtaa agcattgatc aggcaacgtt ctcagactat agaatcctct ctggagttct   8580
ccgtggctgt gaccatcctc taggagaggg gctaggccag agagaaggcg ggcctaaggt   8640
tttgttttgt tgagatggag tctcgctctt gtcgcccccg ctggagtgca gtggtgctat   8700
ctctgctcac tgcaatctct gcctcctggg ttcaagagat tctcatgcct cagcctcccg   8760
agtagctggg attacaggtg catgctacca cacccggcta atttttgtat ttttggtaga   8820
gatggggttt caccatgttg gccagtctgg tcttgaactt ctgacctcaa gtgatccgcc   8880
cacctcggtc tcccaaagtg ctgggattac aggcgtgagc cactgcgccc ggccggacta   8940
agaatttgat gcctccctcc tcctgggctg gagctgagta gcatgttctc aagcagggct   9000
ggctgagagg gtggaatcct ggggctatgc tctgatggga aggaagcgag ataagggaag   9060
aaggacctgg agcctcctgg ggtagtgact ttgtatcctt gagctcctac tacgtgccag   9120
accttgtttg aaacccttta tgtggctggg cacggtggcc gacgcctgta atcccagcat   9180
tttgagaggc cgaggcggtc ggatcacctg aggtcaggag ttcgagacca gcctggccaa   9240
catggtgaaa ccccgtctct actaaaaata caaaaattag ctggcgcagc ggtgggcacc   9300
tgtaatccca gctacttggg aggctgaggc aggaggattg cttgaacctg ggagacggag   9360
gttgcagtga gccaagattg tgccacttat actctagcct gggtgacaga gcaagatcct   9420
gtctctctct gtcacacaca catgcgcaca cacacacaca cacacaagaa agaaaaaaaa   9480
gaaacccttt atgtgtgctt aatctccatg acattcccat gttgcaacaa ggaaactgag   9540
gttctgggag ggaagtgacc tgcctgaggt cactaagcct ggaagggtca tttagatgta   9600
attcacatac tcataactca gtcttttaaa acgtacaatt cagttggttt cttagtgtat   9660
tcagagttgt acagacatca gcactatctc attccagaac attttcatca ccccaaaaaa   9720
ggactctgta cccattagca gtcaccactc cccactccca gcccctggca acaactaatc   9780
tgctttctgt ctctgtggat ttgcctgttc tgggcatttc atataaatgg aatcctgcaa   9840
tatgtggcct tttgtgtcta caaggtgcat gctcttaacc attaagccac accgcttctt   9900
ggtggctcct acccaggggc cgggaccctt ggaaatgact tggtccctgt gaaagctcag   9960
aggggcatct gtgtgtgctg tcagccggcc tccctccagc caagggcttg cagaatgacc  10020
aaatgactgc cgtggccacg ctggccttgc cctccgtggg gcgcggtgag tcaccccaga  10080
cctgccctgc ctgggtggtg tgagtgcatg gggtgggggc ccagcaggac actggggctc  10140
tgtctgtcct ggacaggcgg ccactgtgca gcaaacagga agcgggctgg gccgagacct  10200
```

-continued

```
gctaggtaaa tacaggctgg ccagggaagg tgctgggcat ggcatgatgc ccccctactg  10260
ctgccgcctg ccaagtgcct gggagccgtg gggtagcctg gcaggcagta ggtttcgcct  10320
ggccaaggag ttgagctccc agccggctgt tcccagcagc cgccacttcg aggtggctgc  10380
cagagtctac ctccaaggct ctggatctgg ccgctctgcc ttctctagga gtcattgcct  10440
tccttggtcc tcagtccttt tgttcatctg ttcccctaat gatactaata aatagtacac  10500
tgatactgat gattccaaca gcagccatgc ttgactgaat gcatgctctg taccaggcac  10560
tgggctcagt gttttgcatg ctttatctca tgtaaccctc acgacagttc ccttggggta  10620
ggtgctagga tcattgccat ttttcaggtg aggaaaccga ggcatgggca ggccaggtga  10680
cttgcccaga gctggtgaac tggtggttcg tcagggactg cgacccatcc cccactccat  10740
tctttctcca gcttctccct cccagagttc ccttgtcttt gtaaagtgtc catcaaaggc  10800
gcaggtcccg gggatgcatg ggttctaatc ctgcctcccc ctttctggag caaggcaatg  10860
ccagacaaat gacttcgcct ctctgagcct cagttttctt acctggaagg tggggagggg  10920
gtggacaggt ctgggatttt ctctctagta acagcaaagc tcagagtcct tgtcttccta  10980
gtaccttcct atccacatgt ccccggcaag actgatttgg aatggcaggc actcacagtt  11040
gtgtttattt gagggtacca caggaagtgg gggcccccaa attggctaag gagccccagg  11100
gtggagggag gtagaagcac actgggtctg tctgggagcc tgagcacctt ctctgtgggc  11160
tccttcctac ccatggattc caaccccac ccacctcccc actgcccacc cactcaccca  11220
tctcttctgc tttccttctc cctgtgcccc aggccacacc attcctctgt gcaccctgca  11280
ctttcccctc tacacctttg tccttgacac ctcctctgcc ctttatcttc ctcctcctcc  11340
tcctcacagc ctttccccct ccccatcagg attctggctg cccttgctct gcaaccctgc  11400
ctggaacttc aggtccctga tcttacagcc taaaaaaacc aaatattcat tgacacctca  11460
ttttgcttca gcaccatgct gaatgctggg gacacagggg acacgaaata gtccctacca  11520
catggaacta aaactctgga ggtgaagaga gaagatgaat caaagaataa tatataggcc  11580
gggtgcggtg gctcacacct ataatcccaa cattttggga ggctgaggca ggtggatcat  11640
ctgaggtcag gggttcaaga ccagactgac caacatggca aaaccctgcc tctactaaaa  11700
atacgaaaaa ttagccgggt gttgtggtgc atgcctgtaa tcccagctac tcgaggaggc  11760
tgaggcacga gaattgcttg aacccaggag gcggaggttg cagtgagctg agatcatgcc  11820
actgcactcc aacctggggg acagagcgag actctcttga aaaaaaaaat acatatatag  11880
aaaagtttaa tcgtgggaag tgctgtaaag gaaggcacat gttactctaa gagtaaagag  11940
caggggaaac aggagggctt ttcagaggaa gtgcccttta acatgaggcc tgaggagtaa  12000
gtgggagcca gccagcgaag ggaagggcat tccaggcgga gggaacagcc taggcaaagg  12060
cctggaggca gagagagcca tcagccttcc ctcctggact gcgagttctc tgaggttcca  12120
cacttttatg tctcccctgt gccctgcaaa caggtgccac tgcattgatg cctggtggaa  12180
tgaattgatt ccagaaggga gggaaccggg agaaaccagc tccctggatt cctccccgct  12240
ggggcggagc aggtttgcat gcccaaactt gcccccagat ttaagcagct ttccttggtc  12300
acgtaatcag gaggatggga tttgacaaat gtttgccagg gtttccatga gatcaggcaa  12360
agccgcgggt aaccccgagg atgggcccct ttttccaccc tccgcaagtt ggggcatggg  12420
gacggagcca gagacctcca ccgcctttga atccgggatt ctcagagaga agccatctgt  12480
tgtgcaatct gctgtttatt gaggctttct ttatgccagg cacttgactc aaggtatata  12540
cctctcacaa cgaccctatt acgatccctt aatagggcag ctgagggccg ggcgtagtgg  12600
```

-continued

```
ctcacgccta taatcccagc actttgggag gctgaggcag gcggatcacg aggtcaggag  12660
atcgagacca tcctggctaa caccatgaaa ccccgtctgt actaaaaaaa tacaaaaaat  12720
tagccgggcg tggtggcggg tgcctgtagt cccagctact caggaggctg agcagaagaa  12780
tggcgtgaac ccgggaggcg gagcttgcag tgagtggaga tgcgccactg cactccagcc  12840
taggcgacag agggagactc cgtctcaaaa aaaaaaaaaa aaaaaaaaaa atagggcagc  12900
tgaagaaagt gaagatcaga gaggttgggt aacttgctca tactcaccca gcaagtgagc  12960
tgtgggtctg ggatctgacc ctctggtctg cctgacgtca aaatgtgccc caccggctca  13020
gggggccatg agagcagaaa gccaggtttc tggaaagcct ggggtctctg tctagggcag  13080
aaaggaaggt ctggggaccc tggctcagcc ctgtatctca tcaccctact caggactcct  13140
gcacccctta acttgcccac tcctgagccc ttctggtcta tgcagttctt aacaccatcc  13200
gacatgactc tgctgcttga tttgtctagt ttattgtttc cccaccagaa ggtctgcccc  13260
caaagggatt gatatctgtt ctgttcacat ctgtgtccct agtctagcac agtgcctggc  13320
acatagtagg tgctcaataa atgtgtggaa taaataggta gctggcttct actgctgccc  13380
cttgggccct ttccagagga agatgcagat tctttgtcca tcctacacaa ctgccatctc  13440
tgtgtggacc accattcagt atatatattc taaagaagag tttgaatata aacctgcttt  13500
tgaatatata ggatttaaaa ccaacatatt caaaaaccgc tactttggct gggcgcagtg  13560
gctcatgcct gtaattccag cactttggga ggccgaggcg ggtagatcat ttgaggtcag  13620
gagttcaaga ccagcctggc caacatgtga aaccccgtct gtactaaaaa tacaaaaatt  13680
agctgagtgg tagtggcatg tttctgtaat cccagctact tgggaggctg aggcaggaga  13740
attgcttgag cctgggagga ggaggttgca gtgagctgag attgtgccac tgcactgcag  13800
tctgggtgag agagtgagac cctgtctcaa caaacaaaca cccgctgctc tgaatgaacg  13860
ctgttgtgaa gatgtcagtg tgtgaggatg ttcacagtcg tgcaggaacg ttcttgggtg  13920
cctccctgat gcacacctgg tgcagctggg agcttcccca ctgtggaggg gctcctggta  13980
ggaggcattg tgagcccgtg cgggaacgaa gggcccacca tgcctgctca cagtgggcac  14040
acacacatgc acacgcccat ggaggaaggt gggaagaaat gtacatgaca gtcacacgca  14100
gaggagacac atgtggactc acacccaggc tctcagcctc tctccctgcc tgcatccccg  14160
acttccctcc ctcctaaaac tggcatgagt ttggaatgtg taataacagc ctttagggca  14220
aattagaaca gggagtaaac tctttctctg accacagaga acaggacagt gtttggggag  14280
ggaattgcca cagagcagca gagccgggtg tgtgtgtgtg tgtgtacaca tgcctatgtg  14340
tatgtgtaca cgtgagctag tgtgtacaca ctcctgagtg ctgtgatgtg gaaggagccc  14400
agggctagga gtctagaggt tttcttcaaa gccatttgct ccctagctgg cctctcagag  14460
cctccgtttc cttagctgta aagtgggagc aatagcctag ctttgttcag gttcttcggg  14520
ggattgaatg agagaggggc ttggtggatt ttagcatggg ctataaaatg tcaggctgta  14580
gtgctggcac gtgtgtgcat gtgtgttttg gggaagggga gtaaggagga caggtaaatc  14640
aggaccatat catagtggtg atgatgataa ttaaatgtga caagatccaa catttatcaa  14700
atatttctta ggtgcccaag aaacacttga cctgccttat ctcccagaag ccctacaagg  14760
gaggtgctat tattgcaatc cccattttac aagtagagaa accgaggctc agagagatga  14820
gaatgggcgg cagtaatcat cccttcctcc tgggggtggt tgtgaagctt gaaggagaca  14880
ctgtaagcgc tcgggtggta ccctggtact ccatcactaa cctgctgtgt gacctcaggt  14940
aagtcgctta gcctctctga gcctcagttt cctcatctgt aaaatgggaa tgattgcaat  15000
```

-continued

```
acctacctcc agggcagatt ttctcaacct cagcgctgtt gatgttgttg actgggttat  15060
tctgtgtggt gcggggctgt cttttgtttt ggaggatgtt tactaccatc cggcatggcg  15120
gatcccagca aaggcccctg tgcaggcctg gtgaggtggc cgagcttcct ggtggggagg  15180
ccttcccccct ctcctccctg gtcaatctat ttgagggtga ggatggctcc ccttcaccct  15240
cacctggcac ccaggacatc cccagtccat ggagggattc aatctgggct ctgcagccag  15300
ctgcccgcat ttcagtcctg gctctgtcac taacctgctg tgtgacctca ggcaagtcac  15360
ttagcctctc tgagcctcag tttcctcatc tgtagaatgg gaacgatcgc agtacctact  15420
tccagggcag atgttctcag tctcgacgct attgacattg tgggctgggt catttttttg  15480
tggtgtgggg ctgtcttttg ctttggagga tgtttagtgc catccctggc cttgatctac  15540
cagatgccag tagtgctccc tctcctgtac agttgtgaca acaaaacatg tcatcagata  15600
ttgccaaatg tccttagagg aggagcagaa ctgtccttgg ttgagaacca ctggtctgga  15660
gtcatgatga gggctggatg aggccctgtg ctgggcacag cctgagctac gtcatcaggc  15720
gaggatggtg atttagttca taattattat ttcatcctaa ttagaatgct aatcatgatc  15780
gcggcgtgac ttgccgaagg ccacacagca gccatacagg ttgacagttg ctgggagagg  15840
atttgaacct gggattggct ggcaccagag cccccatttt ggagtcccca ggaacctggg  15900
gtgctgtcca ggcttagggg agggctatcc tcctgagggg aggagggtgc aggcatggtg  15960
ggggatggaa ggaccttctt ggctgccttc tctggccttg ggagctccct gggatggggt  16020
tccattagcc cctgaggtgc catggtgagg ggtgcagtgg atagaagggt actggaaaca  16080
cagagggtgc gcctgatgcc tcgtctcccc ctgacctcag ggcccccagt gaggtggaca  16140
gggccatgcc caggagagtc taatccacct cccgccaatg cctgtgcccc tgcagatgcc  16200
cctcctgcct cagcaacccc ctggccccca ttcctgcaga gcaaagccca aatgcatgtg  16260
gcagccatga gggactaggg atccagatcc ccctctcctg tctggccagt cgaaaggact  16320
tcgtgtctcc agaggtccta ctaggtgctg gaactgagta ggtgcctcac atgctggagg  16380
accctaggag gaggcgtggt cactccagtc ttacaggtgg gaaaaccacg gggcagacag  16440
aggaagtgat ttgcccatgg tcaaacggct aatgaccagg gccaagagag gaactgggtc  16500
tcatttcaga acctggcctc ctaacttctc tttcttcgtt tggttataat aactgaaagt  16560
cccactctat ttacagatga ggaaactgag gctcagagag gctaagcaac ttacctgagg  16620
tatttatttt tagatagagt cttgctctgt tgccctggct ggagtgcagt ggcgccatct  16680
tggctcactg caacctctgc ctcctgggtt caagtgattc tcctgcctca gcctcctaag  16740
tagctgggac tacagtcacg tgccaccacg cctggctaat ttttgtattt tttatagaga  16800
cggggttttg ccatgttagc caggctggtc tcgaactcct gacttcaagt gatccacccg  16860
cctcggcctc ccaaagtgct ggggttacag gcgtgagctg ctgcactgag ccaaaacccc  16920
actttaatcc cagaagtggc actggatata tctgacctca cttcccactg cctgcaaccc  16980
tatgaagaag tgactacaat tgtacccatt ttgcagagga ggaaactgag gcttggggag  17040
ctcaagtaac ttacctaaga tcacactaca tgtaaatagc agagctggga ttagaaccca  17100
ggcctgaatg actccaaagg ccaggctgtc tctccctttt ggtgtccaaa gggaagccca  17160
cccccagtgg gagctctgac cctctgtgtc ctgctgcgcc cactaaggga ggcctcttgc  17220
tgtgtcccca cctctctggt ccaagtcttc cctcctggaa gccacagaac aaacaaggtg  17280
ggaactagtt tatttgtttt tctacgtgcg tattgggtgg gaagggtgag atgtacaaga  17340
gagggctttt cagacatgcc cctgcctccc gggtggggtg gtaagagttc caggaaactc  17400
```

-continued

```
accccttggtg cccagccctg cctggctggc accatgctac agagagcagg gcactgacag  17460
ccaaccagtg gggccttgcc cctcccttgc cctggctcct ggctaagcac tggacccggg  17520
agccagagag acatggttca agtccagctc ttcttcctgc aagctgtttg ctgcctttga  17580
aagctgcttc ctcatctgag aaatgggaac aaatgacatc tttgtcataa agtttttcat  17640
ttgtgtgagg actcagggat ggacaagaca gatacatttc ctgcctcctg gcacccacag  17700
cctgggaacg aaccatcccg tgaacagctg ggataaagct tctgaggaga ggagcatgga  17760
tcctgggagc gagtgtgtgc aggccaggga gggctttcca gaggagccca gttgagctgg  17820
aacaccagtg gggaggagtt gaccagcaaa ggtgcaggga gggatcagca ctttgcactg  17880
gggagcagag tttgtgcact ggggaagtca actcaagtat tggagcctca gtttcctgtt  17940
ctgtaaaatg ggttcatcat gacagtgttt gatgaggaaa aggactgccg gcctacacag  18000
caagtccaca tggattttct gagcccctcc tgtgcctgaa gcccacggtt aatggttctg  18060
ccttagcagg tgcttaccac gtgccaggca ctgcactgca ctggccactg gactgcatgt  18120
tctgtccatg aggcttggat atccccatct tacagatcag gaagctgagg ctatgaaatg  18180
tcgacttgct caatgtcatg gaatgactaa gtgtggagcc tggatttgaa cttggctctc  18240
tggggctcca aagctggctt tcttggtcag cagtagggtc tgggatccaa gtatggggtc  18300
ccagcttgac cctgaagtcc accctctttc agctaatgcc cagggtagtt ggacctgggg  18360
ccaatttgtg tttccaggtt cgtgaaagag gctcctgttg cagttcccgc ctgaggctgg  18420
cggccaacca catctgggag tggcctccct gtgcccctgt cattacaacg gtggctttga  18480
agcagctggc agcactgctg cttgtccacg tgggaggggg cttcctggag cccccgcccc  18540
tggccgggtt ctgcctgact cccctttcat tcccttgcag gctgagcagt gcagacgggc  18600
ctggggcagg catggcggat tccagcgaag gcccccgcgc ggggcccggg gaggtggctg  18660
agctccccgg ggatgagagt ggcaccccag gtggggaggc ttttcctctc tcctccctgg  18720
ccaatctgtt tgagggggag gatggctccc tttcgccctc accggctgat gccagtcgcc  18780
ctgctggccc aggcgatggg cgaccaaatc tgcgcatgaa gttccagggc gccttccgca  18840
agggggtgcc caaccccatc gatctgctgg agtccaccct atatgagtcc tcggtggtgc  18900
ctgggcccaa gaaagcaccc atggactcac tgtttgacta cggcacctat cgtcaccact  18960
ccagtgacaa caagaggtgg aggaagaaga tcatagagtg agtattgtta gcttcctggc  19020
ctgtggtctc ctcctctgta tccattcacc cattcatcat ccacccctct atctattatc  19080
cacccatccg tcgattcatc catccatcca tctgtccatc caaccatcca tacatctatc  19140
catccatcta ttcatctccc tatccatata tcatccgtcc atccatccat ccaaccaccc  19200
atctattcgt ccatccatcc aaccatccac acatctatcc atcaatccat tcatctctcc  19260
atctctatat cctccatcca tccatccaac catccataca tctatccatc gatccattca  19320
tctctccatc catatatcat ccatccatat atcatccatc catacatcca tccatcatcc  19380
agccatctat catctatcca tctatccaac catccatcat ccatcatcca tccattcatc  19440
tattcattta tacatcatcc ttccatctgt ccatctattc atctatccat cattattcca  19500
tctgtccatc tatctactat ccatccatct atccatctac ccatcatcca tccatccatt  19560
catccatcat ccttccatct gtccatctac tcgtctattc atcattccat atgtccatct  19620
atccattaat ctatccatcc atccatatat catctatcta tccacccatc atccatccat  19680
ccatctaccc atctatccat catccatcca tctattcatc atccatctat ctattaatcc  19740
atcatccatt actctaccca tttacccctc tgtccaccct tccataggac atttgtctgt  19800
```

-continued

```
tcatccattc atccatccac ccactcattt atacaatgca tccatccacc cactcattta  19860
tacaaatgca aatgcattta tacaaatgca aactcagcca tttacccatt tacccattca  19920
cccttccacc cactcattta tacaactatt tactcatcta actctccatt cattcatctg  19980
cttttttttt ctttttgaga tggagtcttg ctctgttgcc caggctggag tgcaatggca  20040
tgatctcggc tcactgaaac ctccacctcc tgggttcaag caattctcca gtctcagcct  20100
cccgagtagc gggattacag gcacccgcca ccacacccag ctaatttttt ttgtattttt  20160
agtagagaca ggttttcacc atcttggcca ggctggtctt gaactcctga cctcgtgatc  20220
cacctgcctt ggcctcccaa agtgctggga ttataggtgt gagccaccgc atcccgcctc  20280
atcttttttt attcacctac atatccacgt actcatctgt cccccattaa tctacttgtc  20340
tgtccatctc ttcacctaca catccagcct tccatttgtt tatcttctta tttatacatc  20400
tgttcatcca tccatccatc catccattta tccatctatc atctactcat tcatttaccc  20460
atctttacac ttttttgtcc acctatccaa tctatagatc cattgtccac tcattaaaat  20520
atctatctac tcatctaccc atctgtcagc catctgtcca gccatacacc catataacca  20580
accttccatt catctaccat tttctcatct gaatgtcatt tcatcttctc acctacccac  20640
tgtttctagt catctagcca ttcagctatc aaactattca tcattcattc atttattcat  20700
tcattcattc catttctcat gcttgattgc tcacctgcct gctgtccttc tttccttcct  20760
ctccttctct cttctaacca ccaattcatt cacccagatc tctgtccatc catttgtcca  20820
ttcactcttt tgtttgctta gtcactgact catttattca tttgctcatc ttttcttcca  20880
tttttgcatc tattcatcca tccatctccc taccttctct tcctggcaca catccagctg  20940
cccctcctgg gtcttcttca atcatcacct ccattcctgg ccatccagtg gctttcctga  21000
ggcttagaaa gagctggaaa ccccaaggca ttcaaccttc tttcccataa tgacagcctt  21060
gctgaaagaa aagacagact ggagagaagc cctggatggg gccacagcat gtggccccta  21120
tgacgcattc catgccaggc ctagctgggg acagggagcc tccagccccc ttgaccacct  21180
tgtctggtcc ccatcctccc ccagtgtgtt atgctggcat ctgcatgtgg tttgtgtggc  21240
actctgcaaa ctcagacatc ccgggttctg tttccagcat gactctattg tctgtcacct  21300
gcagactccc tgctttgtga ggttgagccc tccctcctgg tcctttagga agcccaggga  21360
cttccacaag cttttggcag tttggaggag ggagcagggc ttgcagtctc ctagccagct  21420
cctcctgagc ctcagcaggc cctgctgaac tgtatccttt ctatgtcccg gccctgctgt  21480
ccctaatgtg ccctgaattg accctttcct caactgctcc atgaaatctc ctctcggtgg  21540
cctgtgtgtg tgtcctggag gatggtgctg aggtctggag atgacctgga cttgcgtgtc  21600
ctcctctgtc cccctgctgg ccacagattc atttatctct tggatggagc cgattcacct  21660
tcacagccct tgcttggtca agagccgccc cctttattta ttcacagtca ttgattcatt  21720
cagatgtctc tttttctttt tttttttttt gagacaggtt ctttctctgc cactcaggct  21780
ggagtgcagt ggcgctatct tggcttactg caacctccac ctcccaggtt caagcaattc  21840
tccagcctca gcctcctggg tagctggagc tacaggtgtg cacgaccaca accggctaat  21900
ttttgtattt ttagtagaga cagggtttta ccatgttggc caggctagtc tcgaactact  21960
gtcctcaagt gacctgccca cctcggcctc ccaaaatgct gggattacag gcgtgagcca  22020
ccgcacccag ccagtggatg tttcttgggt gcccactgtc tgccagtcag tggggttggc  22080
cctgaggctt caggctgagc cagaccagat ccacttctac tcaggcggca ctttccgttt  22140
agagggtgag acagacaaga agcaagtagc tgagcacatg gatgtgccat gtgagttggg  22200
```

-continued

```
ggaggtgctg aagttagaga gtgggtggat acaagaaagg taatccagga gggcttcttg  22260
gaggagttga catttaagcc caaagctaaa ggtcatgaag gggcagtcac agagagggag  22320
ggaagggtgt tgtaggtgga gagaagtgtg agtgcaaggg cctaaggctg gagaggctct  22380
gcagatgtcg ccaaggaata gggcctcaca gttgtctgtg ctgaaaaatc tgtacaacct  22440
ctgctcagag gtggaaacta agggccagag cagcagagtg cccagtgttc ccatccttct  22500
gtccccaagc cttcccaggt cctgttgaaa gctggtgggc tctgtatctc ccattcccct  22560
cccgcaagcc ctcctcccca cccctacccc aggaagtcca ggctggtgga gtaagtgggg  22620
cacggctgag ccctgaaggc tgcctcagtg agatctggtg gggcagtat tgctttttat  22680
tttttggctc aaaggtcaaa gttcaggaag aggtaaagtg gggctgcct aagtgccctc  22740
attagaggct gtatctgtgc ctgtgcccct gtcaacagga gagcacgtct taccctactg  22800
tggatgctaa tgatcccctt tgccagtacc tgccctgaga tggaaaatct caacccctgg  22860
cgaagaggaa gggaggagag tggctgtccc cttctcatgg caagacaggc tgggtacagc  22920
cagatgccag ctttgtccac ccttgcaacc ccgtcccacc tgcttccaca acctgccctg  22980
gcctcagttt ccccaactgc attccccttc ccctctggcc ctgctgcctc ttgttagggt  23040
tttctctgtt cccctactct cccctcttct ccctcccaga ccctgtgcct ccatcttcct  23100
ccttctcttt agtctcttat tcattgaaca gagtcttact gcatcccaag atgtgccagg  23160
cactgggcca ggtaagaatg tgacagagag agcattcctg cctcatggtg gccctgggct  23220
agctctttct ctctcagaac ctagcacata ataggtgccg aaataatgtt tgttgaatga  23280
ctgaatgagt gtctccaagc cctccagctc ttagtgtctg tttccttcct ttctctctct  23340
atctcttctc ttcccagccc tctctgtgcc acacccttcc gccatctgcc tctgtagccc  23400
cacatctctc ccatgcacat acaagctcca gacacacagt aggcactcat taataatggt  23460
aatatcaact aacatttatt gaatgtttac cgtgtggtgg gccatgggca ggtacatatg  23520
agcatggcct catttgtctc aaatgtttgt tgaatgaata aattaatggg ttagttatgg  23580
aatgaatgga tgaaatgcct catcttttag tctgctgttt ctttatttta tctttgtttt  23640
tgtctctttc agtttctctg ccttagtaag tactcaataa atgactaata tatgagtggg  23700
tgggtgagtg gatgggcagt tggatggatg gatggatgga tggatggatg gatgggtggg  23760
tgggtggata ggcagatgga tggatagacg agtgatggat ggatggatgg atggatgggt  23820
gagtggatgg atgggcagat gggtggatgg atgagtgggt ggatggatgg atgagtagtg  23880
gatggatggg tggacagatg gaggagtgag tggatgggta gatgaatgga tgagtgatgg  23940
atggatggat ggatggatga gtgggtggat ggatggatgg atcagtgagg gatggatgga  24000
tggatgagtg atggatggat gaatgggtgg atggatgatg ggtgggtagg tggatgggtg  24060
gatgctgggt gggtggatgt atggatgagg gatggatgga tggatgggcg ggtaggtgga  24120
tggatggatg ggcgggtagt tagatgggtg gatgaatgga tggatgggtg ggtggatggg  24180
tagatggatg gatgagtgat ggacggatgg ataagtggat ggatgggtgg atggatggat  24240
gagtgatgga tggatgagtg atgaatggat ggatgggtgg gtaggtggat gggtgaatgg  24300
tgggtgggtg gatggatgga tggatgagtg ggcagatgga tggatgagtg atggatggat  24360
ggatggatgg gtgggtggat gggtagatgg atggatggat gagtgatgga tggatggatg  24420
ggtgagtgga tgggtagatg gatggatgga tggatgaatg atggatggat gggtggatag  24480
atggaggagt gggtggatgg gtagatggat ggatgagtga tggttggatg gatagatggg  24540
tggatgggta gatggatgga tggatggatg agtgatggat ggatgggtgg atagatggat  24600
```

```
gagtgggtgg ataggtagat ggatagatga gtgatggatg gatggatgga tagatggatg  24660
ggtcggtgag tggatgtgtg gatggatggg tggatagatg tatgggcagt ctgtgcattt  24720
ctttctgttt gtctccaccc aacacacagt aggtactagc tatagtttgt tggataaaac  24780
attacttagt ttttacatct gccccaacta cctcaccctg ttccttgtaa ggcttcagct  24840
gcctgcccgc caccacagtc tctgggtccc taaggccagg gacagtgggg caggcagggg  24900
atgagccctc ccatcaactt gcctccctac ctcctccagg aagcagccgc agagccccaa  24960
agcccctgcc cctcagccgc cccccatcct caaagtcttc aaccggccta tcctctttga  25020
catcgtgtcc cggggctcca ctgctgacct ggacgggctg ctcccattct tgctgaccca  25080
caagaaacgc ctaactgatg aggagtttcg aggtgagcca cccagatggg catagccagt  25140
gggacagcca ggggtgtggg ggaagcctgg cattgggggc cccctttccc ctcagcttct  25200
ttctttgggt cggtggactg cattggcctg gaaagtgcac tggacaggga gtctggtcct  25260
gtgtgtcctt caccatgtta cttaacctct ctgtgcctca gctacctcca tttattcatt  25320
ctttcattca ttcagccctt atgtatgaaa aggttagtgt agtgggtaag cagagtccac  25380
ctacctgggt tcagattcta cctttaccag ttaagcgatg tgtgacctct ctgagcctcc  25440
gtttcctcat ctgtaaactg gggaataatc atagcatact cctggctctc atcccacaga  25500
gagcccagcg caggcagctg gagtcctgga gctcctgctc ccctgaggga aggtctggag  25560
ggatgggcag gtgtctgggc tggtagtcct gattctactt cttggggtct gctccacccc  25620
agcctagctt tagggctcca cttcctaggc tgaagcccca gcccagagag ctaacccttc  25680
agccttgtcc agattcaaaa cacccacctc aggacaccgg caccctccac agccccaggc  25740
cttacctgtg aacacctgca cccaaatcag ccacctgcaa tgtgctgggt tctgggtaag  25800
ccattattaa actggccgtg atctcacaag tcaagatacc atgtcaagaa gtgtgacacc  25860
aaggctgggc atggtggctc acacctgtaa tcccagcact ttgggaggcc aaggcaggag  25920
ggttgcatga gcctgggagg ctcaggctgc agtgagctgt gatcatgcca ctgcactcca  25980
gcctgggtga cagacaggaa aaaaaaaaaa aaaagaattg tgatacctgc tatgaagaag  26040
ggcccatctt ggaaggcgga ccatggttgg tctacagcct aagtctgagg aggcttcagg  26100
gatgtcagaa gaggcttttt tttttttttt tgagacagag tttcattctt gttgcccagg  26160
ctggagtgca atggcatgat ctctgctcac tgcaacctcc gcctcctggg ttcaagtgat  26220
tctcctgcct cagcctccca agtagctggg attacaggca tgcgccacca cgcccggcta  26280
attttgtatt tttagtagag acggggtcgc tccatgttgg tcaggttggt cttgaactct  26340
cgacctcagg tgatctgccc gccttggcct cccgaagtgc tgggattata ggcatgagcc  26400
actgtgccca gccagaagag gacatttttt aagacttcag ttactttaag taaattaagt  26460
tcccaaacag ggtgaacaag tctgtgctac atcatccaca tatacctttta tcaacctgtt  26520
tttttttttt ttttcttttt tttttttgag atagggtctc attctgtcac ccaggctgga  26580
atgctgtggt gtgatcacag ctccctgcag ccttgaactt ctggcctcaa gcaatcctcc  26640
tgcttcggcc tcgagagtag ttgggactac aggtgcaagc taccatgcct ggctaaattt  26700
tttttttttct tttttttaa gagacaggtc tcactatgtt gcccaggctg gtatcaaact  26760
cctggcttca agcgatcctc ctgcctcaac ctcccaaagt gctgggatta caggcatgag  26820
ccactgaggc tggcctcaac ctcattctta ccctgaaaca atacgatgca gtatcattgt  26880
gtccatcagg agacaattac tggggccggg tgcggtggct catgcctata atcccagcac  26940
tttgggaggc tgaggcgggt ggatcaccta aggtcaggag tttgagacca gccttgccaa  27000
```

```
catggtaaaa acctgtctct actaaaaata caaaaaaaaa aaaaaaaaag ccaggcttag  27060
tggcacacac ctgtaatttc agctacttag gaagctgagc caggagaatc acttgaacct  27120
gggaggtggg ggttgcagtg agccgagatt gcaccactgc actccagcct gggcgaaaga  27180
gcgagactct gtctcaaaaa aaaaaagaaa atacaattgc tggatttatg aaaaatattc  27240
attcatggtt cctggccacg cgacgtggcc tcgtttggag gcacaagttt agagctgtgg  27300
gaggacgggg cttctctctg ctcctggagt agctcagtga tggcatgagt aatctcattc  27360
ggagataacc catgtttaag ccctggccaa atggcctctc ctggtccacc aagtacgtga  27420
ggcaaaagtg cggaatcttg ggtagagcg aatcctggga gatggatgct ggcacctgtg  27480
ccttcagcac caggctagct tgtcaaggcc tctggcttct tctgaattca ggactgagtt  27540
gggggcttct agcatagtcc aggaacccag atgcatgtgt gtctgtgcat gagtgtgggt  27600
gggggactct aagataggct ttggaggtgg gtctctgaaa ttgcagaggc tagcgtatgt  27660
gcatagaggg agacttactg tgaggtccat gatactaatt aagtgccagg gcccctggct  27720
aaggcccttt ctgaggtcct cgacctagtc tacgtcccac aaaacctgga tccgtccctg  27780
catggctaaa aggtcatgag ctcatctgat tatcagggaa gtctgggacg ccctcctgtg  27840
cccccacctc ccctccgcag agtttcacaa cctccaattt ggcaattgtc aatttagagc  27900
ccctggctac agcaccccac cctgggcaga gccacttcgc cacctggtgg ctggttcctg  27960
gaactgcatg ttccacctca tctctgggaa gatgctgctc ctgacatctt ctcccaggac  28020
ccaggcgtcc cctccctggg tctataacct gtgtctgaaa gcccgaatcc agggtctcta  28080
gttccacttt gggtcaccta tggtttggaa ttacctgggg tgcccagctc tcgccttcat  28140
tcaatgtgtg ttaactcagc aaatggttgt tgggcaccta ccacatacca ggcactgtgc  28200
ttggcagagg ccgaatgata gtgagcaaag cagacatcac cctgccctca aggtgcccac  28260
aggctcctgg acaggaccat cattgaccaa gcaaccacat aaataagcac acagttatga  28320
actgtaacag gtgtcaacaa aaggctgtac tggaggattt gacctagtca gggaaaatcc  28380
aggagagctt cctggaggag gtaacacttg agcagagtct gagtgagttg cagttaacca  28440
ggtgaaaaga ggagggaaga atgtttcaga ttggggtggg ggttcagaga cagcaggtgc  28500
aaagaccctg tagttcaccg tggtctattg cagtctgaaa tgaccattcc agctgctatg  28560
tggaaagtgg ataaaggaag gccagagagg ctgggggaaa tgagggaaat aaaggaggtg  28620
tcttaggcat gtgagaggga tggtggctgg gccacattat tccatgagag gtttggtgtc  28680
gcctctgagc tgggcgccag gtggacagcg ggaaagcaac tgggaacaag acttgtccca  28740
aacaaccctg ctcctggaag ggctgagact agaattcagg tctcttgagt ctgccccact  28800
gattcccggc atttagggag acggttccta aatcccgtct catggattga taacagcaac  28860
agtaatattt atcaaagact gctatctgcc tggtactggg ctaatcaaca aacactgatt  28920
agctctttga tttcccttca tagctttaat ttagccagaa aggaccctaa gcagagaaat  28980
ggtcatacag ctgtggggag caaagccagg cctcaaacct gaggtgcctg gcttcagaac  29040
gggcacctga acccacacct gcgtctccca ccctctggcc attcctgagc ccctggctga  29100
ttttgccctg tccttgattc acaggggagt tttcaactta ctcttttgag atataaatca  29160
actcaggtaa ccataaaaat agctacaaca gaaagaaact tgcaaagaga catcagcaag  29220
cgttagtgag aggtgttaag gacccgctag taccaaacgg agagttgact tcatgagaaa  29280
gattcgatag tggatgaaac cttcagggtt attattgttg caccccctag aacccccaag  29340
attctctcct ggatccccta aggtcagttc acatccactg tggcacacag tcccacactt  29400
```

-continued

```
tggggaacgc tgcacccctc cactcccttc taggggcacc agtgtaaatg cttcatggga  29460
aaaggattcg atgctctgac aggtgggtga atgctgccta gtgtgtcttg cttttacagg  29520
ttcacagtcc ctgttagtgt atgaaaggct ctgagaagtc ctgtagtaag gaattatgat  29580
tggctttgtt taacccagca ttctaaccat ttatttgttt atgaagcact ttacataaat  29640
cttttcgagg gccaggtgtg gtggctcaca tctgtaatcc cagcactttg ggaggctgag  29700
gtgggaggat cacttgaggc caggtgtttg agaccagcct gggtaacaga gtgagatccc  29760
ttctctacga aaataaaaat taaaaaatta gttgagcatg gaggtgcaca cctgtagtct  29820
tagctgctac ttgggaggct gaggtgggag gatcacttga gcccaggaat cggaggctgc  29880
aatgagctag gattgcacaa ctatacccca ggctggatga cagagcgaga ccctctctct  29940
caaaaaaaag gatattaata aataaaaata aatacaaaat cttcccaaat aagattaatt  30000
aaataaatac caatctgtag gctgaagcct ctcacatttc aaagcaccta accccatgcg  30060
tttattgtac cctctcagca ccactggagg cagaaagata gagtggccct gggtccccac  30120
tggacagatg aggaaacagg cttggagagg agatgttgac agccaggaca tctgaccccc  30180
tacccagtgt tctgtacccc gatgcctgga agttcaaggt catgggctgg agcactgcgt  30240
catcttgtgt gtctctcttg ctagagccat ctacggggaa gacctgcctg cccaaggcct  30300
tgctgaacct gagcaatggc cgcaacgaca ccatccctgt gctgctggac atcgcggagc  30360
gcaccggcaa catgagggag ttcattaact cgcccttccg tgacatctac tatcgaggtg  30420
gggccccggg ctgggcaggg gtgccacggg ggctgatgga gacgctgtcc tttgcttgtc  30480
tgactcctga gacttttgat ctgggcctaa gtgccagcat gtacccagga cctgacaaat  30540
ggatggatgg atggatggat ggatggatgc atggatgcat ggatagatgg atggatgaag  30600
gaacggtaac taccccttcc aactttgttt cgagtttcag aatagaagat tccactgggt  30660
gcggtggctc ttacctgtaa tcccagcact ttgggaggcc aagggggcca gatcgcttga  30720
gcccaggagt tcaagaccag catgggcaac atggtgaaat cctgtcttga caaaagatac  30780
aaaaaaaaaa aaataaaata aaagaaggcc aggtgcggtg gctcacacct gtaatcccag  30840
cactttggga ggctgaggtg ggcagatcac ttgaggtcag gtgttcaaga ccagcctggc  30900
caacatggtg aaaccctgtc tctgctgaaa atgcaaaaat tagccaggcg tggtggtgcg  30960
cacctataat ctcagctact tgggaggctg aggcaggaga atcgcttgaa cctgggaggt  31020
ggaggttgca gtgagccaat atcgcgccat tgcactccag cttgggcaac aagagcaaga  31080
ctcatctcaa aaaaaaaaaa aagatgcaaa aaaagccagg cttgttggtg cacacctgta  31140
gtcccagcta cttgggaggc tggggtggga agatcacttg agctcagagg gtcaaggctt  31200
cagtgagcta tgattgtgcc actgcactcc agcctgggtg acagagtgag accctgtctc  31260
aaaaaaaaaa aaaaaaagat tccaagattc tgagatgcag cgagtctagt gatcatgaac  31320
tcgggatctg gccctaagat gctgtggtgg cggatactct aaggctctat gataataagt  31380
cctgagttca caagttctaa gaggcaaagg cagcaggggg ccaagaactg ggccaatccc  31440
cagttgagat tctgtaaatc agagttgacc ttcagatgcc tggatattaa gattcaaaat  31500
ccatgaatat tatatcttga gtccaaaatt ctgggaggcc aaggtactgt tgtttcctct  31560
aggagttttc tttttttga gacaaggtct tgctctgtta cccaagctgg agtgcagtgg  31620
tgtgatcatg gctcactgca gccttgactt cctgggctca agggagtctc ccacctcacc  31680
ctcccaagta gctgggacca ccggcatgga ccaccatgcc aggctaattt ttaaaatttc  31740
tgtagagaca gggtctcact atgttgttgt attagcccgt tctcatgctg ctataaagaa  31800
```

```
ctgcccaaga ctggataatt tataaaggaa agaggcttaa ttgactcaca gttccgcagg  31860
gctggggagg catcaggaaa cttacaatca ttgtggaagg ggaagcaaac atgtccttct  31920
tcacatggtg gtaggaagaa gaagtgccaa gcaaaagggg gaaaagcccc ttatagaatc  31980
atcagatctc ttgaggactc actcactatc atgaaaacag catgagggta actgccccca  32040
tgattaaatt acctttcaca gggtccctcc catgatacat ggggattatg ggaactacaa  32100
ttcaaggtga gatttaggtg tggacacaga gccaaaccat atcagttgcc caggctggta  32160
ctgaactgct aggcttcagc aatcctcctg cctcagcctc tggagtagct gggaccacag  32220
gtgtaagtca ccaggcccag ctaattttta gcatttctat agagatggga tctcactgtg  32280
ttgcccaggc ttgcctcaaa cgcctgggct caggtgatct ccctccttgg tctcccaaat  32340
tgctgggatt acaggcgtga gcctgcgcct ggcctcctct aggattttta aagcatctta  32400
tgaatctaaa aacttctcac attcaggatt ccacaaacta ggtatccttc aggcttgaga  32460
ttctgcttct gcgatggatc ccagggaata tccaaggacc tatttgctgc ccttgggtgt  32520
cgctgggcag gactctgcct gcatccccca ccccccaatt tctacgtcct gcaccctacc  32580
cccaccccca gcaagcctgg ctaggtctct gctccgccag gaccctggat gaccgtcccc  32640
tgcccccagg tcagacagcc ctgcacatcg ccattgagcg tcgctgcaaa cactacgtgg  32700
aacttctcgt ggcccaggga gctgatgtcc acgcccaggc ccgtgggcgc ttcttccagc  32760
ccaaggatga ggggggctac ttctactttg gtaaggaggg gcctggtggg ggctgacagc  32820
atgctggaga agcatggcgg gagatagcat gatactggtt ggtgtctgca gccctgacca  32880
tcacccagac acccagggcc actctggcca tgagcgcagg cagcactctg gaccacaggc  32940
tgcacgttgg tcttggtcac agggccgttg cctctgaggt gtaagtgcca tggggagtac  33000
catggacctg gattcagatc ctcactccag ccaggcacgg tgtctcacac ctgtcatccc  33060
agcactttgg gaggtcaagg caggaggatc gcttgagggc aggagtttga gaccagccta  33120
ggcaacatag caataccctg tctcttttaa acatttaaaa aatggctggg cacggtggct  33180
catgcctgta atcccagcac tttgggagga tgaggcaggt ggatcacctg aggtcaagag  33240
ttcaagacca gcctggccaa caagatggtg aaacccatct ctacaaaaat aacaaaaatt  33300
agccgggcat ggtggtgggt gcctgtaatc ccagctactt gggaggctga ggcaggagaa  33360
ttgcttgaac ctgggggaca gaggttgcaa tgagccgaga tttccccatt gcactccagc  33420
ttgggtgaca gagtgagact ctgtctcaaa aaataaataa ataaataaat aaataaataa  33480
gttagatggc atggtggcat gtgcttgaag tcccagctgc ttgggaggcc gaggctggag  33540
gatcacttga acctaggagt tcgaggctgc agtaagccat gattgcacca ctgcactcca  33600
gcctggaaaa tagagcaaga ccccgtcttt aaaaagcaaa aagaaaagaa caaaaaaaaa  33660
gccaaatcct cactctgcac tttccaggca tgtgacctca cttccctgag cctcaccttc  33720
cccagctgtg cagtggggat cacgagaggc ccttgggctg tgatgtcagc gcccagctct  33780
gtattgtctg tgtgctttaa tctggtttat gctgggacca acagccccat caccaggccc  33840
aaagcccacc actgccgttg tcatcactgg actcatgaaa tattttgaat tttgcccctg  33900
cttaaaggca ttcattatgt gcagctcagg gacaaagtca cacaaagaat tccatcatca  33960
gctgggcgcg gtggctcacg cctgtaatcc cagcactttg ggaggccgag gtcggcggat  34020
cacttgaggt caggagtttg agaccagcct ggccaacatg gcgaaatcct gcctctacta  34080
aaaatacaaa aattagccag gtgtggtggc gtgcgcctgt aatcccagct actcggctga  34140
ggcacaagaa ctgcttgcac ccgggaggtg gaggttgcaa tgagccgaga ttgtgccact  34200
```

-continued

```
gcactccagc ctaggcgaca gagtgagact ttgtctcaaa aaaaaaaaaa aaaagaattc  34260
catcattgga tgtgtccagt ccctcacagc ctccaaatcg cgtggctgtg cccttaacta  34320
gccacacccc atctccctgg catcacccag agaaacgtgc agttcatatc cactgctggt  34380
gctgtctccg tcattatcct cagagcgcca cggtgtccgt cccccgagtg tctgcaggca  34440
gagtcccacc ctgggccccc ttcgctgacc tcccaccctt caccctggcc cgcaggggag  34500
ctgcccctgt cgctggctgc ctgcaccaac cagccccaca ttgtcaacta cctgacggag  34560
aacccccaca agaaggcgga catgcggcgc caggactcgc gaggcaacac agtgctgcat  34620
gcgctggtgg ccattgctga caacacccgt gagaacacca agtttgttac caagatgtac  34680
gacctgctgc tgctcaagtg tgcccgcctc ttccccgaca gcaacctgga ggccgtgctc  34740
aacaacgacg gcctctcgcc cctcatgatg gctgccaaga cgggcaagat tggggtgagt  34800
gtgcggctgg gggcacagct gatccaccta ctcgtacccc tctgcacaca cacacgaggg  34860
tctgctgctg gtattcatta ttaatacgtg catgcacctc ccaacatgcc aaccccagtg  34920
tgcagatgtc ccagctcaag aacctgctat ggctccctag tgtccagcca agctccttag  34980
cttcatcccc gagcctctcg cctcatgtca ccctactgga tgttcaccac tccaccccca  35040
ccagccagga tgagccactg ataagaaact gagtccccgg gccctagccc agcggtgctc  35100
ccagcctcaa acctgttgaa tggccctgcc ccagttcctt ccctttctg ggccgcgcag  35160
catggggcct ggagaagggt ttctcaactt cagcatgatt attttgggcg gcaggctctt  35220
tgtggtgggg accgtcttgt gctattgcca gacattgatc tgcatcccgg gcctctaccc  35280
accagatgcc aggaacacct cccettacac ttgtgaccac caaaaatatc tccagaacat  35340
tgctgaattg tcctctgggg ggcaccatcg ctggattggg aaccaagtct ggagtatgct  35400
agaggcagga gcacctgtcc aagccctggc gctaccactt cccagtgtgt gacctcagac  35460
atctcatttc ccttttctgt gcctcagttt ccttgtctgt aaaatgggga tataagagtg  35520
tcctctggtg tggtgttgtg acaaatgcgg tgatccacat aaggctctta ggaaggagcc  35580
tgggagaagc agtaagtgtc acttacatgt ctgtaatgcc agctagttgg gaggctgagg  35640
tgagaggatc gtttaagtcc agcctggatt atttgagatc ccaaataaat aaaaaccaaa  35700
ataaaaaaaa atgtagcaaa aattactaaa attgcaatta taccatggcc ctgaggcagt  35760
agaaaggctc cagtttaaat cctggctttg gctaggctca gtggctcgtg tctgtaatcc  35820
tagcactttg ggaggctgag gtgggaggag cacttgagcc caggaggttg aggctgcaat  35880
gagctgtgat agtgccattg cactccagcc tgggcaacag agccagaccc tgtctcaaaa  35940
aaccccaaaa tcctggctgt gcacagtggc tcatgcctgt aatcccagca ctttgggagg  36000
ccgaggtggg cggatcacct gaggtcagga gttcaagacc agcctggcca acatggtgaa  36060
accccgtctc tactaaaaat acaaaaatat tagctgggtg tgatagtggg cacctgtaat  36120
cccagctact caggaggctg aggcaggaga attgcttgaa cctaggagga gagggttgca  36180
gtgtgctgag atcgcgccac tgcactccag cctgggtgac agagagagac tctgtctcaa  36240
aacaaaaacc ccaaaatcct aacattgcct gaccttgggc aattcccacc cctctctgtg  36300
cctccgcttc cctgtgtgta agccagggaa ggaggagtgg taacaggaag gaccgcatgt  36360
gatcgtcagt attataattc acatgtcatt aagatggatt cattgctatt ttaacggcat  36420
gaagaagata ttcattacaa ttaagatgtt gaaggctcat ccaggttctg tctggctcca  36480
gctgactggt taagtggctt ctggaacacc cttcgttttt cccagcctcc attctttatc  36540
tgtaaaccaa gataataaga gcaagaatta aacaagatga ggaaagggtc ctccagcagc  36600
```

-continued

```
cggtgcttag ctgttttctg gggaggcgtc atgtgctgag ctgggcccag ccctgggggt  36660
ctttccagtg tgagccccct gaccctcctg gccccctgtg cagatctttc agcacatcat  36720
ccggcgggag gtgacggatg aggacacacg gcacctgtcc cgcaagttca aggactgggc  36780
ctatgggcca gtgtattcct cgctttatga cctctcctcc ctggacacgt gtggggaaga  36840
ggcctccgtg ctggagatcc tggtgtacaa cagcaagatt gaggtgggct ccaggagggg  36900
gcatggggtg tgaggaagga ggggcagggc tgggagtagg gacagggccc tggggctggg  36960
ctgggggaga cagccccagc ctctaggacc caacgtggtg ggtctgttgg ctgaatgcaa  37020
gagaaggtgc caactaagtg cccagaacag tgtctgccat gtgaggaaat gagcaagact  37080
tgtgggaaga tggacttttg gggcaggtag gactgggttg ggatcctggc tctgtaactt  37140
acatgctgtg tgtctcagga caagtggctc cacctctctg ggtctcagct tcttcatttg  37200
taacctgggg ataaggatca tggatatccc atggggttct tgggaggacc aaagaggtta  37260
atttagaat ggcttggcac agagtaaaca ttatgtcagc ttttactact catggttgtt  37320
atatgaactt ttgaaagctc tttttttcg gtcaggcatg gtggcttatg cctgtaattc  37380
tagcattttg gggagccaag gtgggcggat tgcttgaagc caggagtttg agactagcct  37440
gggcaatatg gcgaaacccc gtctctacca aaaaaaaata ataaaaatga aaattagcta  37500
ggcatggtgg tgcgagcctg tagtcccagc tacttgggag gcgaggtggg aggatcacct  37560
gagcctgggg aggtcgaggc ttcagtgagc cgagatcatg ccactgcact ccagcctggg  37620
tgacagagtg agatcctgtc tcaaaataaa caaacaaaca aacaaacaaa aaaccaagct  37680
tttttttccc tacttagcag tattttgtga acgtcgttct gtacttttaa atattctttg  37740
gtaatattgt cgctgcatgt aaacatacca tattcaaatg aactgttctc ttattgctgg  37800
tcgcttgggt ttgtttctgc ctttatcagg aataacacta taagagcatc tctgtggctg  37860
ctttattgca caaatcatga ttatagagaa actcaagtta ataaagggct aggaagctat  37920
aaaaatggag cagaaaatgc tggggactgg gtgcaggtgg tcttccttct agccctgccc  37980
tgtggcttac tggtctgtga gcttggcttc cttgcaagac ctcatttccc tcatttttg  38040
aattagtgac catcttgatt taaattagtg gtggcaggag gtttagcatc tcaggtgcaa  38100
actgattgat tagtagtgtc tacccaggga actgtatgaa tacaattgtg cagggctcaa  38160
ttattgatgt ctgccctggg ttcagaattg gagaattgtg gtgagtcaat catttatcat  38220
ctttgggcaa aatttctcaa tctttctctc tgaatcagaa tttctgagag cggaggccag  38280
gatttatact tgcagcaagt tacataaatt attttgcggc cagcagcttg gtactatcca  38340
cagattggag tttgggaacc atgagaataa atgtcttttt ttcttttttg agatggagtc  38400
tcactcttgt tgcccaggct ggagtgcagt agtgcgatct aggctcactg caatctccgc  38460
ctcccaggtt caagtgattc tcctgcctca gccttaggag tagctgggat tacaggtgtg  38520
caccaccacg cccggctaat tgttgtgttt ttagtggaga cagggtttca ccacattggc  38580
caggctgatc ttgaactgct gaccttaggt gatccgcctg tcttggcctc ccaaagtgct  38640
aggattacag gcatgagcca ctgcggccgg cctgaaaata aatgtctttt aagggacttt  38700
ccagttccga gttctgtgat gctagaatag ggtggaaagg tacattgagg cagaattggg  38760
cagctgaatc cattcatgaa tccgtgaatg cagctgagga atggatggaa agagaaagcg  38820
ctgtccgggt ggagggtggg ggaaggcaca cccgaggcag cctgcctgga ccccccaccc  38880
atctcaggaa ggcagccccc gaccaccctg cctctcttag aaccgccacg agatgctggc  38940
tgtggagccc atcaatgaac tgctgcggga caagtggcgc aagttcgggg ccgtctcctt  39000
```

-continued

```
ctacatcaac gtggtctcct acctgtgtgc catggtcatc ttcactctca ccgcctacta  39060
ccagccgctg gagggcacag tgagtgcccg gggaccgggc aggggctggg gcaggcactg  39120
ggctgagcca tgcaggactg gggcacaacc tcatccttct gggtcccctg taggggggacc  39180
cggagaaggt ttaggaacag gttggggagg cgccctccag catccacggg tggccctgag  39240
ctgggaggag gaagactcag gaggaagaga gtgaaggagg aggctccatg ggatgccgat  39300
gtttcgggcc tgggggaaca tctggattgg gggccagatg ttggaggggc tgggtgacga  39360
cctgtgtgcc cttgctgctc cccagccgcc gtacccttac cgcaccacgg tggactacct  39420
gcggctggct ggcgaggtca ttacgctctt cactggggtc ctgttcttct tcaccaacgt  39480
aagtgcctgg cccccgtgcc ccccaccctg cctgccctcc tcttctcttc ctgcacctct  39540
tttctctccc tctttttctc ttctctctcc tccaaatggt ccttctcctt tccttcctcc  39600
ttttattttc ccatttctct tctacctcct ccaatcccac gttctccatc tctgcttttt  39660
tctccttttc taacaggaaa gagtcctttg tcttttctct gtaccagcct ctgcctccct  39720
ctcttctatc cctttctctg tctcctctct cctcctctcc tctcctgctg gccccacccc  39780
tttcacgtgc cccctcctgt cttccagatc aaagacttgt tcatgaagaa atgccctgga  39840
gtgaattctc tcttcattga tggctccttc cagctgctct agtgagtaga ggtccctggg  39900
ccggcagctt ctgggtgagg aaggtgggtt tgggctgcta ggtcgtccag attcaggaga  39960
gaggtgattc tgttagaaat gaatgcaccc aacctgggca gctctaaccc aaagtcagga  40020
caaagccaca aacaataggg tcttctggtt caagaaaaat tctgattgct agggagttat  40080
catatacaac atggatagaa ataattttaa cctcttatgc tggtgaatga ttgctaatgt  40140
ctgcctgaag tgccatgtta agaattttgc acctgtgtct gtgtttagtg ggaaagagtt  40200
gggattgatt aatgatgtct gcctgggaca gagaatgaga gagttactga gtgtgtgtta  40260
cctctttcac atttccctta gagttggaga atgatgaaat tcacttagcc acaaaatctc  40320
cactgaacac cactaaatct ttctttagca attccaaggg gcatcacttc aggatcctgt  40380
gggacctcag gattaattgc cagctaattg aatgttcttg ttaacagaat gctggggaac  40440
cctgctaatc cactttgttt cttttctggg ggtctagaag gcattgggaa gtcctgatac  40500
cctggagggc ttggaggcgt gtcttcccct ccagagcctc attgtcccct ctcccctctg  40560
gcctctcttg tggtctctgc tgcactgcag cttcatctac tctgtcctgg tgatcgtctc  40620
agcagccctc tacctggcag ggatcgaggc ctacctggcc gtgatggtct ttgccctggt  40680
cctgggctgg atgaatgccc tttacttcac ccgtgggctg aagctgacgg ggacctatag  40740
catcatgatc cagaaggtac gggctgggag gaccctctgg actcgtgtgt tcctggaggg  40800
agtcacacac acaccacatg cacacttatg cacctgcaga cctgaggatg ctgggtaccg  40860
tgggggcagg aggcatggtc tggacactgg ggtgggacca gggtggagat ggaggaatgg  40920
ggaaagtgag aaaccatgtg tctcctcttt gcctccataa tcccgctggg gtctttagat  40980
tctcttcaag gaccttttcc gattcctgct cgtctacttg ctcttcatga tcggctacgc  41040
ttcaggtgag ctctgggtgc tcaggtggtc ctggcagggg tggtgcaagg acgggaacag  41100
tagccatgat gtatagggga caatagcagc cttgctgagt tctttttttt tttttttttt  41160
ttttgaggtg gagttttgct cctgttgccc gggctggagt gcaatggcac aatctcagct  41220
cactgtaacc tccacctccc aggttcaagt aattctgcct cagcctccca cgtagttggg  41280
attacgggct cctgccacca cgccccacta ttttttaatt tttttttttt tgtattttta  41340
gtagagatgg ggtttcacca tgttggccat gctggtcttg aactcctgac ctcaggtgat  41400
```

-continued

```
ccaccctcct tggcctccca aaatggtggg attacaggtg tgagccaacg cgcctggcca  41460
ctgagttctt atttgtgtgc caggcaccag actaagtacg tttccatcct tgcctcccaa  41520
caagcctgta agctaagtgc ctttattatc ccctattata gaaaaggaaa ctgaggctta  41580
ggagggttaa ataactagca caagttcaaa agccagtgaa tggtggccgg gcgcagtggc  41640
tcacatctgt aatcccagca cttcaggagg ctgaggcggg tagatcactt gaggtcagga  41700
gtttgagacc agcctggcca acatggcaaa accccgtctc taccaaaaaa tacaaaaatt  41760
agacaggcat ggtggcgcgc aactatagac ccagctactc gggaggctga ggcacaagaa  41820
tcgcttgaac ccagggggtg gaggttgcag taagccaaga tggcaccact gcactccagc  41880
ctgggcaaca cagcgagact ctgtctcaaa aaaaaaaaaa aaaaaaaagc tggtgaatgg  41940
caaaactgga gtattagcta ttgctacaaa ggaagccacc taaagtgggg cttaaaatag  42000
cacccactta ttattattat ttttttgtg gcaaggtctc actctgtcac caaggctgga  42060
gggcagtggt gctcttggct cactgcaatc tctgcctcct gggttcaagc gattctcttg  42120
cctcagcctc tcgaatagct gggattacag gcgtgtgcca ccacgcatgg ctaagtttta  42180
tatttttggt agagatgggg tttcactatg ttggccaggc tggtctcgaa ctcctgaccc  42240
caagtgatcc acccaccttg gcctcccaaa gtgctgggat tacaggcgtg agccactgta  42300
ccaggccaac ttactattgc ttatgagtca atgggtcagc tgggtggctg tgctgccctg  42360
ggccaggttt ggctgatccc tacaggctct tgtgcctgtg gtcagctggc aggctggctg  42420
ctggctgact ggtctagcta gtatggactt ggttagaggg ggtttgctat ctatcttcca  42480
catggtcact catttctgga cagctagctt gggcttgtcc acatggtggc cttagggttc  42540
caagaacatg agcagaagtg ttcaaggaca cctcctggca tggcatcact gctgccttac  42600
tctgttggcc aaagcaagtc acaaggccag cctcgattca agggatgggg aaatagacgc  42660
cacttctttt tttccatttt tttttttgg tggaggcagg gtcttgctat gttgcccagg  42720
ctggtcttga actcctgggc tcaagcagtc ctcctgcctc agcctcccaa agtgcaggat  42780
tataggcgcg agccactgca cctggcctag actccacttc ttagtgggag aagctgtaaa  42840
gccacattga aggaggatgg atacatggaa ggataaaatt taataattaa actagcagcc  42900
caggtatttt cttaaagccc aacatcagct cccttgatat accttcttcg tgatgtcatg  42960
atgccactaa gaagcattct gggacctcag tggcatgggt catgggagaa ggaccaggga  43020
ccagggctgg agaaactgac caagtccttg ggctgatccc cgaggtgtgg gtaatctgac  43080
atcaatgccc agcatccaaa ggggaatggc caactcaggt tagacctgga cacatacaca  43140
tctgagcagg ttcatctggg gacgagcctg gcacaggaat ctgacaaggg tgatatttta  43200
acccacgata gtggccaagt ctctaggtag attattggtg ggaagtggaa ttgtagtttt  43260
cactggggag atagggacag ggtacagctt tcccttccca gggatcacac tggacaaact  43320
agacagtgtc aagggttcaa caacagtttg ggattcaggt cagggatcta gccctactgc  43380
agtcctagtt attgaaacta aggagaaaca agggttagag tagcagctta gcagtcagct  43440
tggttgcagg tcttctcctt ataggatgca ctagatctca attctgaggc tgacatgaca  43500
taaacaggac acacatgctt ctgttcccac actttggtgt ccatagcaga catcactaat  43560
ggatcacaga acagtttttc cggtgagtcc agacaaggtc tcagaatcct tctcaacaca  43620
gtgtttcacc aggtactata caactgaaga acattagcat atgagttgaa atctgcatac  43680
tctaatccct ggttgcaggc agtatgacat tctgtgcccc actgactgat gggactgagt  43740
cttcttcatg ctcccctccc tggctggttt agggacaggt tgttgctgcc aaactgtgtt  43800
```

```
gagaaggaat ctgaagctcc acctgggctt agtaggaaag gagaaccatg atgagtttga  43860
gatgtctaga gcaggagagg ccccttagag aacacggctt tggggacagt caggactgat  43920
gcctggtttc agcccccact tttcctctct gggttggggt ggagtgggaa actgtcagag  43980
agagagtcta cccctgcgaa taggggcatt ccagagcccc caagacctct aagaatggta  44040
ggccgcatta ggatttccca acactattga catttgagac cagatcattc ttcgtggcgg  44100
ggaccatcct gtgcattgta gggtgtcagg cagcacccct ggcctccacc cacctgatgc  44160
cagtagcacc cccaccccca gttgtaacaa ccaaatatgt ctctagacat tgtcaaatgt  44220
cccctggtgg gaaaaactga gaccctccct ggactagatc ctgaaaacct tttccctccc  44280
ggtagcaggg aaccaccagg ttgtgtaagg aggggtgaac tgtcccaggt tggaaacaga  44340
gcaggtcaaa actcctacgc ttatcagtag tgggattgag cctgtgagta gccactgcac  44400
tccagcctgg gcaacatagc aagaccccat ctcagaaaga aagagagaga gagagagata  44460
acctcttcct tatcagcaag agtttatgga aaggcttcaa aggttttggg atcaggagga  44520
cctgggtctg gtgtggcttg gctgatgtgt agggtgacat gggtcagcgt gtgggccagc  44580
gtgctccgct cactaggcct cagctttctc ctccagcaaa tgagaatgac accctccacc  44640
tctctgtggg tgtgctcaca ctcagtgagt gccaccccta tcctcccaca gccctggtct  44700
ccctcctgaa cccgtgtgcc aacatgaagg tgtgcaatga ggaccagacc aactgcacag  44760
tgcccactta cccctcgtgc cgtgacagcg agaccttcag caccttcctc ctggacctgt  44820
ttaagctgac catcggcatg ggcgacctgg agatgctgag cagcaccaag taccccgtgg  44880
tcttcatcat cctgctggtg acctacatca tcctcacctt tgtgctgctc ctcaacatgc  44940
tcattgccct catgggcgag acagtgggcc aggtctccaa ggagagcaag cacatctgga  45000
agctgcaggt gaggccccag ggcccccagc cccactctac cagccaccct cgtccttccg  45060
aggagaccca cccgactggc ttcctcggcc ttccactctg agcaagcagt gtcttctcat  45120
tctccctcca cttctctgtc ggtaaaatgg gcatcagagg ctgctgctga cttcccagag  45180
ctgcctagtg aattttgagg tggcttcttg cctggctgcc agcagtgggc tcagattctc  45240
cttgtggtcc agctcacagg acacagtcgg ctccacctag catgactgag tgacttctgc  45300
cggctcagaa agtgctccgt gggcatcagc gtttcagcag gggtcccacg ctgagcccag  45360
gggcagcttt tgtgctctag cactccagca cagggatgtc agcattctca tgggggtctt  45420
tttctagcaa ctgtgagcat gcttcctaga ggagaaacca atggggacag gggccgcctt  45480
ggcccgggga gctgcagaaa gtttttactt accaaaagct ttctatgcaa tcctggaaag  45540
aacaggccct gggatcacag ccctcccagg ccaggtgcag cctacaaacc tggtgtccta  45600
ataaacagtg ctgccccacg gcccaggaat acagcacccg tgtttacctt gactgtgcat  45660
ttcaggaaaa tggtgcagtg agaaaaaagg gcccaaggtt gtcctcccag gactgggtct  45720
gagggaaaca gctctggcct gctcttaacc tttatctata ttgcttactt cattgggcct  45780
cagtttcccc actgggcatt actcacagga tgcaaactgg gcatcctgtg ggctggagtg  45840
caatggtgtg atcttggctc actgcaacct ctgcctccca ggctcaagtg attctctgtc  45900
ctcagcctcc cgagtagctg gggctaaggt gtgcaccacc tcacccggct aatttttgta  45960
tttttgtaa agatggggtt tcaccatgtt gcccaggctg gtcttgaact tctgagttca  46020
agctatccac ctgccttggc ctcctaaagt gctgagattg caggtgtgag ccactgcacc  46080
cagcatcaga ccattatatt aaaaacaaca acaacaacaa aaaactgcaa aatttaaaaa  46140
ttaagagatt ccctatgaaa acccagattt ctggcttttc ttgaaaagtt ggaagctcca  46200
```

```
ggcagtgcag ggtccggatt cctgcctggc agccctcagg tggggtgagt ggcagctgcc  46260
cccttacacg tgggcatttg ctccctgttc tccccagtct ctacccctcc ctcactgaga  46320
ggcaactgct gtgtaagtgt gatagggctt gggcggcagc ctttctgcac ctgatcctgt  46380
ttcacccatt tgttttcctg cctgccacct gtgggtattt gagtttataa accctgtgtc  46440
tagtggggag taggagtcta aatgcctagt tctgggccca ccctggcccg ttgtctcatt  46500
tctgccacca gagcggcagg cgcaggctgt gaggctcacc gatgtccctc ctgaccctcc  46560
ctccccgcag tgggccacca ccatcctgga cattgagcgc tccttccccg tattcctgag  46620
gaaggccttc cgctctgggg agatggtcac cgtgggcaag agctcggacg gcactcctga  46680
ccgcaggtgg tgcttcaggt gaggctgggg cagtggggcc aggatggcag ggcggaactg  46740
tccccactgg ctcggggccc ctgctgctcc agcgtcgtct acccattgca atttctggag  46800
ccactgaggc cccaagaggc ccgagcagag ttcatttcca ccaggcgatc tcaggcaagt  46860
cagcccacct ctctcagcct cagtttcttc atctgtggaa tgagacaatg atctcacggg  46920
ctcctaggct ggcggtgcgg attagacagg tcagcacgtg agaagtgctc agccagtgcc  46980
cgacgcgcat cgggacgcca caggctcccc tgttcttgct caggggggaag cagagacttg  47040
gatggtgggt tcattttaga gcatcaccct gtatctacca aacagtgggg tgagctctag  47100
tgccctcggt gaaatgggaa gctgaggaat gtgcagtttc cagggctgga gacctcaccc  47160
agcccatctg cagaatgact ccgtgttcca gaggcacagg gagtgccagc ttcttagggg  47220
aaccccttca tgaatctttt ctttccagtt gattcattca ttgtaaagtg gttgtcagca  47280
tggagcataa gcagaatgtt tggagtcaga caaagtcagt ttcttcatct gtgaaatggg  47340
aacaataata gaacccacct cctaggccat ccgatcagtt caattccatt ttttgtttgt  47400
ttttagaggc agggttgctc aggctggagt gcagtggtgt gatcatagct gactgcagcc  47460
tccaactcct ggtctcaagc gatcctccca cctcagcctc ctcatgccac catgtccgac  47520
caatttttaa tttttttgta gagatggggt tcttgctatg ttgcccaggc tggtctcaaa  47580
ctcctggtct caagcgatct tcccacctca gcctcccaaa atgctgggat tacaggcgtg  47640
agccaccaca cccagcctct gttcagtttg aatccaaagc tcaaatcttg gctgggtgtg  47700
gtggctcgtg cttgtaatcc cagcactttg ggaggccaag gtgggtggat cacctgaggt  47760
caggagtttg agaccaccct gggcaacatg gtgaaaccct gtctccacta aaaatacaaa  47820
aattagtcgg gagtggtggc atgcacctgt aatcccagct actcgggagg ctgaggcagg  47880
agaatcgctt gaacctggta ggtggaggtt gcagtgagcc gagattgcac tactgcactc  47940
cagtctggcg gacagagcaa gactctgcct taaaacaaac aaacaaaaat gaatagatag  48000
gataaaaaat taaagataat atgtaaaaaa aaaagataat atataaaaaa atgagtggat  48060
aaacaaaatg tgggctatgt gtacagtgaa atattatctg ggccaggcgt ggtgactgta  48120
ataccaacac tttgggaagc gaggcaagag gattgcttga gcccaggagt tcaagaccaa  48180
catagtgaaa ccccatctct acaaaacgtt tttaaaaaat tagccaggtg tggtggcata  48240
tccctgtaat cccagctaca tggggggctg aagtgggcgg atcacttgag cctgggaggt  48300
caaggttgca gtgagctgtg atcgtgccac tgcaccctag cctgggcaat ggagtgagac  48360
cctgtctcaa aagaaggtta aaaaaaataa tttctgcttg ggggaatgga agaattttgg  48420
aaatagatag ctgtgatggt cacacaatgt ggatgtgctt aatgccactg aattgtatac  48480
tcaaaaatga ttaagatggc aaattttttg tgtgtgtata cacacacaca cacacacaca  48540
cacacacgtc tttttttttt tttttttgag atggagtctt gctttgtccc ccaggttgga  48600
```

```
gtgcagtggc gtgatctcgg ctcactgcaa ctgcctccca ggttcaagtg attttcctgc  48660
ctcagcctct cgggtcactg ggactatagg cacccgccac catgccccgc taattttttt  48720
tttaattttt tttaattttt agtagaggtg gggtttcacc atgttggcca ggctggtctc  48780
gaactcctga cctcaaatga cccacccacc tcggcctccc aaagtgctgg gattgcaggc  48840
atgagccacc acgcccagcc ttgttatgta tatgttacca taataaaaaa ataggagggt  48900
gtgctgggga tggtggcatg gagagcgtct ctgaggggtt ccccatgacc ctctgcttgg  48960
gccctgccag ggtggatgag gtgaactggt ctcactggaa ccagaacttg ggcatcatca  49020
acgaggaccc gggcaagaat gagacctacc agtattatgg cttctcgcat accgtgggcc  49080
gcctccgcag gggtgagtgg aggggcgggt gcggaggggga gccccagtcc attctcatca  49140
cgaatttgct ttgagcagtc ctgcttcttt ccgggactca gtgtccgtgt ctacagaatg  49200
agagagtgtg cccctgagct tcctctgctg cttgtgaatg cctggggcac ctcacctacg  49260
tggcttcatc ctggccctcc ctactgttga cataagctgg cctggggagg gaggacgagc  49320
tcctcagcca tccctgtgtg gagaaaacct tcctgtttgt ccagtaagcc atgagcacgc  49380
gagacgcagc tggagaggac acaggcactc agggcattcg gctccaggct tgaatcctgg  49440
ttcctccatt ctctcctggg gaggcacctt gacctctctt gagccccagt ttccacctct  49500
gtaaaatgag catagtcaca tccccccttc agaacactgt ggagtgccca gtacacagta  49560
ggcactcaat atacgcacgc tctctctcca ccaaccccca cccctccctc tgatgtgctc  49620
tcggtgcaga tcgctggtcc tcggtggtac cccgcgtggt ggaactgaac aagaactcga  49680
acccggacga ggtggtggtg cctctggaca gcatggggaa cccccgctgc gatggccacc  49740
agcagggtta cccccgcaag tggaggactg atgacgcccc gctctaggga ctgcagccca  49800
gccccagctt ctctgcccac tcatttctag tccagccgca tttcagcagt gccttctggg  49860
gtgtcccccc acaccctgct ttggccccag aggcgaggga ccagtggagg tgccagggag  49920
gccccaggac cctgtggtcc cctggctctg cctccccacc ctggggtggg ggctcccggc  49980
cacctgtctt gctcctatgg agtcacataa gccaacgcca gagcccctcc acctcaggcc  50040
ccagcccctg cctctccatt atttatttgc tctgctctca ggaagcgacg tgacccctgc  50100
cccagctgga acctggcaga ggccttagga ccccgttcca agtgcactgc ccggccaagc  50160
cccagcctca gcctgcgcct gagctgcatg cgccaccatt tttggcagcg tggcagcttt  50220
gcaaggggct ggggccctcg gcgtggggcc atgccttctg tgtgttctgt agtgtctggg  50280
atttgccggt gctcaataaa tgtttattca ttgacggtg                         50319
```

<210> SEQ ID NO 2
<211> LENGTH: 3254
<212> TYPE: DNA
<213> ORGANISM: Homo sapiens

<400> SEQUENCE: 2

```
ccggccggga ttcaggaagc gcggatctcc cggccgccgg cgcccagccg tcccggaggc     60
tgagcagtgc agacgggcct ggggcaggca tggcggattc cagcgaaggc cccccgcgcgg   120
ggcccgggga ggtggctgag ctcccccgggg atgagagtgg caccccaggt ggggaggctt   180
ttcctctctc ctccctggcc aatctgtttg agggggagga tggctccctt tcgccctcac    240
cggctgatgc cagtcgccct gctggcccag gcgatgggcg accaaatctg cgcatgaagt    300
tccagggcgc cttccgcaag gggggtgccca accccatcga tctgctggag tccaccctat   360
atgagtcctc ggtggtgcct gggcccaaga aagcacccat ggactcactg tttgactacg    420
```

```
gcacctatcg tcaccactcc agtgacaaca agaggtggag gaagaagatc atagagaagc    480
agccgcagag ccccaaagcc cctgcccctc agccgccccc catcctcaaa gtcttcaacc    540
ggcctatcct ctttgacatc gtgtcccggg gctccactgc tgacctggac gggctgctcc    600
cattcttgct gacccacaag aaacgcctaa ctgatgagga gtttcgagag ccatctacgg    660
ggaagacctg cctgcccaag gccttgctga acctgagcaa tggccgcaac gacaccatcc    720
ctgtgctgct ggacatcgcg gagcgcaccg gcaacatgcg ggagttcatt aactcgccct    780
tccgtgacat ctactatcga ggtcagacag ccctgcacat cgccattgag cgtcgctgca    840
aacactacgt ggaacttctc gtggcccagg gagctgatgt ccacgcccag gcccgtgggc    900
gcttcttcca gcccaaggat gagggggct acttctactt tggggagctg cccctgtcgc    960
tggctgcctg caccaaccag ccccacattg tcaactacct gacggagaac ccccacaaga   1020
aggcggacat gcggcgccag gactcgcgag gcaacacagt gctgcatgcg ctggtggcca   1080
ttgctgacaa cacccgtgag aacaccaagt ttgttaccaa gatgtacgac ctgctgctgc   1140
tcaagtgtgc ccgcctcttc cccgacagca acctggaggc cgtgctcaac aacgacggcc   1200
tctcgcccct catgatggct gccaagacgg gcaagattgg gatctttcag cacatcatcc   1260
ggcgggaggt gacggatgag gacacacggc acctgtcccg caagttcaag gactgggcct   1320
atgggccagt gtattcctcg ctttatgacc tctcctccct ggacacgtgt ggggaagagg   1380
cctccgtgct ggagatcctg gtgtacaaca gcaagattga gaaccgccac gagatgctgg   1440
ctgtggagcc catcaatgaa ctgctgcggg acaagtggcg caagttcggg gccgtctcct   1500
tctacatcaa cgtggtctcc tacctgtgtg ccatggtcat cttcactctc accgcctact   1560
accagccgct ggagggcaca ccgccgtacc cttaccgcac cacggtggac tacctgcggc   1620
tggctggcga ggtcattacg ctcttcactg ggtcctgtt cttcttcacc aacatcaaag   1680
acttgttcat gaagaaatgc cctggagtga attctctctt cattgatggc tccttccagc   1740
tgctctactt catctactct gtcctggtga tcgtctcagc agccctctac ctggcaggga   1800
tcgaggccta cctggccgtg atggtctttg ccctggtcct gggctggatg aatgcccttt   1860
acttcacccg tgggctgaag ctgacgggga cctatagcat catgatccag aagattctct   1920
tcaaggacct tttccgattc ctgctcgtct acttgctctt catgatcggc tacgcttcag   1980
ccctggtctc cctcctgaac ccgtgtgcca acatgaaggt gtgcaatgag gaccagacca   2040
actgcacagt gcccacttac ccctcgtgcc gtgacagcga gaccttcagc accttcctcc   2100
tggacctgtt taagctgacc atcggcatgg gcgacctgga gatgctgagc agcaccaagt   2160
accccgtggt cttcatcatc ctgctggtga cctacatcat cctcaccttt gtgctgctcc   2220
tcaacatgct cattgccctc atgggcgaga cagtgggcca ggtctccaag gagagcaagc   2280
acatctggaa gctgcagtgg gccaccacca tcctggacat tgagcgctcc ttccccgtat   2340
tcctgaggaa ggccttccgc tctggggaga tggtcaccgt gggcaagagc tcggacggca   2400
ctcctgaccg caggtggtgc ttcagggtgg atgaggtgaa ctggtctcac tggaaccaga   2460
acttgggcat catcaacgag gacccgggca agaatgagac ctaccagtat tatggcttct   2520
cgcataccgt gggccgcctc cgcagggatc gctggtcctc ggtggtaccc cgcgtggtgg   2580
aactgaacaa gaactcgaac ccggacgagg tggtggtgcc tctggacagc atggggaacc   2640
cccgctgcga tggccaccag cagggttacc cccgcaagtg gaggactgat gacgccccgc   2700
tctagggact gcagcccagc cccagcttct ctgcccactc atttctagtc cagccgcatt   2760
tcagcagtgc cttctggggt gtcccccac accctgcttt ggccccagag gcgagggacc   2820
```

agtggaggtg ccagggaggc cccaggaccc tgtggtcccc tggctctgcc tccccaccct 2880
ggggtggggg ctcccggcca cctgtcttgc tcctatggag tcacataagc caacgccaga 2940
gcccctccac ctcaggcccc agcccctgcc tctccattat ttatttgctc tgctctcagg 3000
aagcgacgtg acccctgccc cagctggaac ctggcagagg ccttaggacc ccgttccaag 3060
tgcactgccc ggccaagccc cagcctcagc ctgcgcctga gctgcatgcg ccaccatttt 3120
tggcagcgtg gcagctttgc aaggggctgg ggccctcggc gtggggccat gccttctgtg 3180
tgttctgtag tgtctgggat ttgccggtgc tcaataaatg tttattcatt gacggtgaaa 3240
aaaaaaaaaa aaaa 3254

<210> SEQ ID NO 3
<211> LENGTH: 3057
<212> TYPE: DNA
<213> ORGANISM: Homo sapiens

<400> SEQUENCE: 3
ccggccggga ttcaggaagc gcggatctcc cggccgccgg cgcccagccg tcccggaggc 60
tgagcagtgc agacgggcct ggggcaggca tggcggattc cagcgaaggc ccccgcgcgg 120
ggcccgggga ggtggctgag ctccccgggg atgagagtgg caccccaggt ggggaggctt 180
ttcctctctc ctccctggcc aatctgtttg agggggagga tggctccctt tcgccctcac 240
cggctgatgc cagtcgccct gctggcccag gcgatgggcg accaaatctg cgcatgaagt 300
tccagggcgc cttccgcaag gggggtgccca accccatcga tctgctggag tccaccctat 360
atgagtcctc ggtggtgcct gggcccaaga aagcacccat ggactcactg tttgactacg 420
gcacctatcg tcaccactcc agtgacaaca agaggtggag gaagaagatc atagagaagc 480
agccgcagag ccccaaagcc cctgcccctc agccgccccc catcctcaaa gtcttcaacc 540
ggcctatcct ctttgacatc gtgtcccggg gctccactgc tgacctggac gggctgctcc 600
cattcttgct gacccacaag aaacgcctaa ctgatgagga gtttcgagag ccatctacgg 660
ggaagacctg cctgcccaag gccttgctga acctgagcaa tggccgcaac gacaccatcc 720
ctgtgctgct ggacatcgcg gagcgcaccg gcaacatgcg ggagttcatt aactcgccct 780
tccgtgacat ctactatcga ggtcagacag ccctgcacat cgccattgag cgtcgctgca 840
aacactacgt ggaacttctc gtggcccagg gagctgatgt ccacgcccag gcccgtgggc 900
gcttcttcca gcccaaggat gagggggggct acttctactt tggggagctg cccctgtcgc 960
tggctgcctg caccaaccag ccccacattg tcaactacct gacggagaac ccccacaaga 1020
aggcggacat gcggcgccag gactcgcgag gcaacacagt gctgcatgcg ctggtggcca 1080
ttgctgacaa cacccgtgag aacaccaagt ttgttaccaa gatgtacgac ctgctgctgc 1140
tcaagtgtgc ccgcctcttc cccgacagca acctggaggc cgtgctcaac aacgacggcc 1200
tctcgcccct catgatggct gccaagacgg gcaagattgg gaaccgccac gagatgctgg 1260
ctgtggagcc catcaatgaa ctgctgcggg acaagtggcg caagttcggg gccgtctcct 1320
tctacatcaa cgtggtctcc tacctgtgtg ccatggtcat cttcactctc accgcctact 1380
accagccgct ggagggcaca ccgccgtacc cttaccgcac cacggtggac tacctgcggc 1440
tggctggcga ggtcattacg ctcttcactg ggtcctgtt cttcttcacc aacatcaaag 1500
acttgttcat gaagaaatgc cctggagtga attctctctt cattgatggc tccttccagc 1560
tgctctactt catctactct gtcctggtga tcgtctcagc agccctctac ctggcaggga 1620
tcgaggccta cctggccgtg atggtctttg ccctggtcct gggctggatg aatgcccttt 1680

```
acttcacccg tgggctgaag ctgacgggga cctatagcat catgatccag aagattctct   1740

tcaaggacct tttccgattc ctgctcgtct acttgctctt catgatcggc tacgcttcag   1800

ccctggtctc cctcctgaac ccgtgtgcca acatgaaggt gtgcaatgag gaccagacca   1860

actgcacagt gcccacttac ccctcgtgcc gtgacagcga gaccttcagc accttcctcc   1920

tggacctgtt taagctgacc atcggcatgg gcgacctgga gatgctgagc agcaccaagt   1980

accccgtggt cttcatcatc ctgctggtga cctacatcat cctcaccttt gtgctgctcc   2040

tcaacatgct cattgccctc atgggcgaga cagtgggcca ggtctccaag gagagcaagc   2100

acatctggaa gctgcagtgg gccaccacca tcctggacat tgagcgctcc ttccccgtat   2160

tcctgaggaa ggccttccgc tctggggaga tggtcaccgt gggcaagagc tcggacggca   2220

ctcctgaccg caggtggtgc ttcagggtgg atgaggtgaa ctggtctcac tggaaccaga   2280

acttgggcat catcaacgag gacccgggca agaatgagac ctaccagtat tatggcttct   2340

cgcataccgt gggccgcctc cgcagggatc gctggtcctc ggtggtaccc cgcgtggtgg   2400

aactgaacaa gaactcgaac ccggacgagg tggtggtgcc tctggacagc atggggaacc   2460

cccgctgcga tggccaccag cagggttacc cccgcaagtg gaggactgat gacgccccgc   2520

tctagggact gcagcccagc cccagcttct ctgcccactc atttctagtc cagccgcatt   2580

tcagcagtgc cttctggggt gtcccccac accctgcttt ggccccagag gcgagggacc   2640

agtggaggtg ccagggaggc cccaggaccc tgtggtcccc tggctctgcc tccccaccct   2700

ggggtggggg ctcccggcca cctgtcttgc tcctatggag tcacataagc caacgccaga   2760

gcccctccac ctcaggcccc agcccctgcc tctccattat ttatttgctc tgctctcagg   2820

aagcgacgtg acccctgccc cagctggaac ctggcagagg ccttaggacc ccgttccaag   2880

tgcactgccc ggccaagccc cagcctcagc ctgcgcctga gctgcatgcg ccaccatttt   2940

tggcagcgtg gcagctttgc aaggggctgg ggccctcggc gtggggccat gccttctgtg   3000

tgttctgtag tgtctgggat ttgccggtgc tcaataaatg tttattcatt gacggtg      3057
```

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 4

```
gcacaccgcc guacccuuau u                                              21
```

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 5

```
uaaggguacg gcggugugcu u                                              21
```

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 6
gaccaaaucu gcgcaugaau u 21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 7
uucaugcgca gauuuggucu u 21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 8
caaccggccu auccucuuuu u 21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 9
aaagaggaua ggccgguugu u 21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 10
gaacccgugu gccaacaugu u 21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 11
cauguuggca cacggguucu u 21

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Arg Arg Lys Arg Arg Arg
1 5

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
caaaccgatt tgaccgagat 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gttcagcaca gccttcatca 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
cagctgggag gaaaactcag 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gggaggaagt ccttttccag 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
gacggggacc tatagcatca 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
aacaggtcca ggaggaaggt 20

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gactacctgc ggctggc 17

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ttcatccagc ccaggac 17

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
cactcgttca ttggcacctg cttt 24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gcagcttcgt cagcacaatc aca 23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ccattcgttc atcggcactt gctt 24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ttatgaagca ttgccaccag cagc 24

-continued

```
<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

accacagtcc atgccatcac                                                  20


<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

tccaccaccc tgttgctgta                                                  20
```